US008435525B1

(12) United States Patent
Bush

(10) Patent No.: US 8,435,525 B1
(45) Date of Patent: May 7, 2013

(54) FGF MODULATION OF IN VIVO ANTIBODY PRODUCTION AND HUMORAL IMMUNITY

(76) Inventor: Andrew B. Bush, Princeton, NJ (US)

( * ) Notice: Subject to any disclaimer, the term of this patent is extended or adjusted under 35 U.S.C. 154(b) by 56 days.

(21) Appl. No.: 12/941,070

(22) Filed: Nov. 7, 2010

Related U.S. Application Data

(60) Provisional application No. 61/324,947, filed on Apr. 16, 2010.

(51) Int. Cl.
*A61K 39/395* (2006.01)
*C07K 16/22* (2006.01)
*C07K 14/50* (2006.01)

(52) U.S. Cl.
USPC .................. 424/158.1; 424/145.1; 424/184.1; 530/388.23; 530/389.2

(58) Field of Classification Search ........................ None
See application file for complete search history.

(56) References Cited

U.S. PATENT DOCUMENTS

| | | | | |
|---|---|---|---|---|
| 4,994,559 | A | 2/1991 | Moscatelli et al. | |
| 5,229,501 | A | 7/1993 | Keifer et al. | |
| 5,288,855 | A | 2/1994 | Bergonzoni et al. | |
| 5,440,021 | A | 8/1995 | Chuntharapai et al. | |
| 5,530,101 | A | 6/1996 | Queen et al. | |
| 5,707,632 | A | 1/1998 | Williams et al. | |
| 5,891,655 | A | 4/1999 | Ornitz | |
| 6,071,885 | A | 6/2000 | Florkiewicz | |
| 6,255,454 | B1 | 7/2001 | Keifer et al. | |
| 6,350,593 | B1 | 2/2002 | Williams et al. | |
| 6,900,053 | B2 | 5/2005 | Freier | |
| 2012/0214740 | A1* | 8/2012 | Imamura et al. | 514/9.1 |

FOREIGN PATENT DOCUMENTS

WO WO 03/072603 A2 * 9/2003

OTHER PUBLICATIONS

Camozzi et al. Pentraxin 3 inhibits fibroblast growth factor 2-dependent activation of smooth muscle cells in vitro and neointima formation in vivo. Arterioscler Thromb Vasc Biol. Sep. 2005;25(9):1837-42. Epub Jul. 14, 2005.*

Coffin et al. Abnormal bone growth and selective translational regulation in basic fibroblast growth factor (FGF-2)transgenic mice. Mol Biol Cell. Dec. 1995;6(12):1861-73.*

Firme et al. FGF signaling inhibits the proliferation of human myeloma cells and reduces c-myc expression. BMC Cell Biol. Dec. 4, 2003;4:17.*

Brasile et al. Bioengineered skin allografts: a new method to prevent humoral response. ASAIO J. May-Jun. 2011;57(3):239-43.*

Abraham et al., 1986. *Human basic fibroblast growth factor: nucleotide sequence and genomic organization*. Embo J 5:2523.

Bai et al., *GP369, an FGFR2-IIIb-specific antibody, exhibits potent antitumor activity against human cancers driven by activated FGFR2 signaling*. Cancer Res 2010 70 (19) 7630-9.

Brunner et al., 1993. *Basic fibroblast growth factor expression in human bone marrow and peripheral blood cells*. Blood 81:631.

Bryant et al., *Vascular remodeling in response to altered blood flow is mediated By fibroblast growth factor-2*. Circ Res, 1999, 84 (3) 323-8.

Chesi et al., *Frequent translocation t(4;14)(p16.3;q32.3) in multiple myeloma is associated with increased expression and activating mutations of fibroblast growth factor receptor 3*. Nature Genetics, 1997, 16 (3) 260-4.

Chou et al., 2003. *Bone marrow immunohistochemical studies of angiogenic cytokines and their receptors in myelofibrosis with myeloid metaplasia*. Leuk Res 27:499.

Coffin et al., 1995. *Abnormal bone growth and selective translational regulation in basic fibroblast growth factor (FGF-2) transgenic mice*. Mol Biol Cell 6:1861.

Dono et al., 1998. *Impaired cerebral cortex development and blood pressure regulation in FGF-2-deficient mice*. Embo J 17:4213.

Dutt et al., *Drug-sensitive FGFR2 mutations in endometrial carcinoma*. Proc Natl Acad Sci U S A. Jun. 24, 2008:105(25):8713-7.

Fagarasan et al., 2000. *T-Independent immune response: new aspects of B cell biology*. Science 290:89.

Guagnano et al, *Discovery of 3-(2,6-dichloro-3,5-dimethoxy-pheny1)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase*. J Med Chem. 2011, 54 (20) 7066-83.

Guagnano et al., *FGFR genetic alterations predict for sensitivity to NVP-BGJ398,a selective pan-FGFR inhibitor*. Cancer Discov. Sep. 20, 2012, CD-12-0210, Published Online.

Hori et al., *Suppression of solid tumor growth by immunoneutralizing monoclonal antibody against human basic fibroblast growth factor*. Cancer Res, 1991, 51 (22) 6180-4.

Karrer et al., 2000. *Antiviral B cell memory in the absence of mature follicular dendritic cell networks and classical germinal centers in TNFR1-/- mice*. J Immunol 164:768.

Keer et al. *Enrolling a rare patient population: Establishing proof of concept for FP-1039, an FGF "trap," in endometrial cancer patients with the S252W FGFR2 mutation*. J Clin Oncol 28: 15s, 2010, ASCO Annual Meeting 2010, Abstract TPS260.

MacLennan et al., 2003. *Extrafollicular antibody responses*. Immunol Rev 194:8.

Martin et al., 2001. *Marginal zone and B1 B cells unite in the early response against T-independent blood-borne particulate antigens*. Immunity 14:617.

Miller et al., 2000. *Compensation by fibroblast growth factor 1 (FGF1) does not account for the mild phenotypic defects observed in FGF2 null mice*. Mol Cell Biol 20:2260.

Ornitz et al., 1996. *Receptor specificity of the fibroblast growth factor family*. J Biol Chem 271:15292.

Ornitz et al., 2001. *Fibroblast growth factors*. Genome Biol 2.

Ortega et al., 1998. *Neuronal defects and delayed wound healing in mice lacking fibroblast growth factor 2*. Proc Natl Acad Sci U S A 95:5672.

Pasparakis et al., 1996. *Immune and inflammatory responses in TNF alpha-deficient mice: a critical requirement for TNF alpha in the formation of primary B cell follicles, follicular dendritic cell networks and germinal centers, and in the maturation of the humoral immune response*. J Exp Med 184:1397.

Qing et al., *Antibody-based targeting of FGFR3 in bladder carcinoma and t(4;14)-positive multiple myeloma in mice*. J Clin Invest. May 2009;119(5):1216-29.

Ravetch et al., 2000. *Immune inhibitory receptors*. Science 290:84.

Takai et al., 1996. *Augmented humoral and anaphylactic responses in Fc gamma RII-deficient mice*. Nature 379:346.

(Continued)

*Primary Examiner* — David Romeo

(74) *Attorney, Agent, or Firm* — Paul Diamond, Esq.; Diamond Law Office, LLC

(57) ABSTRACT

The invention provides methods for increasing or decreasing antibody production in vivo by inhibiting or promoting the activity of fibroblast growth factor-2 (FGF2) respectively.

4 Claims, 3 Drawing Sheets

OTHER PUBLICATIONS

Takeuchi et al., 1999. *Differential roles of TLR2 and TLR4 in recognition of gram-negative and gram-positive bacterial cell wall components*. Immunity 11:443.

Tolcher et al., 22nd EORTC-NCI-AACR Symposium on Molecular Targets and Cancer Therapeutics, Nov. 16-19, 2010 Berlin, Germany. *Preliminary Results of a Dose Escalation Study of the FGF "trap" FP-1039 (FGFR1:Fc) in Patients with Advanced Malignancies*.

Trudel et al.,*The inhibitory anti-FGFR3 antibody, PRO-001, is cytotoxic to t(4;14)multiple myeloma cells*. Blood. May 15, 2006;107(10):4039-46.

Wang et al., *A novel monoclonal antibody to fibroblast growth factor 2 effectively inhibits growth of hepatocellular carcinoma xenoqrafts*. Mol Cancer Ther. Apr. 2012; 11(4):864-72.

Wiedemann et al., 2000. *Characterization of a novel protein (FGFRL1) from human cartilage related to FGF receptors*. Genomics 69:275.

Yang et al., 1998. *Toll-like receptor-2 mediates lipopolysaccharide-induced cellular signalling*. Nature 395:284.

Zhou et al., 1998. *Fibroblast growth factor 2 control of vascular tone*. Nature Medicine 4:201.

* cited by examiner

SEQUENCE LISTING

```
<160> NUMBER OF SEQ ID NOS: 57

<210> SEQ ID NO 1
<211> LENGTH: 288
<212> TYPE: PRT
<213> ORGANISM: Homo sapiens

<400> SEQUENCE: 1

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220
```

```
Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285


<210> SEQ ID NO 2
<211> LENGTH: 6774
<212> TYPE: DNA
<213> ORGANISM: Homo sapiens

<400> SEQUENCE: 2

cggccccaga aaacccgagc gagtaggggg cggcgcgcag gagggaggag aactgggggc      60

gcgggaggct ggtgggtgtg gggggtggag atgtagaaga tgtgacgccg cggcccggcg     120

ggtgccagat tagcggacgc ggtgcccgcg gttgcaacgg gatcccgggc gctgcagctt     180

gggaggcggc tctccccagg cggcgtccgc ggagacaccc atccgtgaac cccaggtccc     240

gggccgccgg ctcgccgcgc accaggggcc ggcggacaga agagcggccg agcggctcga     300

ggctggggga ccgcgggcgc ggccgcgcgc tgccgggcgg gaggctgggg ggccggggcc     360

ggggccgtgc cccggagcgg gtcggaggcc ggggccgggg ccgggggacg gcggctcccc     420

gcgcggctcc agcggctcgg ggatcccggc cgggccccgc agggaccatg gcagccggga     480

gcatcaccac gctgcccgcc ttgcccgagg atggcggcag cggcgccttc ccgcccggcc     540

acttcaagga ccccaagcgg ctgtactgca aaaacggggg cttcttcctg cgcatccacc     600

ccgacggccg agttgacggg gtccgggaga agagcgaccc tcacatcaag ctacaacttc     660

aagcagaaga gagaggagtt gtgtctatca aaggagtgtg tgctaaccgt tacctggcta     720

tgaaggaaga tggaagatta ctggcttcta aatgtgttac ggatgagtgt ttctttttttg     780

aacgattgga atctaataac tacaatactt accggtcaag gaaatacacc agttggtatg     840

tggcactgaa acgaactggg cagtataaac ttggatccaa aacaggacct gggcagaaag     900

ctatactttt tcttccaatg tctgctaaga gctgatttta atggccacat ctaatctcat     960

ttcacatgaa agaagaagta tattttagaa atttgttaat gagagtaaaa gaaaataaat    1020

gtgtatagct cagtttggat aattggtcaa acaatttttt atccagtagt aaaatatgta    1080

accattgtcc cagtaaagaa aaataacaaa agttgtaaaa tgtatattct cccttttata    1140

ttgcatctgc tgttacccag tgaagcttac ctagagcaat gatcttttc acgcatttgc     1200

tttattcgaa aagaggcttt taaaatgtgc atgtttagaa acaaaatttc ttcatggaaa    1260

tcatatacat tagaaaatca cagtcagatg tttaatcaat ccaaaatgtc cactatttct    1320

tatgtcattc gttagtctac atgtttctaa acatataaat gtgaatttaa tcaattcctt    1380

tcatagtttt ataattctct ggcagttcct tatgatagag tttataaaac agtcctgtgt    1440

aaactgctgg aagttcttcc acagtcaggt caattttgtc aaacccttct ctgtacccat    1500

acagcagcag cctagcaact ctgctggtga tgggagttgt attttcagtc ttcgccaggt    1560

cattgagatc catccactca catcttaagc attcttcctg gcaaaaattt atggtgaatg    1620

aatatggctt taggcggcag atgatataca tatctgactt cccaaaagct ccaggatttg    1680

tgtgctgttg ccgaatactc aggacggacc tgaattctga ttttatacca gtctcttcaa    1740

aaacttctcg aaccgctgtg tctcctacgt aaaaaaagag atgtacaaat caataataat    1800
```

```
tacactttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatattttc ttaccactgt aaattcaaga agcttttgaa atgctgaata   1980
tttctttggc tgctacttgg aggcttatct acctgtacat tttggggtc agctcttttt    2040
aacttcttgc tgctcttttt cccaaaaggt aaaaatatag attgaaaagt taaaacattt   2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg atttttcaat taaatgcaaa   2280
tttgtgtggc aggattttta ttgccattaa catatttttg tggctgcttt ttctacacat   2340
ccagatggtc cctctaactg ggctttctct aattttgtga tgttctgtca ttgtctccca   2400
aagtatttag gagaagccct ttaaaaagct gccttcctct accactttgc tggaaagctt   2460
cacaattgtc acagacaaag atttttgttc caatactcgt tttgcctcta tttttcttgt   2520
ttgtcaaata gtaaatgata tttgcccttg cagtaattct actggtgaaa aacatgcaaa   2580
gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaaagtaa tttttactct gatgtgcaat   3180
acatttgtta ttaaatttat tatttaagat ggtagcacta gtcttaaatt gtataaaata   3240
tcccctaaca tgtttaaatg tccattttta ttcattatgc tttgaaaaat aattatgggg   3300
aaatacatgt ttgttattaa atttattatt aaagatagta gcactagtct taaatttgat   3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720
tgaaattttt aatcaagata gtgtgcttta ttctgttgta ttttttatta ttttaatata   3780
ctgtaagcca aactgaaata acatttgctg ttttataggt ttgaagaaca taggaaaaac   3840
taagaggttt tgtttttatt tttgctgatg aagagatatg tttaaatatg ttgtattgtt   3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgatttttt   4140
aagaaggcag tttgtcaatt ttaatcttgt ggataccttt atactcttag ggtattattt   4200
```

```
tatacaaaag ccttgaggat tgcattctat tttctatatg accctcttga tatttaaaaa   4260
acactatgga taacaattct tcatttacct agtattatga aagaatgaag gagttcaaac   4320
aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt ttcatttcta   4560
gctgctttca gggttttatg aattttcagg caaagcttta atttatacta agcttaggaa   4620
gtatggctaa tgccaacggc agtttttttc ttcttaattc cacatgactg aggcatatat   4680
gatctctggg taggtgagtt gttgtgacaa ccacaagcac tttttttttt tttaaagaaa   4740
aaaaggtagt gaatttttaa tcatctggac tttaagaagg attctggagt atacttaggc   4800
ctgaaattat atatatttgg cttggaaatg tgtttttctt caattacatc tacaagtaag   4860
tacagctgaa attcagagga cccataagag ttcacatgaa aaaaatcaat ttatttgaaa   4920
aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaact aagcaaaagg   5160
tcaataagta cctgaaacca agattggcta gagatatatc ttaatgcaat ccattttctg   5220
atggattgtt acgagttggc tatataatgt atgtatggta ttttgatttg tgtaaaagtt   5280
ttaaaaatca agctttaagt acatggacat ttttaaataa aatatttaaa gacaatttag   5340
aaaattgcct taatatcatt gttggctaaa tagaataggg gacatgcata ttaaggaaaa   5400
ggtcatggag aaataatatt ggtatcaaac aaatacattg atttgtcatg atacacattg   5460
aatttgatcc aatagtttaa ggaataggta ggaaaatttg gtttctattt ttcgatttcc   5520
tgtaaatcag tgacataaat aattcttagc ttattttata tttccttgtc ttaaatactg   5580
agctcagtaa gttgtgttag gggattattt ctcagttgag actttcttat atgacatttt   5640
actatgtttt gacttcctga ctattaaaaa taaatagtag atacaatttt cataaagtga   5700
agaattatat aatcactgct ttataactga ctttattata tttatttcaa agttcattta   5760
aaggctacta ttcatcctct gtgatggaat ggtcaggaat ttgttttctc atagtttaat   5820
tccaacaaca atattagtcg tatccaaaat aacctttaat gctaaacttt actgatgtat   5880
atccaaagct tctcattttc agacagatta atccagaagc agtcataaac agaagaatag   5940
gtggtatgtt cctaatgata ttatttctac taatggaata aactgtaata ttagaaatta   6000
tgctgctaat tatatcagct ctgaggtaat ttctgaaatg ttcagactca gtcggaacaa   6060
attggaaaat ttaaattttt attcttagct ataaagcaag aaagtaaaca cattaatttc   6120
ctcaacattt ttaagccaat taaaaatata aaagatacac accaatatct tcttcaggct   6180
ctgacaggcc tcctggaaac ttccacatat ttttcaactg cagtataaag tcagaaaata   6240
aagttaacat aactttcact aacacacaca tatgtagatt tcacaaaatc cacctataat   6300
tggtcaaagt ggttgagaat atattttta gtaattgcat gcaaaatttt tctagcttcc   6360
atcctttctc cctcgtttct tcttttttg ggggagctgg taactgatga aatcttttcc   6420
caccttttct cttcaggaaa tataagtggt tttgtttggt taacgtgata cattctgtat   6480
gaatgaaaca ttggagggaa acatctactg aatttctgta atttaaaata ttttgctgct   6540
agttaactat gaacagatag aagaatctta cagatgctgc tataaataag tagaaaatat   6600
```

```
aaatttcatc actaaaatat gctattttaa aatctatttc ctatattgta tttctaatca   6660

gatgtattac tcttattatt tctattgtat gtgttaatga ttttatgtaa aaatgtaatt   6720

gcttttcatg agtagtatga ataaaattga ttagtttgtg ttttcttgtc tccc         6774


<210> SEQ ID NO 3
<211> LENGTH: 733
<212> TYPE: PRT
<213> ORGANISM: Homo sapiens

<400> SEQUENCE: 3

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Asp Ser Ser Ser Glu
        35                  40                  45

Glu Lys Glu Thr Asp Asn Thr Lys Pro Asn Arg Met Pro Val Ala Pro
    50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
        115                 120                 125

Asp Ser Val Val Pro Ser Asp Lys Gly Asn Tyr Thr Cys Ile Val Glu
    130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
        195                 200                 205

Ser Lys Ile Gly Pro Asp Asn Leu Pro Tyr Val Gln Ile Leu Lys Thr
    210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255

Ser Ile Gly Leu Ser His His Ser Ala Trp Leu Thr Val Leu Glu Ala
            260                 265                 270

Leu Glu Glu Arg Pro Ala Val Met Thr Ser Pro Leu Tyr Leu Glu Ile
        275                 280                 285

Ile Ile Tyr Cys Thr Gly Ala Phe Leu Ile Ser Cys Met Val Gly Ser
    290                 295                 300

Val Ile Val Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ser Ala Ser Met Asn Ser Gly Val
            340                 345                 350
```

```
Leu Leu Val Arg Pro Ser Arg Leu Ser Ser Ser Gly Thr Pro Met Leu
        355                 360                 365

Ala Gly Val Ser Glu Tyr Glu Leu Pro Glu Asp Pro Arg Trp Glu Leu
    370                 375                 380

Pro Arg Asp Arg Leu Val Leu Gly Lys Pro Leu Gly Glu Gly Cys Phe
385                 390                 395                 400

Gly Gln Val Val Leu Ala Glu Ala Ile Gly Leu Asp Lys Asp Lys Pro
                405                 410                 415

Asn Arg Val Thr Lys Val Ala Val Lys Met Leu Lys Ser Asp Ala Thr
            420                 425                 430

Glu Lys Asp Leu Ser Asp Leu Ile Ser Glu Met Glu Met Met Lys Met
        435                 440                 445

Ile Gly Lys His Lys Asn Ile Ile Asn Leu Leu Gly Ala Cys Thr Gln
    450                 455                 460

Asp Gly Pro Leu Tyr Val Ile Val Glu Tyr Ala Ser Lys Gly Asn Leu
465                 470                 475                 480

Arg Glu Tyr Leu Gln Ala Arg Arg Pro Pro Gly Leu Glu Tyr Cys Tyr
                485                 490                 495

Asn Pro Ser His Asn Pro Glu Glu Gln Leu Ser Ser Lys Asp Leu Val
            500                 505                 510

Ser Cys Ala Tyr Gln Val Ala Arg Gly Met Glu Tyr Leu Ala Ser Lys
        515                 520                 525

Lys Cys Ile His Arg Asp Leu Ala Ala Arg Asn Val Leu Val Thr Glu
    530                 535                 540

Asp Asn Val Met Lys Ile Ala Asp Phe Gly Leu Ala Arg Asp Ile His
545                 550                 555                 560

His Ile Asp Tyr Tyr Lys Lys Thr Thr Asn Gly Arg Leu Pro Val Lys
                565                 570                 575

Trp Met Ala Pro Glu Ala Leu Phe Asp Arg Ile Tyr Thr His Gln Ser
            580                 585                 590

Asp Val Trp Ser Phe Gly Val Leu Leu Trp Glu Ile Phe Thr Leu Gly
        595                 600                 605

Gly Ser Pro Tyr Pro Gly Val Pro Val Glu Glu Leu Phe Lys Leu Leu
    610                 615                 620

Lys Glu Gly His Arg Met Asp Lys Pro Ser Asn Cys Thr Asn Glu Leu
625                 630                 635                 640

Tyr Met Met Met Arg Asp Cys Trp His Ala Val Pro Ser Gln Arg Pro
                645                 650                 655

Thr Phe Lys Gln Leu Val Glu Asp Leu Asp Arg Ile Val Ala Leu Thr
            660                 665                 670

Ser Asn Gln Glu Tyr Leu Asp Leu Ser Met Pro Leu Asp Gln Tyr Ser
        675                 680                 685

Pro Ser Phe Pro Asp Thr Arg Ser Ser Thr Cys Ser Ser Gly Glu Asp
    690                 695                 700

Ser Val Phe Ser His Glu Pro Leu Pro Glu Glu Pro Cys Leu Pro Arg
705                 710                 715                 720

His Pro Ala Gln Leu Ala Asn Gly Gly Leu Lys Arg Arg
                725                 730
```

<210> SEQ ID NO 4
<211> LENGTH: 3365
<212> TYPE: DNA
<213> ORGANISM: Homo sapiens

<400> SEQUENCE: 4

-continued

```
gcaccgagcg ccgccgggag tcgagcgccg gccgcggagc tcttgcgacc ccgccaggac     60
ccgaacagag cccgggggcg gcgggccgga gccggggacg cgggcacacg cccgctcgca    120
caagccacgg cggactctcc cgaggcggaa cctccacgcc gagcgagggt cagtttgaaa    180
aggaggatcg agctcactgt ggagtatcca tggagatgtg gagccttgtc accaacctct    240
aactgcagaa ctgggatgtg gagctggaag tgcctcctct tctgggctgt gctggtcaca    300
gccacactct gcaccgctag gccgtccccg accttgcctg aacaagatgc tctcccctcc    360
tcggaggatg atgatgatga tgatgactcc tcttcagagg agaaagaaac agataacacc    420
aaaccaaacc gtatgcccgt agctccatat tggacatccc cagaaaagat ggaaaagaaa    480
ttgcatgcag tgccggctgc caagacagtg aagttcaaat gcccttccag tgggacccca    540
aaccccacac tgcgctggtt gaaaaatggc aaagaattca aacctgacca cagaattgga    600
ggctacaagg tccgttatgc cacctggagc atcataatgg actctgtggt gccctctgac    660
aagggcaact acacctgcat tgtggagaat gagtacggca gcatcaacca cacataccag    720
ctggatgtcg tggagcggtc ccctcaccgg cccatcctgc aagcagggtt gcccgccaac    780
aaaacagtgg ccctgggtag caacgtggag ttcatgtgta aggtgtacag tgacccgcag    840
ccgcacatcc agtggctaaa gcacatcgag gtgaatggga gcaagattgg cccagacaac    900
ctgccttatg tccagatctt gaagactgct ggagttaata ccaccgacaa agagatggag    960
gtgcttcact taagaaatgt ctcctttgag gacgcagggg agtatacgtg cttggcgggt   1020
aactctatcg gactctccca tcactctgca tggttgaccg ttctggaagc cctggaagag   1080
aggccggcag tgatgacctc gcccctgtac ctggagatca tcatctattg cacaggggcc   1140
ttcctcatct cctgcatggt ggggtcggtc atcgtctaca agatgaagag tggtaccaag   1200
aagagtgact tccacagcca gatggctgtg cacaagctgg ccaagagcat ccctctgcgc   1260
agacaggtaa cagtgtctgc tgactccagt gcatccatga actctggggt tcttctggtt   1320
cggccatcac ggctctcctc cagtgggact cccatgctag caggggtctc tgagtatgag   1380
cttcccgaag accctcgctg ggagctgcct cgggacagac tggtcttagg caaacccctg   1440
ggagagggct gctttgggca ggtggtgttg gcagaggcta tcgggctgga caaggacaaa   1500
cccaaccgtg tgaccaaagt ggctgtgaag atgttgaagt cggacgcaac agagaaagac   1560
ttgtcagacc tgatctcaga aatggagatg atgaagatga tcgggaagca taagaatatc   1620
atcaacctgc tgggggcctg cacgcaggat ggtcccttgt atgtcatcgt ggagtatgcc   1680
tccaagggca acctgcggga gtacctgcag gcccggaggc ccccagggct ggaatactgc   1740
tacaacccca gccacaaccc agaggagcag ctctcctcca aggacctggt gtcctgcgcc   1800
taccaggtgg cccgaggcat ggagtatctg gcctccaaga agtgcataca ccgagacctg   1860
gcagccagga atgtcctggt gacagaggac aatgtgatga agatagcaga ctttggcctc   1920
gcacgggaca ttcaccacat cgactactat aaaaagacaa ccaacggccg actgcctgtg   1980
aagtggatgg cacccgaggc attatttgac cggatctaca cccaccagag tgatgtgtgg   2040
tctttcgggg tgctcctgtg ggagatcttc actctgggcg gctccccata ccccggtgtg   2100
cctgtggagg aacttttcaa gctgctgaag gagggtcacc gcatggacaa gcccagtaac   2160
tgcaccaacg agctgtacat gatgatgcgg gactgctggc atgcagtgcc ctcacagaga   2220
cccaccttca agcagctggt ggaagacctg gaccgcatcg tggccttgac ctccaaccag   2280
gagtacctgg acctgtccat gcccctggac cagtactccc ccagctttcc cgacacccgg   2340
agctctacgt gctcctcagg ggaggattcc gtcttctctc atgagccgct gcccgaggag   2400
```

```
ccctgcctgc cccgacaccc agcccagctt gccaatggcg gactcaaacg ccgctgactg   2460

ccacccacac gccctcccca gactccaccg tcagctgtaa ccctcaccca cagcccctgc   2520

tgggcccacc acctgtccgt ccctgtcccc tttcctgctg gcaggagccg gctgcctacc   2580

aggggccttc ctgtgtggcc tgccttcacc ccactcagct cacctctccc tccacctcct   2640

ctccacctgc tggtgagagg tggcaaagag gcagatcttt gctgccagcc acttcatccc   2700

ctcccagatg ttggaccaac acccctccct gccaccaggc actgcctgga gggcagggag   2760

tgggagccaa tgaacaggca tgcaagtgag agcttcctga gctttctcct gtcggtttgg   2820

tctgttttgc cttcacccat aagcccctcg cactctggtg gcaggtgcct tgtcctcagg   2880

gctacagcag tagggaggtc agtgcttcgt gcctcgattg aaggtgacct ctgccccaga   2940

taggtggtgc cagtggctta ttaattccga tactagtttg ctttgctgac caaatgcctg   3000

gtaccagagg atggtgaggc gaaggccagg ttgggggcag tgttgtggcc ctggggccca   3060

gccccaaact gggggctctg tatatagcta tgaagaaaac acaaagtgta taaatctgag   3120

tatatattta catgtctttt taaaagggtc gttaccagag atttacccat cgggtaagat   3180

gctcctggtg gctgggaggc atcagttgct atatattaaa aacaaaaaag aaaaaaaagg   3240

aaaacgtttt taaaaaggtc atatattttt tgctactttt gctgttttat ttttttaaat   3300

tatgttctaa acctattttc agtttaggtc cctcaataaa aattgctgct gcttcaaaaa   3360

aaaaa                                                               3365
```

<210> SEQ ID NO 5
<211> LENGTH: 821
<212> TYPE: PRT
<213> ORGANISM: Homo sapiens

<400> SEQUENCE: 5

```
Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
```

```
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
        595                 600                 605

Gln Leu Ala Arg Gly Met Glu Tyr Leu Ala Ser Gln Lys Cys Ile His
    610                 615                 620
```

```
Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
        675                 680                 685

Phe Gly Val Leu Met Trp Glu Ile Phe Thr Leu Gly Gly Ser Pro Tyr
    690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820
```

<210> SEQ ID NO 6
<211> LENGTH: 4654
<212> TYPE: DNA
<213> ORGANISM: Homo sapiens

<400> SEQUENCE: 6

```
ggcggcggct ggaggagagc gcggtggaga gccgagcggg cgggcggcgg gtgcggagcg      60

ggcgagggag cgcgcgcggc cgccacaaag ctcgggcgcc gcggggctgc atgcggcgta     120

cctggcccgg cgcggcgact gctctccggg ctggcggggg ccggccgcga gccccggggg     180

ccccgaggcc gcagcttgcc tgcgcgctct gagccttcgc aactcgcgag caaagtttgg     240

tggaggcaac gccaagcctg agtcctttct tcctctcgtt ccccaaatcc gagggcagcc     300

cgcgggcgtc atgcccgcgc tcctccgcag cctggggtac gcgtgaagcc cgggaggctt     360

ggcgccggcg aagacccaag gaccactctt ctgcgtttgg agttgctccc cgcaaccccg     420

ggctcgtcgc tttctccatc ccgacccacg cggggcgcgg ggacaacaca ggtcgcggag     480

gagcgttgcc attcaagtga ctgcagcagc agcggcagcg cctcggttcc tgagcccacc     540

gcaggctgaa ggcattgcgc gtagtccatg cccgtagagg aagtgtgcag atgggattaa     600

cgtccacatg gagatatgga agaggaccgg ggattggtac cgtaaccatg gtcagctggg     660

gtcgtttcat ctgcctggtc gtggtcacca tggcaacctt gtccctggcc cggccctcct     720

tcagtttagt tgaggatacc acattagagc cagaagagcc accaaccaaa taccaaatct     780

ctcaaccaga agtgtacgtg gctgcgccag gggagtcgct agaggtgcgc tgcctgttga     840

aagatgccgc cgtgatcagt tggactaagg atggggtgca cttggggccc aacaatagga     900

cagtgcttat tggggagtac ttgcagataa agggcgccac gcctagagac tccggcctct     960

atgcttgtac tgccagtagg actgtagaca gtgaaacttg gtacttcatg gtgaatgtca    1020
```

```
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc gggggggaacc   1200
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaaggccg ccggtgttaa caccacggac aaagagattg   1620
aggttctcta tattcggaat gtaacttttg aggacgctgg ggaatatacg tgcttggcgg   1680
gtaattctat tgggatatcc tttcactctg catggttgac agttctgcca gcgcctggaa   1740
gagaaaagga gattacagct tccccagact acctggagat agccatttac tgcatagggg   1800
tcttcttaat cgcctgtatg gtggtaacag tcatcctgtg ccgaatgaag aacacgacca   1860
agaagccaga cttcagcagc cagccggctg tgcacaagct gaccaaacgt atccccctgc   1920
ggagacaggt aacagtttcg gctgagtcca gctcctccat gaactccaac accccgctgg   1980
tgaggataac aacacgcctc tcttcaacgg cagacacccc catgctggca ggggtctccg   2040
agtatgaact tccagaggac ccaaaatggg agtttccaag agataagctg acactgggca   2100
agcccctggg agaaggttgc tttgggcaag tggtcatggc ggaagcagtg ggaattgaca   2160
aagacaagcc caaggaggcg gtcaccgtgg ccgtgaagat gttgaaagat gatgccacag   2220
agaaagacct ttctgatctg gtgtcagaga tggagatgat gaagatgatt gggaaacaca   2280
agaatatcat aaatcttctt ggagcctgca cacaggatgg gcctctctat gtcatagttg   2340
agtatgcctc taaaggcaac ctccgagaat acctccgagc ccggaggcca cccgggatgg   2400
agtactccta tgacattaac cgtgttcctg aggagcagat gaccttcaag gacttggtgt   2460
catgcaccta ccagctggcc agaggcatgg agtacttggc ttcccaaaaa tgtattcatc   2520
gagatttagc agccagaaat gttttggtaa cagaaaacaa tgtgatgaaa atagcagact   2580
ttggactcgc cagagatatc aacaatatag actattacaa aaagaccacc aatgggcggc   2640
ttccagtcaa gtggatggct ccagaagccc tgtttgatag agtatacact catcagagtg   2700
atgtctggtc cttcggggtg ttaatgtggg agatcttcac tttagggggc tcgccctacc   2760
cagggattcc cgtggaggaa ctttttaagc tgctgaagga aggacacaga atggataagc   2820
cagccaactg caccaacgaa ctgtacatga tgatgaggga ctgttggcat gcagtgccct   2880
cccagagacc aacgttcaag cagttggtag aagacttgga tcgaattctc actctcacaa   2940
ccaatgagga atacttggac ctcagccaac ctctcgaaca gtattcacct agttaccctg   3000
acacaagaag ttcttgttct tcaggagatg attctgtttt ttctccagac cccatgcctt   3060
acgaaccatg ccttcctcag tatccacaca taaacggcag tgttaaaaca tgaatgactg   3120
tgtctgcctg tccccaaaca ggacagcact gggaacctag ctacactgag cagggagacc   3180
atgcctccca gagcttgttg tctccacttg tatatatgga tcagaggagt aaataattgg   3240
aaaagtaatc agcatatgtg taaagattta tacagttgaa aacttgtaat cttccccagg   3300
aggagaagaa ggtttctgga gcagtggact gccacaagcc accatgtaac cctctcacc   3360
tgccgtgcgt actggctgtg gaccagtagg actcaaggtg gacgtgcgtt ctgccttcct   3420
```

```
tgttaatttt gtaataattg gagaagattt atgtcagcac acacttacag agcacaaatg   3480

cagtatatag gtgctggatg tatgtaaata tattcaaatt atgtataaat atatattata   3540

tatttacaag gagttatttt ttgtattgat tttaaatgga tgtcccaatg cacctagaaa   3600

attggtctct cttttttttaa tagctatttg ctaaatgctg ttcttacaca taatttctta   3660

attttcaccg agcagaggtg gaaaaatact tttgctttca gggaaaatgg tataacgtta   3720

atttattaat aaattggtaa tatacaaaac aattaatcat ttatagtttt ttttgtaatt   3780

taagtggcat ttctatgcag gcagcacagc agactagtta atctattgct tggacttaac   3840

tagttatcag atcctttgaa aagagaatat ttacaatata tgactaattt ggggaaaatg   3900

aagttttgat ttatttgtgt ttaaatgctg ctgtcagacg attgttctta gacctcctaa   3960

atgccccata ttaaaagaac tcattcatag gaaggtgttt cattttggtg tgcaaccctg   4020

tcattacgtc aacgcaacgt ctaactggac ttcccaagat aaatggtacc agcgtcctct   4080

taaaagatgc cttaatccat tccttgagga cagaccttag ttgaaatgat agcagaatgt   4140

gcttctctct ggcagctggc cttctgcttc tgagttgcac attaatcaga ttagcctgta   4200

ttctcttcag tgaattttga taatggcttc cagactcttt ggcgttggag acgcctgtta   4260

ggatcttcaa gtcccatcat agaaaattga aacacagagt tgttctgctg atagttttgg   4320

ggatacgtcc atctttttaa gggattgctt tcatctaatt ctggcaggac ctcaccaaaa   4380

gatccagcct catacctaca tcagacaaaa tatcgccgtt gttccttctg tactaaagta   4440

ttgtgttttg ctttggaaac acccactcac tttgcaatag ccgtgcaaga tgaatgcaga   4500

ttacactgat cttatgtgtt acaaaattgg agaaagtatt taataaaacc tgttaatttt   4560

tatactgaca ataaaaatgt ttctacagat attaatgtta acaagacaaa ataaatgtca   4620

cgcaacttat ttttttaata aaaaaaaaaa aaaa                               4654
```

```
<210> SEQ ID NO 7
<211> LENGTH: 806
<212> TYPE: PRT
<213> ORGANISM: Homo sapiens

<400> SEQUENCE: 7

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160
```

```
Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
```

```
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805


<210> SEQ ID NO 8
<211> LENGTH: 4304
<212> TYPE: DNA
<213> ORGANISM: Homo sapiens

<400> SEQUENCE: 8

gtcgcgggca gctggcgccg cgcggtcctg ctctgccggt cgcacggacg caccggcggg      60

ccgccggccg gagggacggg gcgggagctg ggcccgcgga cagcgagccg gagcgggagc     120

cgcgcgtagc gagccgggct ccggcgctcg ccagtctccc gagcggcgcc cgcctcccgc     180

cggtgcccgc gccgggccgt ggggggcagc atgcccgcgc gcgctgcctg aggacgccgc     240

ggcccccgcc cccgccatgg gcgcccctgc ctgcgccctc gcgctctgcg tggccgtggc     300

catcgtggcc ggcgcctcct cggagtcctt ggggacggag cagcgcgtcg tggggcgagc     360

ggcagaagtc ccgggcccag agcccggcca gcaggagcag ttggtcttcg gcagcgggga     420

tgctgtggag ctgagctgtc ccccgcccgg gggtggtccc atggggccca ctgtctgggt     480

caaggatggc acagggctgg tgccctcgga gcgtgtcctg gtggggcccc agcggctgca     540

ggtgctgaat gcctcccacg aggactccgg ggcctacagc tgccggcagc ggctcacgca     600

gcgcgtactg tgccacttca gtgtgcgggt gacagacgct ccatcctcgg gagatgacga     660

agacggggag gacgaggctg aggacacagg tgtggacaca ggggcccctt actggacacg     720

gcccgagcgg atggacaaga agctgctggc cgtgccggcc gccaacaccg tccgcttccg     780

ctgcccagcc gctggcaacc ccactccctc catctcctgg ctgaagaacg gcagggagtt     840
```

```
ccgcggcgag caccgcattg gaggcatcaa gctgcggcat cagcagtgga gcctggtcat    900
ggaaagcgtg gtgccctcgg accgcggcaa ctacacctgc gtcgtggaga acaagtttgg    960
cagcatccgg cagacgtaca cgctggacgt gctggagcgc tccccgcacc ggcccatcct   1020
gcaggcgggg ctgccggcca accagacggc ggtgctgggc agcgacgtgg agttccactg   1080
caaggtgtac agtgacgcac agccccacat ccagtggctc aagcacgtgg aggtgaatgg   1140
cagcaaggtg ggcccggacg gcacacccta cgttaccgtg ctcaagacgg cgggcgctaa   1200
caccaccgac aaggagctag aggttctctc cttgcacaac gtcacctttg aggacgccgg   1260
ggagtacacc tgcctggcgg gcaattctat tgggttttct catcactctg cgtggctggt   1320
ggtgctgcca gccgaggagg agctggtgga ggctgacgag gcgggcagtg tgtatgcagg   1380
catcctcagc tacggggtgg gcttcttcct gttcatcctg gtggtggcgg ctgtgacgct   1440
ctgccgcctg cgcagccccc ccaagaaagg cctgggctcc cccaccgtgc acaagatctc   1500
ccgcttcccg ctcaagcgac aggtgtccct ggagtccaac gcgtccatga gctccaacac   1560
accactggtg cgcatcgcaa ggctgtcctc aggggagggc cccacgctgg ccaatgtctc   1620
cgagctcgag ctgcctgccg accccaaatg ggagctgtct cgggcccggc tgaccctggg   1680
caagcccctt ggggagggct gcttcggcca ggtggtcatg gcggaggcca tcggcattga   1740
caaggaccgg gccgccaagc ctgtcaccgt agccgtgaag atgctgaaag acgatgccac   1800
tgacaaggac ctgtcggacc tggtgtctga gatggagatg atgaagatga tcgggaaaca   1860
caaaaacatc atcaacctgc tgggcgcctg cacgcagggc gggcccctgt acgtgctggt   1920
ggagtacgcg gccaagggta acctgcggga gtttctgcgg gcgcggcggc ccccgggcct   1980
ggactactcc ttcgacacct gcaagccgcc cgaggagcag ctcaccttca aggacctggt   2040
gtcctgtgcc taccaggtgg cccggggcat ggagtacttg gcctcccaga agtgcatcca   2100
cagggacctg gctgcccgca atgtgctggt gaccgaggac aacgtgatga agatcgcaga   2160
cttcgggctg gcccgggacg tgcacaacct cgactactac aagaagacaa ccaacggccg   2220
gctgcccgtg aagtggatgg cgcctgaggc cttgtttgac cgagtctaca ctcaccagag   2280
tgacgtctgg tcctttgggg tcctgctctg ggagatcttc acgctggggg gctccccgta   2340
ccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca agcagctggt ggaggacctg gaccgtgtcc ttaccgtgac   2520
gtccaccgac gagtacctgg acctgtcggc gcctttcgag cagtactccc cgggtggcca   2580
ggacaccccc agctccagct cctcagggga cgactccgtg tttgcccacg acctgctgcc   2640
cccggcccca cccagcagtg gggctcgcg gacgtgaagg gccactggtc cccaacaatg   2700
tgaggggtcc ctagcagccc accctgctgc tggtgcacag ccactccccg gcatgagact   2760
cagtgcagat ggagagacag ctacacagag ctttggtctg tgtgtgtgtg tgtgcgtgtg   2820
tgtgtgtgtg tgtgcacatc cgcgtgtgcc tgtgtgcgtg cgcatcttgc ctccaggtgc   2880
agaggtaccc tgggtgtccc cgctgctgtg caacggtctc ctgactggtg ctgcagcacc   2940
gaggggcctt tgttctgggg ggacccagtg cagaatgtaa gtgggcccac ccggtgggac   3000
ccccgtgggg cagggagctg ggcccgacat ggctccggcc tctgcctttg caccacggga   3060
catcacaggg tgggcctcgg cccctcccac acccaaagct gagcctgcag ggaagcccca   3120
catgtccagc accttgtgcc tggggtgtta gtggcaccgc ctccccacct ccaggctttc   3180
ccacttccca ccctgcccct cagagactga aattacgggt acctgaagat gggagccttt   3240
```

```
accttttatg caaaaggttt attccggaaa ctagtgtaca tttctataaa tagatgctgt   3300

gtatatggta tatatacata tatatatata acatatatgg aagaggaaaa ggctggtaca   3360

acggaggcct gcgaccctgg gggcacagga ggcaggcatg gccctgggcg gggcgtgggg   3420

gggcgtggag ggaggcccca gggggtctca cccatgcaag cagaggacca gggccttttc   3480

tggcaccgca gttttgtttt aaaactggac ctgtatattt gtaaagctat ttatgggccc   3540

ctggcactct tgttcccaca ccccaacact tccagcattt agctggccac atggcggaga   3600

gttttaattt ttaacttatt gacaaccgag aaggtttatc ccgccgatag agggacggcc   3660

aagaatgtac gtccagcctg ccccggagct ggaggatccc ctccaagcct aaaaggttgt   3720

taatagttgg aggtgattcc agtgaagata ttttatttcc tttgtccttt ttcaggagaa   3780

ttagatttct ataggatttt tctttaggag atttattttt tggacttcaa agcaagctgg   3840

tattttcata caaattcttc taattgctgt gtgtcccagg cagggagacg gtttccaggg   3900

aggggccggc cctgtgtgca ggttccgatg ttattagatg ttacaagttt atatatatct   3960

atatatataa tttattgagt ttttacaaga tgtatttgtt gtagacttaa cacttcttac   4020

gcaatgcttc tagagtttta tagcctggac tgctaccttt caaagcttgg agggaagccg   4080

tgaattcagt tggttcgttc tgtactgtta ctgggccctg agtctgggca gctgtccctt   4140

gcttgcctgc agggccatgg ctcagggtgg tctcttcttg ggcccagtg catggtggcc   4200

agaggtgtca cccaaaccgg caggtgcgat tttgttaacc cagcgacgaa ctttccgaaa   4260

aataaagaca cctggttgct aacctggaaa aaaaaaaaaa aaaa                    4304
```

<210> SEQ ID NO 9
<211> LENGTH: 762
<212> TYPE: PRT
<213> ORGANISM: Homo sapiens

<400> SEQUENCE: 9

```
Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Ser Thr Ser Ser Asn Asp Asp Glu
        115                 120                 125

Asp Pro Lys Ser His Arg Asp Leu Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190
```

```
Gly Gly Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Gly Thr Gly Arg Ile Pro His Leu Thr Cys Asp Ser Leu Thr Pro Ala
        355                 360                 365

Gly Arg Thr Lys Ser Pro Thr Leu Gln Phe Ser Leu Glu Ser Gly Ser
    370                 375                 380

Ser Gly Lys Ser Ser Ser Ser Leu Val Arg Gly Val Arg Leu Ser Ser
385                 390                 395                 400

Ser Gly Pro Ala Leu Leu Ala Gly Leu Val Ser Leu Asp Leu Pro Leu
                405                 410                 415

Asp Pro Leu Trp Glu Phe Pro Arg Asp Arg Leu Val Leu Gly Lys Pro
            420                 425                 430

Leu Gly Glu Gly Cys Phe Gly Gln Val Val Arg Ala Glu Ala Phe Gly
        435                 440                 445

Met Asp Pro Ala Arg Pro Asp Gln Ala Ser Thr Val Ala Val Lys Met
    450                 455                 460

Leu Lys Asp Asn Ala Ser Asp Lys Asp Leu Ala Asp Leu Val Ser Glu
465                 470                 475                 480

Met Glu Val Met Lys Leu Ile Gly Arg His Lys Asn Ile Ile Asn Leu
                485                 490                 495

Leu Gly Val Cys Thr Gln Glu Gly Pro Leu Tyr Val Ile Val Glu Cys
            500                 505                 510

Ala Ala Lys Gly Asn Leu Arg Glu Phe Leu Arg Ala Arg Arg Pro Pro
        515                 520                 525

Gly Pro Asp Leu Ser Pro Asp Gly Pro Arg Ser Ser Glu Gly Pro Leu
    530                 535                 540

Ser Phe Pro Val Leu Val Ser Cys Ala Tyr Gln Val Ala Arg Gly Met
545                 550                 555                 560

Gln Tyr Leu Glu Ser Arg Lys Cys Ile His Arg Asp Leu Ala Ala Arg
                565                 570                 575

Asn Val Leu Val Thr Glu Asp Asn Val Met Lys Ile Ala Asp Phe Gly
            580                 585                 590

Leu Ala Arg Gly Val His His Ile Asp Tyr Tyr Lys Lys Thr Ser Asn
        595                 600                 605

Gly Arg Leu Pro Val Lys Trp Met Ala Pro Glu Ala Leu Phe Asp Arg
    610                 615                 620
```

```
Val Tyr Thr His Gln Ser Asp Val Trp Ser Phe Gly Ile Leu Leu Trp
625                 630                 635                 640

Glu Ile Phe Thr Leu Gly Gly Ser Pro Tyr Pro Gly Ile Pro Val Glu
                645                 650                 655

Glu Leu Phe Ser Leu Leu Arg Glu Gly His Arg Met Asp Arg Pro Pro
            660                 665                 670

His Cys Pro Pro Glu Leu Tyr Gly Leu Met Arg Glu Cys Trp His Ala
        675                 680                 685

Ala Pro Ser Gln Arg Pro Thr Phe Lys Gln Leu Val Glu Ala Leu Asp
    690                 695                 700

Lys Val Leu Leu Ala Val Ser Glu Glu Tyr Leu Asp Leu Arg Leu Thr
705                 710                 715                 720

Phe Gly Pro Tyr Ser Pro Ser Gly Gly Asp Ala Ser Ser Thr Cys Ser
                725                 730                 735

Ser Ser Asp Ser Val Phe Ser His Asp Pro Leu Pro Leu Gly Ser Ser
            740                 745                 750

Ser Phe Pro Phe Gly Ser Gly Val Gln Thr
        755                 760
```

<210> SEQ ID NO 10
<211> LENGTH: 2418
<212> TYPE: DNA
<213> ORGANISM: Homo sapiens

<400> SEQUENCE: 10

```
agtccagctt gggtccctga gagctgtgag aaggagatgc ggctgctgct ggccctgttg     60

ggggtcctgc tgagtgtgcc tgggcctcca gtcttgtccc tggaggcctc tgaggaagtg    120

gagcttgagc cctgcctggc tcccagcctg gagcagcaag agcaggagct gacagtagcc    180

cttgggcagc ctgtgcggct gtgctgtggg cgggctgagc gtggtggcca ctggtacaag    240

gagggcagtc gcctggcacc tgctggccgt gtacggggct ggaggggccg cctagagatt    300

gccagcttcc tacctgagga tgctggccgc tacctctgcc tggcacgagg ctccatgatc    360

gtcctgcaga atctcacctt gattacaggt gactcctcga cctccagcaa cgatgatgag    420

gaccccaagt cccataggga cctctcgaat aggcacagtt acccccagca agcaccctac    480

tggacacacc cccagcgcat ggagaagaaa ctgcatgcag tacctgcggg gaacaccgtc    540

aagttccgct gtccagctgc aggcaacccc acgcccacca tccgctggct taaggatgga    600

caggcctttc atgggggaa ccgcattgga ggcattcggc tgcgccatca gcactggagt     660

ctcgtgatgg agagcgtggt gccctcggac cgcggcacat acacctgcct ggtagagaac    720

gctgtgggca gcatccgtta taactacctg ctagatgtgc tggagcggtc cccgcaccgg    780

cccatcctgc aggccgggct cccggccaac accacagccg tggtgggcag cgacgtggag    840

ctgctgtgca aggtgtacag cgatgcccag ccccacatcc agtggctgaa gcacatcgtc    900

atcaacggca gcagcttcgg agccgacggt ttcccctatg tgcaagtcct aaagactgca    960

gacatcaata gctcagaggt ggaggtcctg tacctgcgga acgtgtcagc cgaggacgca   1020

ggcgagtaca cctgcctcgc aggcaattcc atcggcctct cctaccagtc tgcctggctc   1080

acggtgctgc caggtactgg gcgcatcccc cacctcacat gtgacagcct gactccagca   1140

ggcagaacca agtctcccac tttgcagttc tccctggagt caggctcctc cggcaagtca   1200

agctcatccc tggtacgagg cgtgcgtctc tcctccagcg gccccgcctt gctcgccggc   1260

ctcgtgagtc tagatctacc tctcgaccca ctatgggagt tcccccggga caggctggtg   1320
```

```
cttgggaagc ccctaggcga gggctgcttt ggccaggtag tacgtgcaga ggcctttggc   1380

atggaccctg cccggcctga ccaagccagc actgtggccg tcaagatgct caaagacaac   1440

gcctctgaca aggacctggc cgacctggtc tcggagatgg aggtgatgaa gctgatcggc   1500

cgacacaaga acatcatcaa cctgcttggt gtctgcaccc aggaagggcc cctgtacgtg   1560

atcgtggagt gcgccgccaa gggaaacctg cgggagttcc tgcgggcccg gcgcccccca   1620

ggccccgacc tcagccccga cggtcctcgg agcagtgagg ggccgctctc cttcccagtc   1680

ctggtctcct gcgcctacca ggtggcccga ggcatgcagt atctggagtc ccggaagtgt   1740

atccaccggg acctggctgc ccgcaatgtg ctggtgactg aggacaatgt gatgaagatt   1800

gctgactttg ggctggcccg cggcgtccac cacattgact actataagaa aaccagcaac   1860

ggccgcctgc ctgtgaagtg gatggcgccc gaggccttgt ttgaccgggt gtacacacac   1920

cagagtgacg tgtggtcttt tgggatcctg ctatgggaga tcttcaccct cgggggctcc   1980

ccgtatcctg gcatcccggt ggaggagctg ttctcgctgc tgcgggaggg acatcggatg   2040

gaccgacccc cacactgccc cccagagctg tacgggctga tgcgtgagtg ctggcacgca   2100

gcgccctccc agaggcctac cttcaagcag ctggtggagg cgctggacaa ggtcctgctg   2160

gccgtctctg aggagtacct cgacctccgc ctgaccttcg gaccctattc cccctctggt   2220

ggggacgcca gcagcacctg ctcctccagc gattctgtct tcagccacga cccccctgcca   2280

ttgggatcca gctccttccc cttcgggtct ggggtgcaga catgagcaag gctcaaggct   2340

gtgcaggcac ataggctggt ggccttgggc cttggggctc agccacagcc tgacacagtg   2400

ctcgaccttg atagcatg                                                 2418
```

<210> SEQ ID NO 11
<211> LENGTH: 155
<212> TYPE: PRT
<213> ORGANISM: Bos taurus

<400> SEQUENCE: 11

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155
```

<210> SEQ ID NO 12
<211> LENGTH: 6601
<212> TYPE: DNA

<213> ORGANISM: Bos taurus

<400> SEQUENCE: 12

```
ccggggccgc gccgcggagc gcgtcggagg ccggggccgg ggcgcggcgg ctccccgcgc     60
ggctccaggg gctcggggac cccgccaggg ccttggtggg gccatggccg ccgggagcat    120
caccacgctg ccagccctgc cggaggacgg cggcagcggc gctttcccgc cgggccactt    180
caaggacccc aagcggctgt actgcaagaa cgggggcttc ttcctgcgca tccaccccga    240
cggccgagtg gacggggtcc gcgagaagag cgacccacac atcaaactac aacttcaagc    300
agaagagaga ggggttgtgt ctatcaaagg agtgtgtgca aaccgttacc ttgctatgaa    360
agaagatgga agattactag cttctaaatg tgttacagac gagtgtttct tttttgaacg    420
attggagtct aataactaca atacttaccg gtcaaggaaa tactccagtt ggtatgtggc    480
actgaaacga actgggcagt ataaacttgg acccaaaaca ggacctgggc agaaagctat    540
actttttctt ccaatgtctg ctaagagctg atcttaatgg cagcatctga tctcatttta    600
catgaagagg tatatttcag aaatgtgtta atgaaaaaag aaaaatgtgt acagtgagct    660
gctcagtttg ggtaactgtt cagataaccg tttatctaag agtaaaatat ttaaccattg    720
ccttagtttt tttttaaaga aaaaacacaa taacagcaaa aattcctgga aaatgtatac    780
atttccactt tttatacagc atttcctttt atccagtgaa acttacttaa agctacaatc    840
tttcatacag ttgcttcatt tgaagaggct tttaaaatgt gtacaaacaa gttttcttca    900
tggaaattat agacattaga aaattaaagt catatttagt tattaaccca aatgtccact    960
acttcctata atatggcaca cattaatcta catgtacaac ttacttaaac atgtacaact   1020
tacttaaaca ttttaaaaac atgtaaatat gaatttaatc cattcctgtc atagttttgt   1080
aattgtctgg cagtttcttg tgatagagtt tatagaacaa gcctgtgtaa actgctggca   1140
gttcttccat ggtcagatca attttgtcaa acccttcttt gtacccatac agcagcagcc   1200
ttgcaactct gcttgttatg ggagtcgtat ttttagtctt gactagatcg ctgagattca   1260
tccactcaca ctttaagcat tcacgctggc aaaaatttat ggtgaatgaa tatggcttta   1320
agcggcagat aatatacata tctgacttcc caaaagctcc tggatgggtg tgctgttgcc   1380
gaatactcag gagggatctg aattcggatt ttataccagt ctcttcaaaa acttctcgaa   1440
ctgctgtatc tcctacataa aagaaaatgt acaaatcaat aacgattata cttttagaaa   1500
tttaatcaaa gattttcaga taaggaagca ttattatgta aagattcaaa aggtaaaaat   1560
ttaccctaag aaaagaaagc tttccctgta aactctgtcc tctggacatc ctgaaaaaac   1620
aaagtatttt cttaccactg tatagctaag aagcttttga aataatattt ctttggcttc   1680
tacttgcaag cttacccatc tatatatatg tattttggga gtcacatatt tttaaattct   1740
tcctgcttta tttcccaaaa gttaatattc ctgtatattt tttcattatt atcttgttcc   1800
tgattatcca ttaaaactgc ctaaactgat aaacatttga agtaagaaaa agtgatccat   1860
tcttctttac aaaagtctgt agagctgcag aatatataga actaggaaat gattcaaatc   1920
atccctggtc tctcctggga ctgtcaggcc tctgaagtca taggtcggat ttcgttataa   1980
ccattttgtt atgctcttct agttattctg tcagtggaat cccaccatgg taatttctgg   2040
cattttcttt gtttcttgct gtttcaaaga acttggattc attcttctaa caccaaaatg   2100
ctacagtcat cagaagttta aaaaaaaact tgcaatttac agaattttat aatattacca   2160
ggcttttcac attttataaa gttgattttt aaataatatg caaatttcta ggacaggatt   2220
tttattgcca ttaacttatt tttgtggctg ctctttctaa atatccagat gaacctccta   2280
```

-continued

```
cctgggattt ctgtaatttt ctgatgctgt cattgtctcc caaagtgttt atgaaaagcc   2340
ctaaaaaagc tgccttcctt gtctattttc tgggaagttt cacaattgcc acaagtatag   2400
atttttgttt aaatatcttt taatgccttc attttcttgt ttgtcaggtt gtaaactgta   2460
tttggcttct cagtagtcct gctagtgagg aataggcaag gaagagcaag taaacaagaa   2520
atgttgcagt gtttttttcta ataacagctc tggaaataag cacaggaaga gtagtgtgta   2580
aaatatgaca tctgtctacc atatttgaat tctgtgtgaa cgaacttttt aattgagatt   2640
tgctaaagat caaatcaaca tggttagaaa ttatattttt aaactgaaaa tatagaaaaa   2700
tatatgttaa gaaaaggaaa acttggctta agaaaaataa tttttgttgt attaaaaaac   2760
ttgtattaag tttgttacag attgtggcac tagtcttaaa ttttacatgt catttgctga   2820
tctgacttaa aaattgttca aatgtttaaa aagttcttta aacattttaa aatgaccatg   2880
gggatcttgt ttagctctta ataacactag tcaagagttt aacatttagt tcctgtgtct   2940
agcctgcttg tatgttatag aagcacagga tggggctggt gagtgaatct gccaggctta   3000
gccatcacca cagcagctga ttcaaaatca gcactgcctg gatagtttga tccatttaac   3060
ttgaatcatg atgtcattaa ctagattaaa aattaaatgg gcaaataagt gcttttagat   3120
ctagaggaac caaccccttc tatattaaaa ttgaaatctc ttctccaagg attttatgat   3180
gaattaaaaa ttttaattta ggtaaagtgc gttatttgct ggtattattt taaatgtact   3240
gtaagtaaac tgaataacgg ttttatagat ttgaagaata taggaaaacc aagagggttt   3300
tgtttttatt tttgctggtt gaaagatgtt taaaaacatc atagtgtttt atttagttaa   3360
aggacagtac tgaaatggag tttatatttg ttacttctat tttgtaatat ttaataacag   3420
gattaggttg aaataaaata ataggaaaaa ctgtgcagaa tgtggatttt cctggtgtct   3480
cccccctcact ctggtacact gatgagctct gagcagaccc cactgcttta cagacctttg   3540
gctatacagg gagttctctt cctgttagtg ctaatgagat tttccccccc ccagaaaggc   3600
agcttctgtt tttaacctta tctatagata ggcttatcgg agaaggcaat ggcaccccac   3660
tccagaactc ttgcctggaa aatcccatgg atggaggagc ctggtgggct gcagtccatg   3720
gggtcgctaa gagttggaca cgactgagcg acttcacttt cacttttcac tttcatgcat   3780
tggagaagga aatggcaacc cactccggtg ttcttgcctg gagaatccgg gggacgaggg   3840
agcctggtga gctgctgtct atggggtcgc agagtcggac atgactgaag tgacttagca   3900
gcagcataga taccttttttg tactctgctt catttaccta atacttatca aagaatgaag   3960
gattccaaac aaatgagctt cttattttaa ctagtattta ctgcttaaca gccagtatga   4020
acatttgcac atttatgatg gcggcagtcc tattacatac tttcctaaaa acagagttta   4080
aagaaaataa ataattcctg gttgatttgg cttcatcatt aagagtaatc tattactata   4140
ctgttacaaa acagaaatgt actctacata gacatggtct ttcagatctc tatgtctctt   4200
atcatttcta gctgctttca gagttttatc acttctgagg caatgcttca gtttttccta   4260
ctcctaggca atatggtaaa tgccagttgc tgcttttttc ttaattccat gtggctggag   4320
gcattaaaaa caatctctga ctaggtgggt tgttgttata cccacaagta tttttaaaaa   4380
gtagtgaatt tctagttata tggacttgaa atgttctgga gtacactcaa acctaaagtg   4440
tacttattta catggtgtgg aaatgtgttt atttacattt aaatatatct gaaattcaga   4500
atatcaatga aaactcaaat gaaaaaagtt attcatttga aagaaaaaaa aaaaaaaagt   4560
tattcatttg agaaggcaag gttcagaaga ggaagttata caaacttcct atagactgct   4620
atttgcccag tatggattag ataaggatgt aaaacagaca cttaactagt tcacatgatc   4680
```

```
tcatatcaca tgatagtgtg agataaccgg gaattctaga gtaaatggct ttttctttca   4740

gcactggcac tactacaaaa tccttttatt tcaacagaag acctagggaa gactaagcta   4800

aaggtcagtg agcacctaaa aaccaaaatc tgctatgata tatttgtagt gaaatttatt   4860

tataggatgt taggagttgg ctgtatacta caaataggac attttcatct gtggaacatt   4920

aaaaaaaaat catttcaagt atatatatat acatttaaaa ataatttagg gcactgcctt   4980

catataaatg atggctaaag agaatagggt acatatacac agtgaggaca aagtcataga   5040

aaaatagtta agtatgaaat gagttatcta ttgatttatt atgataagga ctgtgcctga   5100

cacaatggtt taaggaagag acaggaaaac tcaatttcta ctctcgattt cctgtaaaat   5160

cagtgacaaa gaattcttag attatttcaa acttccctta gatactgagc tcagtaaatt   5220

gttctaggaa attatctctc atttcagact ttctcacatg agacatgtta ccatcttttg   5280

gctttctgac tatcgaaaaa aatagataaa atttccataa acagaagaat tataccacca   5340

ctgttcaata attgccttta aaatatttca catttcattt aaaagttctc ttcaaccttg   5400

tgataaaatg gtcaagaatt tttctaatag taaagttcca acaattttgt tatgccgagt   5460

tgctcagttg tgtctgactc ttgtgactcc atggactgta gcccaccagg ctcttctgtc   5520

catggggatt ctccaggcaa gaatactgga gtgggttgcc atgccctcct ccaggggata   5580

tttccaacca agggatcaaa cccaggtctc cctcattgta ggcagattct taattgtctg   5640

acctaccagg gaaaccctcc aacaatttta gtcaaattca aaatatccct taatgctaac   5700

cttaactgta tatccaaagt ttctcatttc caaattatct agaagcagtc ctaagccaaa   5760

aaacaggtgt tatgctctga atggtattat ttatactaat ggaataaatt gtagtgttaa   5820

gttttgctat taattttata tcagcactga ataacttctt tgaaattttc tgacttagtc   5880

taaaccaatt agaaagtgta aaatctcatt ctcagctcta gagcaagaaa gtaaacacat   5940

aaatttattc agcattttca agtcaattat aaatatataa gatacccacc aatatcttct   6000

ccaggctctg acaggcctcc tgggaacttc cacatgtttt tcagctgtag tattaaatca   6060

gaaagcaaag ttaacacagc tcttatttac taacatacac atacgtagag atgccacaga   6120

agctacccat aattgatcaa ggtggttgag aatttatttt ttcgtaactg ccaccaattt   6180

ttttcagctt ccttcctcac tcctttcttc tctcgggaaa ctgctgactt gtgaaatctt   6240

tcctatcttt ttatttagga aatagaagtg gtttttttta tgttaatgtg ataaattctg   6300

tatgagtgaa acagtggggg gaacatctac tgaatttgta tagttaaaaa tttttgctgc   6360

tagtttatta aagaatacat gaatcttact gatgctgcta taaattagta gaaaatatat   6420

aaatgtaatc actaaagtat gctattttta attttcaatt tactttctat attgtgtgtc   6480

taatcagata tattaatctt aagagttttc ttgttctctg tgttaatgat tttatgtaaa   6540

aatataattg tctttcctgg gaagtgtgaa taaaattgat ttaagtttct ggctaaaaaa   6600

a                                                                   6601
```

<210> SEQ ID NO 13
<211> LENGTH: 820
<212> TYPE: PRT
<213> ORGANISM: Bos taurus

<400> SEQUENCE: 13

```
Met Trp Ser Arg Lys Cys Leu Leu Phe Trp Ala Val Leu Val Thr Ala
1               5                   10                  15

Thr Leu Cys Thr Ala Lys Pro Ala Pro Thr Leu Pro Glu Gln Ala Gln
            20                  25                  30
```

```
Pro Trp Gly Ala Pro Val Glu Val Glu Ser Leu Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Asp Ser Asn Arg Thr Arg
65                  70                  75                  80

Ile Thr Gly Glu Glu Val Glu Val Arg Gly Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
    370                 375                 380

Ile Ser Cys Met Val Gly Ser Val Ile Ile Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
    450                 455                 460
```

```
Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Arg Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His His Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820
```

<210> SEQ ID NO 14
<211> LENGTH: 3400
<212> TYPE: DNA
<213> ORGANISM: Bos taurus

<400> SEQUENCE: 14

```
ggctccgcga gtcagcttgc aaaggaggat cgagcccacg gcggagtctc catggaggtg     60
```

```
tggagcctgg tcaccaacct ctaaccgcag aactgggatg tggagccgga agtgtctcct    120
cttctgggcc gtgctggtca cagccacgct ctgcactgcc aagccggccc cgaccttgcc    180
ggagcaagcc cagccctggg gagcccctgt ggaagtggag tccctcctgg tccaccccgg    240
tgacctgctg cagctccgct gtcggctgcg ggacgatgtt cagagcatca actggctgcg    300
ggacggggtg cagctggcgg acagcaaccg cacgcgcatc accggggagg aggtggaggt    360
tcggggctcc gtgcccgccg actcaggcct ctacgcctgc gtgaccagca gcccctccgg    420
cagtgacacc acctacttct ccgtcaacgt ctcagatgcg ctcccctcgt cggaggacga    480
tgatgacgac gatgactcct cttcggagga gaaggaaaca gataacacca aaccaaaccc    540
cgtggctccg tactggacgt caccagaaaa gatggaaaag aaactgcacg cagtgccagc    600
tgccaagaca gtgaagttca aatgcccttc cagtgggacc ccgaacccca cactgcgctg    660
gctgaaaaac ggcaaagaat tcaagcccga ccacaggatc ggaggctaca aggtccgtta    720
tgccacctgg agcatcatta tggactccgt ggtgccttcg gataagggca actacacctg    780
catcgtggag aacgaatacg gcagcatcaa ccatacctac cagcttgatg ttgtggagcg    840
gtcccctcac cggcccatcc tgcaggcggg cttgccagcc aacaagacgg tggccctggg    900
cagcaacgtg gagttcatgt gcaaggtgta cagtgacccg cagccccaca tccagtggct    960
gaagcacatt gaggtgaacg ggagtaagat tgggccggac aacctgcctt atgtccagat   1020
cttgaagacg gccggagtta acaccaccga caaagagatg gaggtgctgc acttaaggaa   1080
tgtctccttt gaggacgcgg gggagtatac atgcttggcg ggtaactcta tcggactctc   1140
ccatcactct gcatggctga ccgttctgga agccctggaa gagagaccgg cggtgatgac   1200
ttcgccgctg tacctggaga tcatcatcta ttgcacgggg gccttcctca tctcctgcat   1260
ggtggggtct gtcatcatct acaagatgaa gagcggcaca aagaagagtg acttccacag   1320
ccagatggcc gtgcacaagc tggccaagag catccctctg cgcagacagg taacagtgtc   1380
ggctgactcc agcgcgtcca tgaactccgg ggtcctgcta gttcggccct cgcgtctctc   1440
ctccagcggc acccctatgc tggccggggt ctctgaatat gagcttcccg aagaccctcg   1500
ctgggagctg cctcgggaca gactggtttt aggcaagccc ctgggagagg gctgctttgg   1560
gcaggtggtg ctggcggagg ccatcgggct ggacaaggac agacccaacc gtgtgaccaa   1620
agtggccgtg aagatgctga agtcggatgc aacagagaaa gacctgtcgg acctgatctc   1680
cgagatggag atgatgaaga tgattggaaa acacaagaac atcatcaatc tgctgggggc   1740
ctgtacacag gatggtccct tgtatgtcat cgtggagtac gcctccaagg gcaatctccg   1800
agagtacctg caggcccgga ggccgccagg gctggagtac tgctacaacc ccagccacca   1860
ccccgaggag cagctctcct ccaaggacct ggtgtcctgc gcctaccagg tggcccgagg   1920
catggagtat cttgcctcca agaagtgcat ccaccgggac ctggccgcca ggaacgtcct   1980
ggtgacggag gacaacgtga tgaagatcgc ggacttcggt cttgctcgag acatccacca   2040
catcgactac tataaaaaga caaccaacgg ccgactgccc gtcaaatgga tggcaccgga   2100
ggccttgttt gaccggatct acacccacca gagcgacgtg tggtcttttg gggtgctcct   2160
ctgggaaatc ttcactctgg gcggctcccc ataccctggg gtccccgtgg aggagctttt   2220
caagctgctg aaggagggtc atcgtatgga caagcccagt aactgcacca acgagctcta   2280
catgatgatg agagattgct ggcacgcggt cccctctcag agacccacct tcaagcagct   2340
ggtggaagac ctggaccgca tcgtggcctt gacctccaac caggagtacc tggacctgtc   2400
aatgcccctg gaccaatact cccccagctt ccccgacacc cgcagctcca cctgctcctc   2460
```

```
cggggaggat tccgtctttt ctcacgagcc cttgcccgag gaaccctgcc tgccccgaca   2520

cccggcccag ctggccaacg gcggactcaa acggcgctga ctggccccca caccccgcac   2580

cccttcccgg actccatcct caacgccttg cccctcctcc cgctggactc gctgcctccc   2640

ctgcgctctg ctggccggcc tccctgaggc ccgcaccccc gagctcccct cctctcctcc   2700

tcccagcctg acagaggagc agggaagccg gtccttgctg acggctacta cgtggcctgc   2760

ccaacgctgg accaagaccc cctccctgcc gcctggaggg ttgggcagtg agggctgagc   2820

cgccctcgag cgagagccga ctgagctttc ctgcattggt tttgcgtact ctgcgcagcc   2880

catggcccgt gttctgtggc agatcctcgg gccagagcgg gagttgggtg taggggtggt   2940

cagcgcccgg gcctccgcag gcgacctctg ttccagacgg atagtgccag tggtttattg   3000

attccgaaac taatttgctt tgctgaccaa atacctggta cccgagggtg gggacgcaga   3060

ggccgggagc cggcggcgtg gccctggggc ccagccccga agcaggggct ctgtacatag   3120

ctacgaagaa aacacaaagt gtataaatct gagtatatat ttacatgtct ttttaaaagg   3180

gtcgttacca gagatttacc cattggtaa gatgctcctg gtggttggga ggcatcagtt   3240

gctatatatt aaaaacaaag aaaaaagaaa aaaaaaaaaa aaaaaaaaaa aaaaaaaaaa   3300

aaaaaaaaaa aaaaaaaaaa aaaaaaaaaa aaaaaaaaaa aaaaaaaaaa aaaaaaaaaa   3360

aaaaaaaaaa aaaaaaaaaa aaaaaaaaaa aaaaaaaaaa                         3400


<210> SEQ ID NO 15
<211> LENGTH: 846
<212> TYPE: PRT
<213> ORGANISM: Bos taurus
<220> FEATURE:
<221> NAME/KEY: MOD_RES
<222> LOCATION: (453)..(453)
<223> OTHER INFORMATION: Any amino acid

<400> SEQUENCE: 15

Met Gly Leu Thr Ser Thr Trp Arg Tyr Gly Arg Gly Gln Gly Ile Gly
1               5                   10                  15

Thr Val Thr Met Val Ser Trp Gly Arg Phe Leu Cys Leu Val Val Val
            20                  25                  30

Thr Met Ala Thr Leu Ser Leu Ala Arg Pro Ser Phe Asn Leu Val Asp
        35                  40                  45

Asp Thr Thr Val Glu Pro Glu Glu Pro Pro Thr Lys Tyr Gln Ile Ser
    50                  55                  60

Gln Pro Glu Val Tyr Val Ala Ala Pro Arg Glu Ser Leu Glu Leu Arg
65                  70                  75                  80

Cys Leu Leu Arg Asp Ala Ala Met Ile Ser Trp Thr Lys Asp Gly Val
                85                  90                  95

His Leu Gly Pro Asn Asn Arg Thr Val Leu Ile Gly Glu Tyr Leu Gln
            100                 105                 110

Ile Lys Gly Ala Thr Pro Arg Asp Ser Gly Leu Tyr Ala Cys Thr Ala
        115                 120                 125

Ala Arg Asn Val Asp Ser Glu Thr Val Tyr Phe Met Val Asn Val Thr
    130                 135                 140

Asp Ala Ile Ser Ser Gly Asp Asp Glu Asp Asp Ala Asp Gly Ser Glu
145                 150                 155                 160

Asp Phe Val Ser Glu Asn Ser Asn Ser Lys Arg Ala Pro Tyr Trp Thr
                165                 170                 175

Asn Thr Glu Lys Met Glu Lys Arg Leu His Ala Val Pro Ala Ala Asn
            180                 185                 190
```

```
Thr Val Lys Phe Arg Cys Pro Ala Gly Gly Asn Pro Thr Pro Thr Met
        195                 200                 205

Arg Trp Leu Lys Asn Gly Lys Glu Phe Lys Gln Glu His Arg Ile Gly
    210                 215                 220

Gly Tyr Lys Val Arg Asn Gln His Trp Ser Leu Ile Met Glu Ser Val
225                 230                 235                 240

Val Pro Ser Asp Lys Gly Asn Tyr Thr Cys Val Val Glu Asn Asp Tyr
                245                 250                 255

Gly Ser Ile Asn His Thr Tyr His Leu Asp Val Val Glu Arg Ser Pro
            260                 265                 270

His Arg Pro Ile Leu Gln Ala Gly Leu Pro Ala Asn Ala Ser Thr Val
        275                 280                 285

Val Gly Gly Asp Val Glu Phe Val Cys Lys Val Tyr Ser Asp Ala Gln
    290                 295                 300

Pro His Ile Gln Trp Ile Lys His Val Glu Lys Asn Gly Ser Lys Tyr
305                 310                 315                 320

Gly Pro Asp Gly Leu Pro Tyr Leu Lys Val Leu Lys His Ser Gly Ile
                325                 330                 335

Asn Ser Ser Asn Ala Glu Val Leu Ala Leu Phe Asn Val Thr Glu Ala
            340                 345                 350

Asp Ala Gly Glu Tyr Ile Cys Lys Val Ser Asn Tyr Ile Gly Gln Ala
        355                 360                 365

Asn Gln Ser Ala Trp Leu Thr Val Leu Pro Lys Gln Gln Ala Pro Val
    370                 375                 380

Arg Glu Lys Glu Ile Pro Ala Ser Pro Asp Tyr Leu Glu Ile Ala Ile
385                 390                 395                 400

Tyr Cys Ile Gly Val Phe Phe Ile Ala Cys Met Val Val Thr Val Ile
                405                 410                 415

Leu Cys Arg Met Arg Asn Thr Thr Lys Lys Pro Asp Phe Ser Ser Gln
            420                 425                 430

Pro Ala Val His Lys Leu Thr Lys Arg Ile Pro Leu Arg Arg Gln Val
        435                 440                 445

Thr Glu Ser Arg Xaa Arg Val Ser Ala Glu Ser Ser Ser Ser Met Asn
    450                 455                 460

Ser Asn Thr Pro Leu Val Arg Ile Thr Thr Arg Leu Ser Ser Thr Ala
465                 470                 475                 480

Asp Thr Pro Met Leu Ala Gly Val Ser Glu Tyr Glu Leu Pro Glu Asp
                485                 490                 495

Pro Lys Trp Glu Phe Pro Arg Asp Lys Leu Thr Leu Gly Lys Pro Leu
            500                 505                 510

Gly Glu Gly Cys Phe Gly Gln Val Val Met Ala Glu Ala Val Gly Ile
        515                 520                 525

Asp Lys Glu Lys Pro Lys Glu Ala Val Thr Val Ala Val Lys Met Leu
    530                 535                 540

Lys Asp Asp Ala Thr Glu Lys Asp Leu Ser Asp Leu Val Ser Glu Met
545                 550                 555                 560

Glu Met Met Lys Met Ile Gly Lys His Lys Asn Ile Ile Asn Leu Leu
                565                 570                 575

Gly Ala Cys Thr Gln Asp Gly Pro Leu Tyr Val Ile Val Glu Tyr Ala
            580                 585                 590

Ser Lys Gly Asn Leu Arg Glu Tyr Leu Arg Ala Arg Arg Pro Pro Gly
        595                 600                 605

Met Glu Tyr Ser Tyr Asp Ile Asn Arg Val Pro Glu Glu Gln Met Ala
    610                 615                 620
```

```
Phe Lys Asp Leu Val Ser Cys Thr Tyr Gln Leu Ala Arg Gly Met Glu
625                 630                 635                 640

Tyr Leu Ala Ser Gln Lys Cys Ile His Arg Asp Leu Ala Ala Arg Asn
                645                 650                 655

Val Leu Val Thr Glu Asn Asn Val Met Lys Ile Ala Asp Phe Gly Leu
            660                 665                 670

Ala Arg Asp Ile Asn Asn Ile Asp Tyr Tyr Lys Lys Thr Thr Asn Gly
        675                 680                 685

Arg Leu Pro Val Lys Trp Met Ala Pro Glu Ala Leu Phe Asp Arg Val
    690                 695                 700

Tyr Thr His Gln Ser Asp Val Trp Ser Phe Gly Val Leu Met Trp Glu
705                 710                 715                 720

Ile Phe Thr Leu Gly Gly Ser Pro Tyr Pro Gly Ile Pro Val Glu Glu
                725                 730                 735

Leu Phe Lys Leu Leu Lys Glu Gly His Arg Met Asp Lys Pro Ala Asn
            740                 745                 750

Cys Thr Asn Glu Leu Tyr Met Met Met Arg Asp Cys Trp His Ala Val
        755                 760                 765

Pro Ser Gln Arg Pro Thr Phe Lys Gln Leu Val Glu Asp Leu Asp Arg
    770                 775                 780

Ile Leu Thr Leu Thr Thr Asn Glu Glu Tyr Leu Asp Leu Ser Gln Leu
785                 790                 795                 800

Leu Glu Gln Tyr Ser Pro Ser Tyr Pro Asp Thr Arg Ser Ser Cys Ser
                805                 810                 815

Ser Gly Asp Asp Ser Val Phe Ser Pro Asp Pro Met Pro Tyr Glu Pro
            820                 825                 830

Cys Leu Pro Gln Tyr Pro His Arg Asn Gly Ser Val Lys Thr
        835                 840                 845
```

<210> SEQ ID NO 16
<211> LENGTH: 4302
<212> TYPE: DNA
<213> ORGANISM: Bos taurus

<400> SEQUENCE: 16

```
ttttttttt tgcggggagt tggtcgtttg ctccatcccg acccacgctg ggcgcgggga      60

cagacccgat cgccggggat cgttgccatt caagaggctg cagcagcagc agcagcagca    120

gcggcaaggc cagcgagcgg ccgccgcagc accttggttc ctgagcccac cgccggctga    180

aggcattgct gcaggcagtc catgctcgta gaggaagggt gcagatggga ttaacgtcca    240

catggagata tggaagagga caggggatcg gcactgtaac catggtcagc tggggtcgct    300

tcctctgcct ggttgtggtc accatggcaa ccttgtccct ggcccggccc tccttcaatt    360

tagttgacga taccacggtt gagccggaag agccaccaac caaataccaa atctcccaac    420

cagaagttta cgtggctgcg ccccgggagt cgctagagtt gcgctgcctg ttgcgagatg    480

ccgccatgat cagttggact aaggatgggg tacacttggg gcccaacaat aggacagtgc    540

ttattgggga gtatttgcag ataaaaggtg ccacgcctag agactccggc ctctatgctt    600

gtactgctgc taggaacgta gacagtgaga ctgtctactt catggtcaat gtcacagatg    660

ccatctcatc cggagatgat gaggacgacg cagatggctc ggaggatttt gtcagtgaga    720

acagtaacag caagagagca ccatactgga ccaacacaga aaagatggaa aaacggctgc    780

acgcggtccc agcagccaac actgtcaagt tccgctgtcc agctgggggg aatccaacac    840

caaccatgag gtggctgaaa aacgggaagg aatttaagca ggagcatcgc attggaggct    900
```

-continued

```
ataaggtacg aaaccagcat tggagcctta ttatggaaag tgtggtcccg tctgacaaag    960
gaaattatac ctgcgtggtg gagaacgatt acgggtccat caatcatacg taccaccttg   1020
acgttgttga gcgatcacca caccggccca tcctccaagc cgggctgccg gcaaatgcct   1080
ccactgtggt tggaggcgat gtggagtttg tctgcaaagt gtacagcgat gcccagcccc   1140
atatccagtg gatcaaacac gtggaaaaga acggcagtaa atatgggccc gacgggctgc   1200
cctatctcaa ggttctgaag cactcgggga taaatagttc caatgcggaa gtgctggctc   1260
tgttcaatgt gacggaggcg gatgctggcg agtatatttg taaggtctcc aattatatag   1320
ggcaggccaa ccagtctgcc tggctcactg tcctgccaaa acagcaagct cctgtaagag   1380
aaaaggagat cccagcttcc ccagactacc tggaaatagc catttactgc ataggggtgt   1440
tcttcatcgc ctgcatggtg gtgacggtca tcttgtgccg gatgaggaac acgaccaaga   1500
agccggactt cagcagccag ccggctgtgc acaagctgac caagcgcatc cccctgcgga   1560
gacaggtaac agaaagtaga taaagagttt ctgctgagtc cagctcctcc atgaactcca   1620
ataccccgtt ggtgaggatt acaactcgcc tctcttcaac tgcagacacc cccatgctgg   1680
cgggggtctc cgagtacgag ctgccagaag atcccaaatg ggagtttcca agagataagc   1740
tgacgctggg caaacccctg ggagaaggtt gctttgggca agtggtcatg gctgaagcag   1800
tgggaattga caaggagaag cccaaggaag cagtcactgt ggccgtgaag atgttgaaag   1860
atgatgccac tgagaaagac ctttctgatc tggtgtccga gatggagatg atgaagatga   1920
ttgggaaaca caaaaatatc ataaatctcc ttggagcctg tactcaggat gggccgctct   1980
atgtcatcgt tgaatacgcc tctaaaggca accttcggga atacctgcgc gcccggaggc   2040
cacccgggat ggagtattcc tacgacatca accgcgttcc cgaggagcag atggccttca   2100
aggacctggt gtcgtgtacc taccagctgg cccggggcat ggagtacttg gcttcccaga   2160
aatgcattca tcgagattta gctgccagaa atgttttggt aacagaaaac aacgtgatga   2220
aaatagctga ctttggactg gccagagata tcaacaatat agactattac aaaaagacca   2280
caaatggccg acttccggtc aagtggatgg ctcccgaagc ccttttcgac agagtgtaca   2340
cccatcagag cgatgtctgg tccttcgggg tgttaatgtg ggagatcttc acgttagggg   2400
gttcgcccta cccagggatt cccgtggagg aactttttaa gctgcttaag gaaggacata   2460
ggatggacaa gccagcaaac tgcaccaacg aactgtatat gatgatgaga gactgctggc   2520
atgcggtacc ctcacagaga cccaccttca agcagttggt agaagacttg gatcgaattc   2580
tcacactcac aaccaatgag gaatacttgg acctcagtca gcttcttgaa caatattcac   2640
ctagttaccc tgacacaagg agttcttgct cttcgggaga tgattctgtt ttctctccgg   2700
accccatgcc ttacgaaccc tgccttcctc agtatccaca tagaaacggc agtgttaaaa   2760
catgaatggg cctgtccccc tgtccccaaa cagggtggca tcaggaactt agctgtactg   2820
agcagggggg gccttgcctc caggagcctg ttggcttggc ttgtatatat ggatcagagg   2880
agtaaatatt tggaaaagtg atcggcacac gtgtaaagaa tttatccagt tggagacttg   2940
taatcttcac caggagaaca agaaggttgt gggggcaatg gattgccatg ggccgccacg   3000
tgcttgtgac ccaccgtggg tactggctgt ggaccagccg gacttgaggc aaacacccgt   3060
tctgcctgcc ttgtgaattt tgtaataatt ggagaaaata tatgtcagcg cacacttata   3120
gagcacaatt gcagtatata ggtgctggat gtatgtaaat atattcaaat tatgtataaa   3180
tatatattat atatttacaa ggaattattt tttgtattga ttttaaatgg atgtcccagc   3240
gcacctagaa aattggtctc tctctctttt tttaaaaaat agctatttgc taaatgctgt   3300
```

```
ttcttacata gaatttctta attttcaccg agcagaggtg gaaaagtact tttgctttca   3360

gggaaaaatg atatgacatt aatttattaa tgaattggta atatacaaaa caatcgtttt   3420

ttgtgttttt ttttggtaat ttaagtggca tttctatgca ggcagcacac cagactagtt   3480

aatctcttgc ttgaacttaa ctagttacca gatcctctga aaagagaaat atttacaaaa   3540

tgtgactaat ttgggggaag tgaagttttg gtttatttgt atttcagctc tgctgtcaga   3600

tgattggtct ttaaccacct aactgcccgt atgaaagagc ccattgatga gaaggtgtgt   3660

tgtcttggtg cagcttggtc attgggccca taaacctttc actgggcttc ccaagacaaa   3720

cggtaccagc gttctcctaa aaagatgcct taatctgttc ctcaaaggag gaactctcat   3780

cgagatgcta aaagaatgtt ctgtccagcc gctggccttc tgcccctctc cccgccaagt   3840

tgcacattga tcagatcagc ctgcattctc tttggcgaat cttcatcaca gcttccagat   3900

ttactggcaa cagagaagtc tcttagaatc ttcacgccct gtcggagaaa atggaaacac   3960

tgagttgttc tgctgatagt ttgggggatc cttccatctt tttaagggat cgcttccgcc   4020

tcctctggca ggatctcacc gaaagatccc gccctatgcc aatgtcatgt tactgccatg   4080

gtgttcgttt tgtatgaacg tgttgtgttt tgctttcaaa acaccttctc actctgctct   4140

ggctgtgcaa catgaatgcg gatgacactg atttttaacg tgttatgaaa ttggagaaag   4200

tatttaataa aacctgttaa tttttatact gacaataaaa atgtttctac agatattaat   4260

gttaacaaga caaaataaat gtcatgcggc ttattttttt aa                      4302
```

<210> SEQ ID NO 17
<211> LENGTH: 802
<212> TYPE: PRT
<213> ORGANISM: Bos taurus

<400> SEQUENCE: 17

```
Met Gly Ala Pro Ala Arg Ala Leu Ala Phe Cys Val Ala Val Ala Val
1               5                   10                  15

Met Thr Gly Ala Ala Leu Gly Ser Pro Gly Val Glu Pro Arg Val Ala
            20                  25                  30

Arg Arg Ala Ala Glu Val Pro Gly Pro Glu Pro Ser Pro Gln Glu Arg
        35                  40                  45

Ala Phe Gly Ser Gly Asp Thr Val Glu Leu Ser Cys Arg Leu Pro Ala
    50                  55                  60

Gly Val Pro Thr Glu Pro Thr Val Trp Val Lys Asp Gly Val Gly Leu
65                  70                  75                  80

Ala Pro Ser Asp Arg Val Leu Val Gly Pro Gln Arg Leu Gln Val Leu
                85                  90                  95

Asn Ala Ser His Glu Asp Ala Gly Ala Tyr Ser Cys Arg Gln Arg Leu
            100                 105                 110

Ser Gln Arg Leu Leu Cys Leu Phe Ser Val Arg Val Thr Asp Ala Pro
        115                 120                 125

Ser Ser Gly Asp Asp Glu Gly Gly Asp Asp Glu Ala Glu Asp Thr Ala
    130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175

Asn Pro Thr Pro Ser Ile Thr Trp Leu Lys Asn Gly Lys Glu Phe Arg
            180                 185                 190

Gly Glu His Arg Ile Gly Gly Ile Lys Leu Arg Gln Gln Gln Trp Ser
```

```
        195                 200                 205

Leu Val Met Glu Ser Val Val Pro Ser Asp Arg Gly Asn Tyr Thr Cys
    210                 215                 220

Val Val Glu Asn Lys Phe Gly Arg Ile Gln Gln Thr Tyr Thr Leu Asp
225                 230                 235                 240

Val Leu Glu Arg Ser Pro His Arg Pro Ile Leu Gln Ala Gly Leu Pro
            245                 250                 255

Ala Asn Gln Thr Ala Val Leu Gly Ser Asp Val Glu Phe His Cys Lys
            260                 265                 270

Val Tyr Ser Asp Ala Gln Pro His Ile Gln Trp Leu Lys His Val Glu
        275                 280                 285

Val Asn Gly Ser Lys Val Gly Pro Asp Gly Thr Pro Tyr Val Thr Val
    290                 295                 300

Leu Lys Thr Ala Gly Ala Asn Thr Thr Asp Lys Glu Leu Glu Val Leu
305                 310                 315                 320

Ser Leu Arg Asn Val Thr Phe Glu Asp Ala Gly Glu Tyr Thr Cys Leu
            325                 330                 335

Ala Gly Asn Ser Ile Gly Phe Ser His His Ser Ala Trp Leu Val Val
            340                 345                 350

Leu Pro Ala Glu Glu Glu Leu Val Glu Ala Gly Glu Ala Gly Gly Val
        355                 360                 365

Phe Ala Gly Val Leu Ser Tyr Gly Leu Gly Phe Leu Leu Phe Ile Leu
    370                 375                 380

Ala Val Ala Ala Val Thr Leu Tyr Arg Leu Arg Ser Pro Pro Lys Lys
385                 390                 395                 400

Gly Leu Gly Ser Pro Ala Val His Lys Val Ser Arg Phe Pro Leu Lys
            405                 410                 415

Arg Gln Val Ser Leu Glu Ser Ser Ser Ser Met Ser Ser Asn Thr Pro
            420                 425                 430

Leu Val Arg Ile Ala Arg Leu Ser Ser Gly Glu Gly Pro Thr Leu Ala
        435                 440                 445

Asn Val Ser Glu Leu Glu Leu Pro Ala Asp Pro Lys Trp Glu Leu Ser
    450                 455                 460

Arg Ala Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Ala Ala
            485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
        515                 520                 525

Gly Lys His Lys Asn Ile Ile Asn Leu Leu Gly Ala Cys Thr Gln Gly
    530                 535                 540

Gly Pro Leu Tyr Val Leu Val Glu Tyr Ala Ala Lys Gly Asn Leu Arg
545                 550                 555                 560

Glu Tyr Leu Arg Ala Arg Arg Pro Pro Gly Thr Asp Tyr Ser Phe Asp
            565                 570                 575

Thr Cys Arg Leu Pro Glu Glu Gln Leu Thr Phe Lys Asp Leu Val Ser
            580                 585                 590

Cys Ala Tyr Gln Val Ala Arg Gly Met Glu Tyr Leu Ala Ser Gln Lys
        595                 600                 605

Cys Ile His Arg Asp Leu Ala Ala Arg Asn Val Leu Val Thr Glu Asp
    610                 615                 620
```

```
Asn Val Met Lys Ile Ala Asp Phe Gly Leu Ala Arg Asp Val His Asn
625                 630                 635                 640

Leu Asp Tyr Tyr Lys Lys Thr Thr Asn Gly Arg Leu Pro Val Lys Trp
                645                 650                 655

Met Ala Pro Glu Ala Leu Phe Asp Arg Val Tyr Thr His Gln Ser Asp
            660                 665                 670

Val Trp Ser Phe Gly Val Leu Leu Trp Glu Ile Phe Thr Leu Gly Gly
        675                 680                 685

Ser Pro Tyr Pro Gly Ile Pro Val Glu Glu Leu Phe Lys Leu Leu Lys
    690                 695                 700

Glu Gly His Arg Met Asp Lys Pro Ala Asn Cys Thr His Asp Leu Tyr
705                 710                 715                 720

Met Ile Met Arg Glu Cys Trp His Ala Ala Pro Ser Gln Arg Pro Thr
                725                 730                 735

Phe Lys Gln Leu Val Glu Asp Leu Asp Arg Val Leu Thr Val Thr Ser
            740                 745                 750

Thr Asp Glu Tyr Leu Asp Leu Ser Val Pro Phe Glu Gln Tyr Ser Pro
        755                 760                 765

Gly Gly Gln Asp Thr Pro Ser Ser Gly Ser Ser Gly Asp Asp Ser Val
    770                 775                 780

Phe Ala His Asp Leu Leu Pro Pro Ala Pro Ser Gly Ser Gly Gly Ser
785                 790                 795                 800

Arg Thr
```

<210> SEQ ID NO 18
<211> LENGTH: 2562
<212> TYPE: DNA
<213> ORGANISM: Bos taurus

<400> SEQUENCE: 18

```
ggccatgggg ggcagcatgc tggcgcgcgc cgcctgagga cgccgcaccc cccgcccccg      60

cgatgggcgc cccggctcgc gccctcgcgt tttgcgtggc agtggcggtc atgaccggcg     120

ccgccctcgg gtccccgggc gtggagcccc gcgtcgcgcg gagagcggca gaggtcccgg     180

gccccgagcc cagcccgcag gagcgggcct ttggcagcgg ggacaccgtg gagctgagct     240

gccgcttgcc ggcgggggtg cccacagagc ccaccgtctg ggtgaaggac ggcgtgggcc     300

tggcgccctc ggaccgcgtc ctggtggggc cgcagcggct acaggtgctc aacgcctccc     360

acgaggacgc cggagcctac agctgccgcc agcgcctctc ccagcggctg ctgtgcctct     420

tcagcgtgcg cgtgacagat gctccgtcct caggggatga cgagggtggg gacgacgagg     480

ccgaggacac agctggggcc ccttactgga cgcggcctga gcggatggac aagaagctgc     540

tagcggtgcc ggccgccaac acggttcgct tccgctgccc agctgctggc aaccccacgc     600

catccatcac ctggctgaag aacggcaagg agttccgggg cgagcaccgc atcgggggaa     660

tcaaactgcg gcagcagcag tggagcctgg tcatggagag cgtggtgccc tcggaccgcg     720

gcaactacac gtgcgtcgtg gagaacaagt tcggcagaat ccagcagacc tacaccctgg     780

acgtgctgga gcgctctccg caccggccca tcctacaggc cgggctgccc gctaaccaga     840

cagccgtgct gggcagcgat gtggagttcc actgcaaggt ctacagcgac gcccagcccc     900

acatccagtg gctcaagcac gtggaggtga acggcagcaa ggtggggccc gacggcacgc     960

cctacgtcac cgtgctcaag acggcgggcg ctaacaccac cgacaaggag ctagaggttc    1020

tatccttgcg caatgtcacc tttgaggacg cgggggagta cacatgtctg gcgggcaatt    1080

ctatcgggtt ttcccatcac tctgcgtggc tggtggtgct gccagctgag gaggagctgg    1140
```

```
tggaagccgg tgaggctggc ggtgtgttcg cgggtgtcct cagctacggg ctgggcttcc   1200
tcctcttcat cctggccgtg gccgccgtta cgctctaccg cctgaggagc ccccctaaga   1260
agggcctggg ctcgcccgcg gtgcacaagg tctcccgctt cccgctcaag cgacaggtgt   1320
ccttggagtc cagctcatcc atgagctcca acacaccgct ggtacgcatt gcccggctgt   1380
catcgggcga gggccccacc ctggccaacg tctctgagct cgagctgccc gccgacccca   1440
agtgggagct gtcccgggcc cggctgaccc tgggcaagcc tcttggggag ggctgcttcg   1500
gccaggtggt catggcagag gccattggca tcgacaagga ccgagctgcc aagcctgtca   1560
cggtggccgt gaagatgctg aaagatgacg ccacggataa ggacttatcg gacctggtgt   1620
ccgagatgga gatgatgaag atgatcggaa aacacaagaa cattatcaac ctgctaggcg   1680
cctgcacgca gggcgggccc ctgtacgtgc tggtggagta cgcggccaag ggcaacctgc   1740
gggaatacct gcgggcacgg cggcccccgg gcactgacta ctccttcgac acctgccggc   1800
tgcccgagga gcagctcacc ttcaaagacc tggtgtcctg cgcctaccag gtggcgcggg   1860
gcatggagta cctggcctcg cagaagtgca tccacaggga cctggcggcc cgcaacgtgc   1920
tggtgactga ggacaacgtg atgaaaatcg ccgacttcgg cctggctcgt gacgtgcaca   1980
acctcgacta ctacaaaaag accacaaacg gccgcctgcc cgtgaagtgg atggcacccg   2040
aggccttgtt tgaccgcgtc tacacccacc aaagtgacgt ctggtccttc ggggtcctgc   2100
tctgggagat cttcacgctg gggggctcgc cgtaccccgg catccccgtg gaggagctct   2160
tcaagctgct gaaggaaggc caccgcatgg acaagccggc caactgcacg catgacctgt   2220
acatgatcat gcgcgagtgc tggcacgccg cgccctcgca gaggcccacc ttcaagcagc   2280
tggtggagga cctggaccgt gtgctcaccg tgacgtccac cgacgagtac ctggacctgt   2340
cggtgccctt cgagcagtac tcgccgggcg gccaggacac ccccagctcc ggctcctcgg   2400
gggacgactc cgtgttcgct cacgacctgc tgcccccggc cccatccggc agcggaggct   2460
cgcggacgtg aagggccgcg gccagccggc cgagccccca tcaatgtgag aacagacccc   2520
agcccaccat gctgccgctg gcgtgccatg atcccttggt cc                     2562
```

<210> SEQ ID NO 19
<211> LENGTH: 800
<212> TYPE: PRT
<213> ORGANISM: Bos taurus

<400> SEQUENCE: 19

```
Met Arg Leu Leu Leu Val Leu Leu Gly Val Leu Leu Gly Ala Pro Gly
1               5                   10                  15

Ala Pro Ala Leu Ser Phe Glu Ala Ser Glu Glu Thr Glu Leu Glu Pro
            20                  25                  30

Cys Leu Ala Pro Ser Pro Glu Gln Gln Glu Gln Glu Leu Thr Val Ala
        35                  40                  45

Leu Gly Gln Pro Val Arg Leu Cys Cys Gly Arg Ala Glu Arg Ser Gly
    50                  55                  60

His Trp Tyr Lys Glu Gly Ser Arg Leu Thr Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Gln Tyr Leu Cys Leu Ser Arg Gly Ser Leu Leu Leu His Asn Val
            100                 105                 110

Thr Leu Val Val Asp Asp Ser Met Thr Ser Ser Asn Gly Asp Glu Asp
        115                 120                 125
```

```
Pro Lys Ile His Arg Gly Pro Leu Asn Gly His Val Tyr Pro Gln Gln
    130                 135                 140

Ala Pro Tyr Trp Thr His Pro Gln Arg Met Glu Lys Lys Leu His Ala
145                 150                 155                 160

Val Pro Ala Gly Asn Thr Val Lys Phe Arg Cys Pro Ala Ala Gly Asn
                165                 170                 175

Pro Met Pro Thr Ile Arg Trp Leu Lys Asp Gly Gln Asp Phe His Gly
            180                 185                 190

Glu His Arg Ile Gly Gly Ile Arg Leu Arg His Gln His Trp Ser Leu
        195                 200                 205

Val Met Glu Ser Val Val Pro Ser Asp Arg Gly Thr Tyr Thr Cys Leu
    210                 215                 220

Val Glu Asn Ser Leu Gly Ser Ile Arg Tyr Ser Tyr Leu Leu Asp Val
225                 230                 235                 240

Leu Glu Arg Ser Pro His Arg Pro Ile Leu Gln Ala Gly Leu Pro Ala
                245                 250                 255

Asn Thr Thr Ala Val Val Gly Ser Asp Val Glu Leu Leu Cys Lys Val
            260                 265                 270

Tyr Ser Asp Ala Gln Pro His Ile Gln Trp Leu Lys His Ile Val Ile
        275                 280                 285

Asn Gly Ser Ser Phe Gly Ala Asp Gly Phe Pro Tyr Val Gln Val Leu
    290                 295                 300

Lys Thr Ala Asp Ile Asn Ser Ser Glu Val Glu Val Leu Tyr Leu Arg
305                 310                 315                 320

Asn Val Ser Ala Glu Asp Ala Gly Glu Tyr Thr Cys Leu Ala Gly Asn
                325                 330                 335

Ser Ile Gly Leu Ser Tyr Gln Ser Ala Trp Leu Thr Val Leu Pro Glu
            340                 345                 350

Glu Asp Leu Thr Trp Thr Ala Thr Ala Pro Glu Gly Arg Tyr Thr Asp
        355                 360                 365

Ile Ile Leu Tyr Ser Ser Gly Ser Leu Ala Leu Ile Val Phe Leu Leu
    370                 375                 380

Leu Val Gly Leu Tyr Arg Arg Gln Thr Leu Leu Thr Arg His His Arg
385                 390                 395                 400

Gln Pro Ala Thr Val Gln Lys Leu Ser Arg Phe Pro Leu Ala Arg Gln
                405                 410                 415

Phe Ser Leu Glu Ser Gly Ser Ser Ala Lys Ser Ser Leu Ser Leu Val
            420                 425                 430

Arg Gly Val Arg Leu Ser Ser Ser Gly Pro Pro Leu Leu Ala Gly Leu
        435                 440                 445

Val Ser Leu Asp Leu Pro Leu Asp Pro Leu Trp Glu Phe Pro Arg Asp
    450                 455                 460

Arg Leu Val Leu Gly Lys Pro Leu Gly Glu Gly Cys Phe Gly Gln Val
465                 470                 475                 480

Val Cys Ala Glu Ala Phe Gly Met Asp Pro Thr Arg Pro Asp Gln Ala
                485                 490                 495

Ser Thr Val Ala Val Lys Met Leu Lys Asp Asn Ala Ser Asp Lys Asp
            500                 505                 510

Leu Ala Asp Leu Val Ser Glu Met Glu Val Met Lys Leu Ile Gly Arg
        515                 520                 525

His Lys Asn Ile Ile Asn Leu Leu Gly Val Cys Thr Gln Glu Gly Pro
    530                 535                 540

Leu Tyr Val Ile Val Glu Cys Ala Ala Lys Gly Asn Leu Arg Glu Phe
```

```
545                 550                 555                 560

Leu Arg Ala Arg Arg Pro Pro Gly Pro Asp Leu Ser Pro Asp Gly Pro
                565                 570                 575

Arg Ser Ser Glu Gly Pro Leu Ser Phe Pro Ala Leu Val Ser Cys Ala
            580                 585                 590

Tyr Gln Val Ala Arg Gly Met Gln Tyr Leu Glu Ser Arg Lys Cys Ile
        595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Gly Ile His His Ile Asp
625                 630                 635                 640

Tyr Tyr Lys Lys Thr Ser Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Ile Leu Leu Trp Glu Ile Phe Thr Leu Gly Gly Ser Pro
        675                 680                 685

Tyr Pro Gly Ile Pro Val Glu Glu Leu Phe Ser Leu Leu Arg Glu Gly
    690                 695                 700

His Arg Met Asp Arg Pro Pro His Cys Pro Pro Glu Leu Tyr Gly Leu
705                 710                 715                 720

Met Arg Glu Cys Trp His Ala Ala Pro Ser Gln Arg Pro Thr Phe Lys
                725                 730                 735

Gln Leu Val Glu Ala Leu Asp Lys Val Leu Leu Ala Val Ser Glu Glu
            740                 745                 750

Tyr Leu Asp Leu Arg Leu Thr Phe Gly Pro Tyr Ser Pro Ala Gly Gly
        755                 760                 765

Asp Ala Ser Ser Thr Cys Ser Ser Ser Asp Ser Val Phe Ser His Asp
    770                 775                 780

Pro Leu Pro Leu Arg Pro Ser Ser Phe Ser Phe Pro Gly Val Gln Thr
785                 790                 795                 800


<210> SEQ ID NO 20
<211> LENGTH: 3139
<212> TYPE: DNA
<213> ORGANISM: Bos taurus

<400> SEQUENCE: 20

attcctggct ctgcggccgg gggctgcgca actcccgagc agtcttctgt ctccgctggg      60

cgtgggggtc cgggctggcg ggagctgaga gcgaggccgc ggaggaccca gaaaggcagt     120

cataggaggc ccagcctggg tcctcgagag cggcaggaag gagatgcggc tgctgttggt     180

cctcctgggg gtcctgctgg gggcacctgg ggctccagct ttgtcctttg aggcctctga     240

ggaaacggag ctggagccct gcctggcccc cagcccggag cagcaagagc aggagttgac     300

ggtggccctt gggcagcctg tgcggttatg ctgcgggcgg gctgagcgca gtggccactg     360

gtacaaggag ggcagtcgcc tgacacctgc tggccgggta cgaggctgga gaggccgctt     420

ggagattgcc agcttcctac ccgaggatgc tggccagtac ctctgcctat cacgaggctc     480

cttgcttctg cacaacgtca ccttggttgt ggacgactcc atgacctcca gcaatggcga     540

cgaggacccc aagatccaca ggggccccctt gaatgggcac gtttaccccc agcaagcacc     600

ctactggacg cacccccagc gcatggagaa gaaactgcat gctgtgcctg ccgggaacac     660

cgtcaagttc cgctgtccag ctgcaggcaa ccccatgccc accatccgct ggctcaagga     720

tggacaggac ttccacgggg agcatcgcat tggaggcatt cggctgcgcc accagcactg     780
```

```
gagcctggtg atggaaagcg tggtgccctc tgaccgtggc acttacacct gcctcgtgga    840
gaattctttg ggcagcattc gctatagcta cctgctggac gtgctggagc ggtccccgca    900
ccggcccatc cttcaggcag ggctcccagc caacaccacg gctgtggtgg gcagtgacgt    960
ggaactgctc tgcaaggtgt acagcgacgc ccagccccac atccagtggc tgaagcacat   1020
cgtcatcaac ggcagcagct tcggtgccga cggcttcccc tatgtgcaag tcttaaagac   1080
agcggacatc aatagctcag aggtggaggt cttgtacctt cggaatgtat ctgctgagga   1140
tgcaggcgag tacacctgcc tggcgggcaa ctccatcggc ctttcctacc agtcggcctg   1200
gctcacggtg ctgccagagg aggatctcac gtggacagcg acagcacccg aaggcaggta   1260
cacggacatc atcctgtact cgtcaggctc tctggctttg atcgtgttcc tgctgctggt   1320
cgggctatat cgcaggcaga cgctcctcac ccgacaccac cgacagcccg ccaccgtgca   1380
gaagttgtct cgctttcctc tggcccgaca gttctcgctg gagtcaggct cctcagccaa   1440
gtcaagcttg tccctggtgc ggggtgtccg tctctcctcc agcggccccc ccttgctcgc   1500
tggcctcgtg agtctcgacc tgcctcttga cccactgtgg gagttccccc gggacaggct   1560
ggtgctggga aagcccctgg gcgagggctg ctttgggcag gtggtgtgcg cagaggcctt   1620
cggcatggac cccacccggc cagaccaagc cagcaccgtg gctgtcaaga tgcttaagga   1680
caacgcctcc gacaaggact tggcagacct ggtctctgag atggaggtga tgaagctgat   1740
tggccgacac aagaacatta tcaacctgct gggtgtctgc acccaggaag ggcccttgta   1800
cgtgatcgtg gagtgtgctg ccaagggcaa cctgcgggag ttcctgcggg cccgccgccc   1860
cccaggccct gacctcagcc ctgacgggcc tcggagcagc gaggggccgc tctccttccc   1920
tgccctggtc tcctgcgcct accaggtggc ccggggcatg cagtacctgg agtcccggaa   1980
gtgcatccac cgggacctgg ctgcccgcaa tgtactggtg accgaggaca atgtgatgaa   2040
gattgcagac ttcgggctgg cccgtggcat ccaccacatt gactactaca agaaaactag   2100
caacggccgc ctgcctgtca agtggatggc accagaggcc ttgtttgaca gagtctacac   2160
acaccagagt gatgtgtggt cgtttggaat cctgctgtgg gagatcttca ccctcggggg   2220
ctccccatac cctggcatcc ccgtggagga gctgttctcg ctgctacgag aggggcatcg   2280
gatggaccgg cccccacact gcccccccaga gctatacggg ctgatgcgcg agtgctggca   2340
cgcagcaccc tctcagaggc ccactttcaa gcaactggta gaggcactgg acaaggtcct   2400
gctggccgtc tctgaggagt acctcgacct ccgcctaacc tttggaccct actcccctgc   2460
cggcggggac gccagcagca cctgctcctc tagcgactct gtcttcagcc acgacccccct   2520
accactgagg cccagctcct tctccttccc tggggtgcag acgtgagcag aggcacaggc   2580
tgtatgggca gggtcagctg ccagccttgg gcctcctggc tcaactgaaa ccaggtggca   2640
ctcgtccttg gcagccccag gccctgacct aagggtacta tcccagatct ctggttctgt   2700
ttgggggagg tctgtccttg gtcctggggt ccctagtctc gagacttcct tctctggcct   2760
ctgggtctca agccagagtt caatcccagc ctcaaggccc tgttctttgg agtcgtggcc   2820
ccagtgttct aatggcttgt taaggttctg cttggacttc tgggccttgg tagaagtcct   2880
tgttccaggg ctttggttgg acctggctgc agggctgtct taaacctccc cgcttcccca   2940
taccaagaga ggtcttagac ctctgaaccc cacttcccca ggcctcccct gcctccctct   3000
gctgcttgtc ccagcatctt gatggaagga gcgcttgtgc ccaccccatc cccacaccgc   3060
cccgtgctgg ctgagaggct gggagcctac caaaacacag aagcaaatga ccttttataa   3120
attatttttt tgaaatgaa                                                 3139
```

<210> SEQ ID NO 21
<211> LENGTH: 114
<212> TYPE: PRT
<213> ORGANISM: Sus scrofa

<400> SEQUENCE: 21

```
Met Ser Leu Ile Phe Phe Thr Leu Tyr Ile Val Ile Phe Ser Leu Leu
1               5                   10                  15

Leu Ile Val Lys Leu Gln Leu Gln Ala Glu Glu Arg Gly Val Val Ser
            20                  25                  30

Ile Lys Gly Val Cys Ala Asn Arg Tyr Leu Ala Met Lys Glu Asp Gly
        35                  40                  45

Arg Leu Leu Ala Ser Lys Cys Val Thr Asp Glu Cys Phe Phe Phe Glu
    50                  55                  60

Arg Leu Glu Ser Asn Asn Tyr Asn Thr Tyr Arg Ser Arg Lys Tyr Ser
65                  70                  75                  80

Ser Trp Tyr Val Ala Leu Lys Arg Thr Gly Gln Tyr Lys Leu Gly Pro
                85                  90                  95

Lys Thr Gly Pro Gly Gln Lys Ala Ile Leu Phe Leu Pro Met Ser Ala
            100                 105                 110

Lys Ser
```

<210> SEQ ID NO 22
<211> LENGTH: 345
<212> TYPE: DNA
<213> ORGANISM: Sus scrofa

<400> SEQUENCE: 22

```
atgtctctta tcttctttac cctgtatatt gtaatttttt ccttattact tatagtcaaa      60

ctacaacttc aagcagaaga gagaggggtt gtgtctatca aaggagtgtg tgcaaaccgt     120

tatcttgcta tgaaggaaga tggaagatta ctggcttcta aatgtgttac agacgagtgt     180

ttcttttttg aacgactgga atctaataac tacaatactt accggtcgag gaaatactcc     240

agttggtatg tggcactgaa acgaacgggg cagtataaac ttggacccaa aacaggacct     300

gggcagaaag ctatactttt tcttccaatg tctgctaaga gctga                     345
```

<210> SEQ ID NO 23
<211> LENGTH: 818
<212> TYPE: PRT
<213> ORGANISM: Sus scrofa

<400> SEQUENCE: 23

```
Met Cys Ser Trp Lys Cys Leu Leu Phe Trp Ala Val Leu Val Thr Ala
1               5                   10                  15

Thr Leu Cys Thr Ala Arg Pro Ala Pro Thr Ser Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Val Glu Ser Asn Arg Thr Arg
65                  70                  75                  80

Ile Thr Gly Glu Glu Val Glu Val Arg Asp Ser Val Pro Ser Asp Ser
                85                  90                  95

Gly Leu Tyr Ala Cys Val Thr Ser Ser Pro Ser Gly Ser Asp Thr Thr
            100                 105                 110
```

```
Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Val Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
    370                 375                 380

Ile Ser Cys Met Val Gly Ser Val Ile Ile Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Ser Ala Asp Ser Ser Ala Ser
            420                 425                 430

Met Asn Ser Gly Val Leu Leu Val Arg Pro Ser Arg Leu Ser Ser Ser
        435                 440                 445

Gly Thr Pro Met Leu Ala Gly Val Ser Glu Tyr Glu Leu Pro Glu Asp
    450                 455                 460

Pro Arg Trp Glu Leu Pro Arg Asp Arg Leu Val Leu Gly Lys Pro Leu
465                 470                 475                 480

Gly Glu Gly Cys Phe Gly Gln Val Val Leu Ala Glu Ala Ile Gly Leu
                485                 490                 495

Asp Lys Asp Lys Pro Asn Arg Val Thr Lys Val Ala Val Lys Met Leu
            500                 505                 510

Lys Ser Asp Ala Thr Glu Lys Asp Leu Ser Asp Leu Ile Ser Glu Met
        515                 520                 525

Glu Met Met Lys Met Ile Gly Lys His Lys Asn Ile Ile Asn Leu Leu
```

```
    530                 535                 540

Gly Ala Cys Thr Gln Asp Gly Pro Leu Tyr Val Ile Val Glu Tyr Ala
545                 550                 555                 560

Ser Lys Gly Asn Leu Arg Glu Tyr Leu Gln Ala Arg Arg Pro Pro Gly
                565                 570                 575

Leu Glu Tyr Cys Tyr Asn Pro Ser His Asn Pro Glu Glu Gln Leu Ser
            580                 585                 590

Ser Lys Asp Leu Val Ser Cys Ala Tyr Gln Val Ala Arg Gly Met Glu
        595                 600                 605

Tyr Leu Ala Ser Lys Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Ile His His Ile Asp Tyr Tyr Lys Lys Thr Thr Asn Gly
                645                 650                 655

Arg Leu Pro Val Lys Trp Met Ala Pro Glu Ala Leu Phe Asp Arg Ile
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Val Pro Val Glu Glu
    690                 695                 700

Leu Phe Lys Leu Leu Lys Glu Gly His Arg Met Asp Lys Pro Ser Asn
705                 710                 715                 720

Cys Thr His Glu Leu Tyr Met Met Met Arg Asp Cys Trp His Ala Val
                725                 730                 735

Pro Ser Gln Arg Pro Thr Phe Lys Gln Leu Val Glu Asp Leu Asp Arg
            740                 745                 750

Ile Val Ala Leu Thr Ser Asn Gln Glu Tyr Leu Asp Leu Ser Met Pro
        755                 760                 765

Leu Asp Gln Tyr Ser Pro Ser Phe Pro Asp Thr Arg Ser Ser Thr Cys
    770                 775                 780

Ser Ser Gly Glu Asp Ser Val Phe Ser His Glu Pro Leu Pro Glu Glu
785                 790                 795                 800

Pro Cys Leu Pro Arg His Pro Pro Gln Leu Ala Asn Gly Gly Leu Lys
                805                 810                 815

Arg Arg


<210> SEQ ID NO 24
<211> LENGTH: 3974
<212> TYPE: DNA
<213> ORGANISM: Sus scrofa

<400> SEQUENCE: 24

cggggctatc gcggccccgc caggaccgga gcggagcccg gggcggcgg gccggagccg     60

aggacgcggg cgcccgcccg cccgcacaag ccacggcgga ctctccagag gcggaatcgc    120

cgagcccagt gagagtcagc tcaccaacga ggatcaagcc cacagcagcg tctccatgga    180

ggtgtggagc ctggtcacca acctctaacc gcagaactgg gatgtgcagc tggaagtgcc    240

tcctcttctg ggctgtgctg gtcacagcca cgctctgcac ggccaggccg gctccgacct    300

cgccggaaca agctcagccc tggggagccc ccgtggaagt ggagtccttc ctggtccacc    360

ccggtgacct gctgcagctc cgctgtcggc tgcgggacga tgttcagagc atcaactggc    420

tgcgggacgg ggtgcagctg gtggaaagca accgcacccg catcacaggg gaggaggtgg    480

aggtgcggga ctccgtgccc tccgactccg gcctctacgc ctgtgtgacc agcagcccct    540
```

-continued

```
cgggcagcga caccacctac ttctccgtca acgtctcaga tgctctcccc tcttcggagg    600
atgacgatga cgatgatgac tcctcctcag aggagaaaga gacagataac accaaaccaa    660
accccgtggc tccgtactgg acatccccag agaagatgga aaagaaattg catgcggtgc    720
cagctgccaa gacagtgaag ttcaagtgcc cctccagtgg gactcctaac cccaccttgc    780
gctggctgaa aaatggcaaa gaattcaagc ctgaccacag aatcggaggc tacaaggtcc    840
gttatgccac ctggagcatc atcatggact ccgtggtgcc ctccgacaag ggcaactaca    900
cctgcgtcgt ggagaacgag tatggcagca tcaaccacac ctaccagctt gacgttgtgg    960
agcggtcccc tcaccggccc atcctgcagg cagggttgcc agccaacaag acagtggccc   1020
tgggcagcaa tgtggaattc atgtgcaagg tgtacagtga cccacagccc cacatccagt   1080
ggctaaagca catcgaggtg aatgggagta agattggtcc ggacaaccta ccttatgtcc   1140
agatcttgaa gactgccggc gttaatacca ccgacaaaga gatggaggtg ctccacttaa   1200
ggaatgtctc ctttgaggac gcgggggagt atacatgctt ggcgggtaac tctatcggac   1260
tctcccatca ctctgcatgg ttgaccgttc tggaagccct ggaagagcgc ccggcggtga   1320
tgacctcgcc cttgtacctg gagatcatca tctactgcac aggggccttc ctcatctcct   1380
gcatggtggg gtctgtcatc atctacaaga tgaagagtgg caccaagaag agtgacttcc   1440
acagccagat ggccgtgcac aagctggcca agagcatccc tctgcgcaga caggtgtcag   1500
ctgactccag tgcctccatg aactctgggg tcctactggt tcggccgtcg cgtctctcct   1560
ccagtgggac cccccatgctg gctggggtct ccgaatacga gcttcctgaa gaccctcgct   1620
gggagctgcc tcgggacagg ctggttttag gcaaacccct gggagagggc tgctttgggc   1680
aggtggtgtt ggcagaggcc attgggctgg acaaggacaa gcccaaccgt gtgaccaaag   1740
tggctgtgaa gatgctgaag tcggatgcaa cagagaaaga cctgtcagac ctgatctctg   1800
agatggagat gatgaagatg attgggaagc acaagaacat catcaacctg ctgggggcct   1860
gcacgcagga cggacctctc tatgtcattg tggagtatgc ctccaagggc aacctccgtg   1920
agtacctgca ggcccggagg ccgcctggcc tggaatactg ctacaacccc agccacaacc   1980
cggaggagca gctctcctcc aaggacctgg tctcctgtgc ctatcaggtg gctcgaggca   2040
tggagtacct cgcttccaag aagtgcatac accgagacct ggccgccagg aacgtcctcg   2100
tgacggaaga caacgtgatg aagatcgcag actttggcct tgcccgggac atccaccaca   2160
ttgactacta caaaaagaca accaacggcc gactgccggt gaagtggatg gcaccggaag   2220
ctttgtttga ccggatctac acccaccaga gtgacgtgtg gtcttttggg gtgctcctgt   2280
gggaaatctt cactctgggc ggctccccat accctggcgt ccctgtggag gagcttttca   2340
agctgttgaa ggagggtcat cggatggaca agcccagtaa ctgcacccat gaactataca   2400
tgatgatgcg agactgttgg cacgcggtac cctcccagag acctaccttc aagcagctgg   2460
tggaagacct ggaccgcatt gtggccttga cctccaacca ggagtatctg gacctgtcga   2520
tgcccctgga ccagtactcc cccagcttcc ctgacacccg cagctctacc tgctcctctg   2580
gggaagattc cgtcttctct cacgaaccct tgcccgagga gccctgcctg ccccgacacc   2640
caccccagct tgccaacggc ggactcaaac ggcgctgacc ggcaccctgg cacccctccc   2700
caaactccat ccttagctgt gacccctccc ccctcctgct ggactctgcc ccaccccgcc   2760
ccttcctgct ggcaggagcc agctgcctac ctggggcctt cacccccagt tcccctctcc   2820
acctccccct cctctcagcc tgctggtgcg acagaggaac agggaggcag gtacttgctg   2880
acggccactt tgttctctcc cagtgttgga ccaagacccc ctccccctca ccgggcactg   2940
```

```
cctggagggg tgggaagtgg gggatgagca gcactcgagc gactgagctt tccggtgttg   3000

gttttgtctg ctccatgcag cctgtccacc cgggttctgg tggcaggtcc ttgggctaca   3060

gcagtggttg ggggcggggt cagtgcttgg gcctctgcgc cagatggatg gtgccaaggg   3120

cttcttaatt ccaatactaa tgtgctttgc tgaccaaata cctggtacca gaggatggag   3180

ttgcagaggc tggaagcagt gtggtggccc tggggcccag ccccaaacca ggggctttgt   3240

acatagctac gaagaaaaca caaagtgtat aaatctgagt atatatttac atgtcttttt   3300

aaaagggtcg ttaccagaga tttacccact ggggaagatg ctcctggtgg ctgggaggca   3360

tcggttgcta tatattaaaa acaaagaaaa aagaaaaaaa aaaaaggaaa atgtttttaa   3420

aaaggtcata tattttttgc tacttttgct gttttatttt tttaaattat gttctaaacc   3480

tattttcagt ttaggtccct caataaaaat tgctgctgct tcatttttat acgggctgtg   3540

tgacgcacac gggagaggat cttggccgca aaggagcaag cgggctctgg agctgtctgt   3600

ccagagtgcg tactatctgt ggtcccctcc cactcctcac cttatgtctc actcctaggc   3660

ctccgcacag accttgttgc ttttggaaag gcagggaaag aagatgagat gggcagggag   3720

cagaggcact gggcccaggg ccaggcttct cagccctcat ttccctgggg aagagaggag   3780

gaaggggatg gggggcagaa tggggtgtga gtgtcagaca gggagctgga ggcctggcct   3840

caaaagagcc aaggtgtagg agttcctgca gtggcacaac aggatcggtg gtgtcttggg   3900

tgtgctggga tgcagatttg atccctggcc cagcacagtg ggttaaggat ggggcgttgc   3960

cgcagctgtg actt                                                     3974
```

```
<210> SEQ ID NO 25
<211> LENGTH: 822
<212> TYPE: PRT
<213> ORGANISM: Sus scrofa

<400> SEQUENCE: 25

Met Val Ser Trp Gly Arg Phe Ile Cys Leu Val Val Val Thr Met Ala
1               5                   10                  15

Thr Leu Ser Leu Ala Arg Pro Ser Phe Asn Leu Val Glu Asp Thr Thr
            20                  25                  30

Val Glu Pro Glu Glu Pro Pro Thr Lys Tyr Gln Ile Ser Gln Pro Glu
        35                  40                  45

Val Tyr Val Ala Ala Pro Arg Glu Ser Leu Glu Leu Arg Cys Leu Leu
    50                  55                  60

Arg Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ala Arg Ser
            100                 105                 110

Val Asp Ser Glu Thr Val Tyr Phe Met Val Asn Val Thr Asp Ala Ile
        115                 120                 125

Ser Ser Gly Asp Asp Glu Asp Asp Thr Asp Gly Ser Glu Asp Phe Val
    130                 135                 140

Ser Glu Asn Ser Asn Ser Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Ser Pro Thr Pro Thr Met Arg Trp Leu
            180                 185                 190
```

```
Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Asp Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Val Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Thr Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Glu Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Val Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
```

```
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Asp Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Pro Tyr Pro Gln Arg
                805                 810                 815

Asn Gly Ser Val Asn Thr
            820


<210> SEQ ID NO 26
<211> LENGTH: 2738
<212> TYPE: DNA
<213> ORGANISM: Sus scrofa

<400> SEQUENCE: 26

tcgtccacat ggagatatgg aagaggacgg gggattggca gcgtaaccat ggtcagctgg      60

ggccgcttca tctgcctggt tgtggtcacc atggcaacct tgtctctggc ccggccctcc     120

ttcaatttag ttgaggatac cacggtggag ccggaagagc caccaaccaa ataccaaatc     180

tcccaaccag aagtttacgt ggctgcgccc cgggagtcgc tagagttgcg ctgcctgttg     240

cgagatgccg ccgtgatcag ttggactaag gatggggtac acttggggcc caacaatagg     300

acagtgctta ttggggagta cttgcagata aaaggtgcca cgcctaggga ctccggcctc     360

tatgcttgta ccgctgctag gagtgtagac agtgagactg tctacttcat ggtcaatgtc     420

acagatgcca tctcgtccgg agatgacgag gacgacaccg atggctcaga ggattttgtc     480

agtgagaaca gtaacagcaa gagagccccg tactggacca acacagaaaa gatggaaaaa     540

cggctgcacg ctgtccctgc cgccaacact gtcaagttcc gctgtccagc tgggggtagt     600

ccaacaccaa cgatgaggtg gctgaaaaac gggaaggaat ttaagcagga acatcgcatt     660

ggaggctata aggtacgaaa ccagcactgg agcctcatta tggaaagcgt ggttccatcc     720

gacaaaggaa attatacctg cgtggtggag aacgattacg ggtccatcaa tcacacrtac     780

cacctcgacg tcgttgagcg atcgccgcac cggcccatcc tccaagccgg actgccggcc     840

aacgcctcca ccgtggttgg gggcgacgtg gagtttgtct gcaaggtgta cagtgatgcc     900

cagccccaca tccagtggat caaacacgtg gaaaagaacg gcagcaaata cgggcccgac     960
```

```
gggctgcctt acctcaaggt tctgaagcac tcagggataa atagttccaa tgcagaagtg   1020

ctggctctgt tcaatgtgac tgaggcggat gctggggagt atatttgtaa ggtctccaat   1080

tatatagggc aggccaacca gtctgcctgg ctcactgtcc tgccaaaaca gcaagctccc   1140

gtgagagaaa aggagatcac agcttcccca gactacctgg agatagccat ttactgcata   1200

ggggtcttcc tgatcgcctg catggtggtg acggtcattc tgtgccggat gaagaccacc   1260

accaagaagc cggacttcag cagccagccg gcagtgcaca agctgaccaa gcgcatcccc   1320

ctgcggagac aggtaacagt ttctgccgag tccagctcct ccatgaactc caacacccca   1380

ctggtgagga ttacaactcg cctctcctcc acagcagaca cccccatgct ggcgggggtc   1440

tccgagtacg agctgccgga agatccaaag tgggagtttc ccagagataa gctgacgctg   1500

ggcaaacccc tgggagaagg ttgctttggg caagtggtca tggctgaagc ggtgggaatc   1560

gacaaagaga agcccaagga agcagtcact gtggccgtga agatgttgaa agatgatgcc   1620

acagagaaag acctttctga tctggtgtca gagatggaga tgatgaagat gattggcaaa   1680

cacaaaaata tcataaatct cctcggagcc tgtactcagg atgggccgct ctacgtcata   1740

gtcgagtacg cctcgaaagg caacctccga gagtacctgc gcgcccggcg gcctccgggg   1800

atggagtact cgtacgacgt caaccgcgtg cccgaggagc agatgacctt caaggacttg   1860

gtgtcctgca cctaccagct ggcccggggc atggagtact tggcctccca aaaatgtatc   1920

catcgagatt tagccgccag aaatgttttg gtaacagaaa acaatgtgat gaaaatagcc   1980

gacttcggac tggccagaga tatcaacaat atagactatt acaaaaagac caccaatggc   2040

cggcttccgg tcaagtggat ggctccagag gccctttttg atcgcgtgta cacccaccag   2100

agtgatgtct ggtccttcgg ggtgttaatg tgggagatct tcacgttagg gggctcgccc   2160

tacccaggga ttcccgtgga ggaacttttt aagctgctca aagaaggaca caggatggat   2220

aagccagcaa actgcaccaa cgaactgtat atgatgatga gagactgttg gcatgcggtg   2280

ccctcacaga gacccacctt caagcagttg gtagaagact tggatcgaat tctcacactc   2340

acgaccaatg aggactactt ggacctcagt cagcctctcg aacagtattc acctagttac   2400

cctgacacca ggagttcttg ctcttcggga gatgattctg ttttctctcc ggaccccatg   2460

ccttatgaac cctgccttcc tccgtaccca cagagaaacg gcagtgttaa cacatgaacg   2520

ggcttgtccc cctgtcccca gacagggccg cgccgggagc ctaggtgtac tgagcagggg   2580

aggccatgcc tcccgcagcc tgtatatatg gatcagagga gtaaataatt ggaaacgtgg   2640

atcggcagga gcctaggtgt actgagcagg ggaggccatg cctcccgcag cctgtatata   2700

tggatcagag gagtaaataa ttggaaacgt gatcggca                           2738
```

<210> SEQ ID NO 27
<211> LENGTH: 391
<212> TYPE: DNA
<213> ORGANISM: Sus scrofa

<400> SEQUENCE: 27

```
gtcatcggat ggacaagccc agtaactgca cccatgaact gtaagcatga ggagatgcct     60

ggggccctgg gctcagccct gggagggtgg gggatgggct ggacgrgtag aggagggaag    120

grgtgctyag ccagayaccg gggacttcct ggccacccct cccacagtcc tccggccctg    180

agcctttttt tttttaaaac tcagtgaatt ttattacatt tatagttgta caatgatcat    240

cacaacccta agcctttttt ttttttcatc tgcttcttct cttcctcccc tgacttcacc    300

atcctgcccc agatacatga tgatgcgaga ctgttggcac gcggtaccct cccagagacc    360
```

```
taccttcaag cagctggtgg aagacctgga c                              391


<210> SEQ ID NO 28
<211> LENGTH: 800
<212> TYPE: PRT
<213> ORGANISM: Sus scrofa

<400> SEQUENCE: 28

Met Gln Leu Leu Leu Ala Leu Leu Gly Val Leu Leu Ala Val Pro Gly
1               5                   10                  15

Ala Pro Ala Leu Ser Leu Glu Ala Ser Glu Glu Thr Glu Leu Glu Pro
            20                  25                  30

Cys Leu Ala Pro Ser Pro Glu Glu Gln Glu Arg Glu Leu Thr Val Val
        35                  40                  45

Leu Gly Gln Ser Val Arg Leu Cys Cys Gly Arg Ala Glu Arg Ser Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Phe Cys Leu Ala Arg Gly Ser Met Leu Val Leu His Asn
            100                 105                 110

Val Thr Leu Val Met Asp Asp Ser Met Ile Ser Ser Asn Gly Asp Glu
        115                 120                 125

Asp Pro Gly Thr His Ser Gly Pro Ser Asn Gly His Ile Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Met Pro Thr Ile Arg Trp Leu Lys Asp Gly Gln Asp Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ser Leu Gly Ser Ile Arg Tyr Ser Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Leu Thr Trp Thr Ala Ala Gly Pro Glu Ala Arg Tyr Thr
        355                 360                 365
```

```
Asp Val Ile Leu Tyr Ala Ser Gly Ser Leu Ala Leu Leu Val Leu Leu
    370                 375                 380

Leu Leu Ala Gly Leu Tyr Arg Arg Gln Val Leu His Gly Arg His Pro
385                 390                 395                 400

Arg Gln Pro Ala Thr Val Gln Lys Leu Ser Arg Phe Pro Leu Ala Arg
                405                 410                 415

Gln Phe Ser Leu Glu Ser Gly Ser Ser Ala Lys Ser Ser Ser Ser Leu
            420                 425                 430

Val Arg Gly Val Arg Leu Ser Ser Ser Gly Pro Pro Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Cys Ala Glu Ala Phe Gly Met Asp Pro Thr Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Ala Leu Val Ser Cys
            580                 585                 590

Ala Tyr Gln Val Ala Arg Gly Met Gln Tyr Leu Glu Ser Gln Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Ile His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ala Gly
        755                 760                 765

Gly Asp Ala Ser Ser Ser Cys Ser Ser Ser Asp Ser Val Phe Ser His
    770                 775                 780

Glu Pro Leu Pro Leu Gly Pro Ser Ser Phe Phe Pro Gly Val Gln Thr
785                 790                 795                 800
```

<210> SEQ ID NO 29
<211> LENGTH: 2820
<212> TYPE: DNA
<213> ORGANISM: Sus scrofa

<400> SEQUENCE: 29
atgcagctgc tgctggccct gttgggggtc ctgctggcag tgcctggggc tccagctttg 60
tctcttgagg cctctgagga aacggagctg gagccctgcc tggcccccag cccggaggag 120
caagagcggg agctgactgt ggtccttggg cagtctgtgc ggttatgctg tgggcgggct 180
gaacgtagtg gccactggta caaggagggt agtcgcctgg cacctgctgg ccgagtacga 240
ggctggagag gccgcttgga gattgccagc ttcctacccg aggatgctgg ccgatacttc 300
tgcctggcac gaggctccat gcttgtcctg cacaatgtca ccttggttat ggatgactcc 360
atgatctcca gcaacggtga tgaggacccc gggacccaca gtggcccctc gaatgggcac 420
atttaccccc agcaagcacc ctactggaca cacccccagc gcatggagaa gaaactgcat 480
gcagtgcctg ctgggaacac tgtcaagttt cgctgtccag cggcaggcaa ccccatgccc 540
accatccgct ggcttaagga tggacaggac ttccatgggg agaatcgcat tggaggcatt 600
aggctgcgcc accagcactg gagcctggtg atggaaagcg tggtgccatc ggaccgtggc 660
acatacacct gcctcgtgga gaactctttg ggcagcatcc gctacagcta tctgctggat 720
gtactggagc ggtccccgca ccggcccatc ctgcaggcgg ggctcccagc caataccaca 780
gccgtggtgg gcagcgacgt ggagctgtta tgcaaggtgt acagcgatgc ccagcctcac 840
atccagtggc tgaagcacat tgtcatcaac ggcagcagct ttggtgccga cggcttcccc 900
tatgtgcaag tcttaaagac agcagacatc aatagctcag aggtggaggt cctatacctt 960
cggaatgtgt ctgccgagga cgcaggtgaa tacacctgtc tggcaggcaa ctctatcggc 1020
ctttcctacc agtcagcttg gctcacagtg ttgccagaag aggacctcac gtggacggca 1080
gcagggcccg aggctaggta cacggatgtc atcctgtacg catcaggctc tctggctttg 1140
cttgtgcttc tgctgctggc tgggctctat cgccggcagg tgctccacgg ccggcacccc 1200
cggcagcccg ccaccgtgca gaaactctcc cgcttcccct tggcacgaca gttctccctg 1260
gagtcgggct cctcagccaa gtcaagctcg tctctggtgc ggggtgtccg tctctcctcc 1320
agcggccccc cattgctcgc tggcctcgtg agtctagacc tacctctcga cccactgtgg 1380
gagttccccc gggacaggct ggtgctcgga aagcccctgg gtgagggctg cttcgggcag 1440
gtggtgtgtg cagaggcctt tggcatggac cccacccggc ccgatcaagc cagcaccgtg 1500
gctgtcaaga tgcttaagga caatgcttct gacaaggact tggctgacct agtctctgag 1560
atggaggtga tgaagctgat tggccgacac aagaacatca tcaatctgct gggagtctgc 1620
acccaggaag ggcccctgta cgtgattgtg gagtgtgctg ccaagggaaa cctgcgggag 1680
ttcctgcggg cccgccgccc cccaggccct gacctcagcc ctgatgggcc tcggagcagt 1740
gagggaccac tttccttccc tgccctggtc tcctgcgcat atcaggtggc ccgaggcatg 1800
cagtacctgg agtcacaaaa gtgcatccac cgggacctgg ctgcccgcaa cgtgctggtg 1860
actgaggaca atgtgatgaa gatcgctgac tttgggctgg cccgaggcat ccaccatatt 1920
gactactaca agaaaacaag caacggccgc ctgcctgtca agtggatggc acctgaggcc 1980
ttgtttgaca gagtctacac acaccagagt gacgtgtggt catttgggat cctgctgtgg 2040
gagatcttta ccctcggggg ctccccgtac cctggcatcc ccgtggagga gctgttctcg 2100
ctgctacggg agggccatcg gatggaccgg cccccacact gccctccaga gttgtatggg 2160

```
ctgatgcgtg agtgttggca cgcagcaccc tctcagaggc ccactttcaa gcagctggtg   2220

gaggcactgg acaaggtcct gctggctgtc tctgaagagt accttgacct ccgcttaacc   2280

tttggaccct actcccccgc cggtggggac gccagcagct cctgctcctc cagcgactcg   2340

gtcttcagcc atgagcccct gcccctggga cccagctcct tcttccctgg ggtgcagacg   2400

tgagcggtgg caccaggttg taccagtagg ccagttggca gccttgggtc tcccggctca   2460

gccacaacct ggtgaccttg gcagccccag gtcctgactt aagggtactg tcccagattt   2520

ctggttccgc tttggggagg tccgtctctg gtcctgggct ccctagttga gacttcctgc   2580

tccggcctca gcttctcaag ccagaattca agtcgtctca aggccctgcc cttgccttag   2640

agtcatggtc gtagtgttct attggctttt gaggttctgc ttggcctcat gggccttgat   2700

gcttcgtcct tgttccaggg cttccgttgg tcctggctgc agggttgtcc taaatctccc   2760

tgcttcccta catcaagaga agtcctggcc tctgaaccct atttccccag gcctccccag   2820
```

<210> SEQ ID NO 30
<211> LENGTH: 237
<212> TYPE: PRT
<213> ORGANISM: Macaca mulatta

<400> SEQUENCE: 30

```
Met Pro His Val Tyr Pro Ser Ser Phe Gly Asp Leu Glu Ile Phe Lys
1               5                   10                  15

Ala Cys Ser Asp Thr Glu Ser Ser Leu Asp Ser Asn Phe Ser Thr Leu
            20                  25                  30

Gly Trp Lys Arg Leu Leu Arg Phe Glu Thr Leu Ala Gly Lys Lys Met
        35                  40                  45

Gly Glu Lys Val Glu Phe Lys Leu Leu Glu Val Glu Ser Arg Leu Val
    50                  55                  60

Ala Gln Gln Lys Pro Arg Thr Ala Arg Gly Pro Arg Gln Gly Pro Gly
65                  70                  75                  80

Gly Thr Met Ala Ala Gly Ser Ile Thr Thr Leu Pro Ala Leu Pro Glu
                85                  90                  95

Asp Gly Gly Ser Gly Ala Phe Pro Pro Gly His Phe Lys Asp Pro Lys
            100                 105                 110

Arg Leu Tyr Cys Lys Asn Gly Gly Phe Phe Leu Arg Ile His Pro Asp
        115                 120                 125

Gly Arg Val Asp Gly Val Arg Glu Lys Ser Asp Pro His Ile Lys Leu
    130                 135                 140

Gln Leu Gln Ala Glu Glu Arg Gly Val Val Ser Ile Lys Gly Val Cys
145                 150                 155                 160

Ala Asn Arg Tyr Leu Ala Met Lys Glu Asp Gly Arg Leu Leu Ala Ser
                165                 170                 175

Lys Cys Val Thr Asp Glu Cys Phe Phe Phe Glu Arg Leu Glu Ser Asn
            180                 185                 190

Asn Tyr Asn Thr Tyr Arg Ser Arg Lys Tyr Thr Ser Trp Tyr Val Ala
        195                 200                 205

Leu Lys Arg Thr Gly Gln Tyr Lys Leu Gly Ser Lys Thr Gly Pro Gly
    210                 215                 220

Gln Lys Ala Ile Leu Phe Leu Pro Met Ser Ala Lys Ser
225                 230                 235
```

<210> SEQ ID NO 31
<211> LENGTH: 1063
<212> TYPE: DNA

<213> ORGANISM: Macaca mulatta

<400> SEQUENCE: 31

```
atgccccacg tgtacccctc gtcttttggt gatttagaga ttttcaaagc ctgctctgac     60
acagaatctt ccttggattc caacttctct actttggggt ggaaacggct tctccgtttt    120
gaaacgctag cggggaaaaa aatgggggag aaagttgagt ttaaactttt agaagttgag    180
tcacggctgg ttgcgcagca aaagccccgc acggctcggg gtccccggca gggcccggga    240
gggaccatgg cagccgggag catcaccacg ctgcccgcct tgcccgagga tggcggcagc    300
ggcgccttcc cgcctggcca cttcaaggac cccaagcggc tgtactgcaa aaacgggggc    360
ttcttcctgc gcattcaccc cgacggccga gttgacgggg tccgggagaa gagcgaccct    420
cacatcaaat tacaacttca agcagaagag agaggagttg tgtctatcaa aggagtgtgt    480
gctaaccgtt accttgctat gaaggaagat ggaagattac tggcttctaa atgtgttaca    540
gatgagtgtt tctttttga acgattggaa tctaataact acaatactta ccggtcaagg    600
aaatacacca gttggtatgt ggcactgaaa cgaactgggc aatataaact tggatccaaa    660
acaggacctg ggcagaaagc tatacttttt cttccaatgt ctgctaagag ctgattttaa    720
tggccacatc taatctcatt tcacatgaaa gaagaagtat attgtagaaa tttgttaatg    780
agagtaaaag aaaataaatg tgtatagctc agtttggata attggtcaaa caacttttca    840
tctggtagta aaatatgtaa ccattgtccc agtaaagaaa actaacaaaa attgttgaaa    900
aatgtataga cttcccccctt ttatatagca tctgctgtta cccagtgaag cttacctaga    960
gcaatgatct ttttcatgca tttgctttat tcagaaagag gcttttaaaa tgtgcacatt   1020
tagaaacaaa agttcttcat ggaaatcata tacattagaa aat                    1063
```

<210> SEQ ID NO 32
<211> LENGTH: 511
<212> TYPE: PRT
<213> ORGANISM: Macaca fascicularis

<400> SEQUENCE: 32

```
Met Glu Lys Lys Leu His Ala Val Pro Ala Ala Lys Thr Val Lys Phe
1               5                   10                  15

Lys Cys Pro Ser Ser Gly Thr Pro Asn Pro Thr Leu Arg Trp Leu Lys
            20                  25                  30

Asn Gly Lys Glu Phe Lys Pro Asp His Arg Ile Gly Gly Tyr Lys Val
        35                  40                  45

Arg Tyr Ala Thr Trp Ser Ile Ile Met Asp Ser Val Val Pro Ser Asp
    50                  55                  60

Lys Gly Asn Tyr Thr Cys Ile Val Glu Asn Glu Tyr Gly Ser Ile Asn
65                  70                  75                  80

His Thr Tyr Gln Leu Asp Val Val Glu Arg Ser Pro His Arg Ser Ile
                85                  90                  95

Leu Gln Ala Gly Leu Pro Ala Asn Lys Thr Val Ala Leu Gly Ser Asn
            100                 105                 110

Val Glu Phe Met Cys Lys Val Tyr Ser Asp Pro Gln Pro His Ile Gln
        115                 120                 125

Trp Leu Lys His Ile Glu Val Asn Gly Ser Lys Ile Gly Pro Asp Asn
    130                 135                 140

Leu Pro Tyr Val Gln Ile Leu Lys Thr Ala Gly Val Asn Thr Thr Asp
145                 150                 155                 160

Lys Glu Met Glu Val Leu His Leu Arg Asn Val Ser Phe Glu Asp Ala
                165                 170                 175
```

```
Gly Glu Tyr Thr Cys Leu Ala Gly Asn Ser Ile Gly Leu Ser His His
            180                 185                 190

Ser Ala Trp Leu Thr Val Leu Glu Ala Leu Glu Glu Arg Pro Ala Val
        195                 200                 205

Met Thr Ser Pro Leu Tyr Leu Glu Ile Ile Ile Tyr Cys Thr Gly Ala
    210                 215                 220

Phe Leu Ile Ser Cys Met Val Gly Ser Val Ile Val Tyr Lys Met Lys
225                 230                 235                 240

Ser Gly Thr Lys Lys Ser Asp Phe His Ser Gln Met Ala Val His Lys
                245                 250                 255

Leu Ala Lys Ser Ile Pro Leu Arg Arg Gln Val Thr Val Ser Ala Asp
            260                 265                 270

Ser Ser Ala Ser Met Asn Ser Gly Val Leu Leu Val Arg Pro Ser Arg
        275                 280                 285

Leu Ser Ser Ser Gly Thr Pro Met Leu Ala Gly Val Ser Glu Tyr Glu
    290                 295                 300

Leu Pro Glu Asp Pro Arg Trp Glu Leu Pro Arg Asp Arg Leu Val Leu
305                 310                 315                 320

Gly Lys Pro Leu Gly Glu Gly Cys Phe Gly Gln Val Val Leu Ala Glu
                325                 330                 335

Ala Ile Gly Leu Asp Lys Asp Lys Pro Asn Arg Val Thr Lys Val Ala
            340                 345                 350

Val Lys Met Leu Lys Ser Asp Ala Thr Glu Lys Asp Leu Ser Asp Leu
        355                 360                 365

Ile Ser Glu Met Glu Met Met Lys Met Ile Gly Lys His Lys Asn Ile
    370                 375                 380

Ile Asn Leu Leu Gly Ala Cys Thr Gln Asp Gly Pro Leu Tyr Val Ile
385                 390                 395                 400

Val Glu Tyr Ala Ser Lys Gly Asn Leu Arg Glu Tyr Leu Gln Ala Arg
                405                 410                 415

Arg Pro Pro Gly Leu Glu Tyr Cys Tyr Asn Pro Ser His Asn Pro Glu
            420                 425                 430

Glu Gln Leu Ser Ser Lys Asp Leu Val Ser Cys Ala Tyr Gln Val Ala
        435                 440                 445

Arg Gly Met Glu Tyr Leu Ala Ser Lys Lys Cys Ile His Arg Asp Leu
    450                 455                 460

Ala Ala Arg Asn Val Leu Val Thr Glu Asp Asn Val Met Lys Ile Ala
465                 470                 475                 480

Asp Phe Gly Leu Ala Arg Asp Ile His His Ile Asp Tyr Tyr Lys Lys
                485                 490                 495

Lys Arg Ser Thr Ala Cys Glu Val Asp Gly Ala Arg Gly Ile Val
            500                 505                 510
```

<210> SEQ ID NO 33
<211> LENGTH: 2890
<212> TYPE: DNA
<213> ORGANISM: Macaca fascicularis

<400> SEQUENCE: 33

```
ttcagatgct ctcccctcct cagaggatga tgatgatgat gatgactcct cttcagagga      60

gaaagagaca gataacacca aaccaaaccc cgtagctcca tattggacat ccccagaaaa     120

gatggaaaag aaattgcatg cggtgccagc tgccaagaca gtgaagttca aatgcccttc     180

cagtgggacc ccaaacccca cactgcgctg gttgaaaaat ggcaaagaat tcaaacctga     240
```

```
ccacaggatt ggaggctaca aggtccgtta tgccacctgg agcatcataa tggactccgt    300
ggtgccctct gacaagggca actacacctg cattgtggag aatgagtatg gcagcatcaa    360
ccacacctac cagctggatg tcgtggagcg gtcccctcac cggtccatcc tgcaagcagg    420
gttgcccgcc aacaagacag tggccctggg tagcaacgtg gagttcatgt gtaaggtgta    480
cagtgaccca cagccgcata tccagtggct aaagcacatc gaggtgaacg ggagcaagat    540
tggtccagac aacctgcctt atgtccagat cttgaagact gctggagtta ataccaccga    600
caaagagatg gaggtgcttc acttaagaaa tgtctccttt gaggacgcag gggagtatac    660
gtgcttggcg ggtaactcta tcggactctc ccatcactct gcatggttga ccgttctgga    720
agctctggaa gagaggccgg cggtgatgac ctcgcccctg tacctggaga tcatcatcta    780
ttgcacaggg gccttcctca tctcctgcat ggtagggtcg gtcatcgtct acaagatgaa    840
gagtggcacc aagaagagcg acttccacag ccagatggct gtgcacaagc tggccaagag    900
catccctctg cgcagacagg taacagtgtc tgctgactcc agtgcgtcca tgaactctgg    960
ggttcttctg gttcggccat cacggctctc ctccagtggg actcccatgc tagcaggggt   1020
ctccgagtat gagcttcctg aagaccctcg ctgggagctg cctcgggaca gactggtctt   1080
aggcaaaccc ctgggagagg gctgctttgg gcaggtggtg ttggcagagg ccatcgggtt   1140
ggacaaggac aaacccaacc gtgtgaccaa agtggctgtg aagatgttga agtcggacgc   1200
aacagagaaa gacttgtcag acctgatctc agaaatggag atgatgaaga tgatcgggaa   1260
gcataagaat atcatcaacc tgctgggggc ctgcacgcag gacggtccct tgtatgtcat   1320
cgtggagtat gcctccaagg gcaacctgcg ggagtacctg caggcccgga ggcccccggg   1380
gctggaatac tgctacaacc ccagccacaa cccagaggag cagctctcct ccaaggacct   1440
ggtgtcctgc gcctatcagg tggcccgagg catggagtat ctggcctcca agaagtgcat   1500
acaccgagac ctggccgcca ggaatgtcct ggtgacagag gacaatgtga tgaagatagc   1560
agactttggc ctcgcacggg acattcacca catcgactac tataaaaaga aacggtcgac   1620
tgcctgtgaa gtggatggcg cccgaggcat tgtttgaccg gatctacacc caccagagtg   1680
atgtgtggtc tttcggggtg cttctgtggg agatcttcac tctgggcggc tccccatacc   1740
ctggtgtgcc tgtggaggag cttttcaagc tgctgaagga gggtcgccgc atggacaagc   1800
ccagtaactg caccaacgag ctgtacatga tgatgcggga ctgctggcat gcagtgccct   1860
cacagagacc caccttcaag cagctggtgg aagacctgga ccgcatcgtg gccttgacct   1920
ccaaccagga gtacctggac ctgtccatgc ccctggacca gtactccccg agctttcccg   1980
acacccggag ctctacatgc tcctcagggg aggattccgt cttctctcat gagccgctgc   2040
ccgaggagcc ctgcctgccc cgacacccag cccagcttgc caatggcggt ctcaaacgcc   2100
gctgactgcc acccacacgc cctccccaga ctctaccgtc agctgtaacc ctcacccaca   2160
gcccctgcca ggcccactgc ctgtccgtcc ctgtcccctt tcctgctggc aggagcccgc   2220
tgcctaccgg gggccttcct gtgtggcctg ccttcacccc gctcagctca cctcctcctc   2280
cgcctcctct ccacctgttg gtgagaggtg caaagaggca gatctttgct gccggccact   2340
tcatcccctc ccagatgttg gaccaagacc cctccctgcc accaggcact gcctggaggg   2400
cggggagtgg gagccgatga acaggcatgc aagtgagagc ttcctgagct ttctcctgtc   2460
agtttggtct gtttcgcctt cacccgtaag cccccttgcac tctggtggca ggtgccttgt   2520
cctcagggct acagcaatag ggaggtcagt gcttcgagcc tcgatcgaag gtgacctctg   2580
ctccagatgg gtggtgccag tggctttact aattccgata ctagtttgct ttgctcacta   2640
```

```
aatgcctggt accagaggat ggtgaggtga aggccaggtt gggggcagcg ttgtggccct   2700

ggggcccagc cccgaactgg gggctctgta catagctatg aagaaaacac aaagtgtata   2760

aatctgagta tatatttaca tgtcttttta aaagggtcgt taccagagat ttacccatcg   2820

ggtaagatgc tcctggtggc tgggaggcat cagttgctat atattaaaaa caaaaaaaaa   2880

aaaaaaaaaa                                                          2890


<210> SEQ ID NO 34
<211> LENGTH: 34
<212> TYPE: PRT
<213> ORGANISM: Macaca mulatta

<400> SEQUENCE: 34

Glu Gln Tyr Ser Pro Ser Tyr Pro Asp Thr Arg Ser Ser Cys Ser Ser
1               5                   10                  15

Gly Asp Asp Ser Gly Phe Ser Pro Asp Pro Met Pro Tyr Glu Pro Cys
            20                  25                  30

Leu Pro


<210> SEQ ID NO 35
<211> LENGTH: 106
<212> TYPE: DNA
<213> ORGANISM: Macaca mulatta

<400> SEQUENCE: 35

tcgaacagta ttcacctagt taccctgaca caagaagttc ttgttcttca ggagatgatt     60

ctggttttc tccagacccc atgccttacg aaccatgcct tcctca                   106


<210> SEQ ID NO 36
<211> LENGTH: 808
<212> TYPE: PRT
<213> ORGANISM: Macaca mulatta

<400> SEQUENCE: 36

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Val Ala Glu Val Ser Gly Pro Glu Pro Ser Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Ala Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Leu Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
```

```
            180                 185                 190

Lys Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Arg Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Thr Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605
```

```
Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805
```

```
<210> SEQ ID NO 37
<211> LENGTH: 2592
<212> TYPE: DNA
<213> ORGANISM: Macaca mulatta

<400> SEQUENCE: 37

ccccgccatg ggcgcccctg cctgcgccct cgcgctctgc gtggcagtgg ccatcgtggc     60

cggcgcctcc tcggagtcct tggggacgga gcagcgcgtc gtggggcgag tggcagaagt    120

gtccggcccg gagcccagcc agcaggagca gttggtcttc ggcagcgggg acgctgtgga    180

gctgagctgt cccccgcccg ggggtggtcc catggggccc actgtctggg tcaaggatgg    240

cgcagggctg gtgccctcgg agcgtgtcct ggtggggccc cagcggctgc aggtgctgaa    300

tgcctcccac gaggactctg gggcctacag ctgccggcag cggctcacac agctcgtact    360

gtgccacttc agtgtgcggg tgacagatgc tccatcctcg ggagatgacg aagacgggga    420

ggacgaggct gaggacacag gtgtggacac aggggcccct tactggactc ggcccgagcg    480

gatggacaag aagctgctgg ctgtgccggc cgccaacacc gtccgcttcc gctgcccggc    540

tgccggcaac cccactccct ccatctcctg gctgaagaat ggcaaggagt tccgcggcga    600

gcaccgcatt ggcggcatca agcttcggca ccagcagtgg agcctggtca tggaaagcgt    660

ggtgccctcg gaccgcggca actacacctg cgtggtggag aacaagtttg gcagcatccg    720

gcagacatac acgctggacg tgctggagcg ctccccgcac cggcccatcc tgcaggcggg    780

gctgccggcc aaccagacgg cggtgctggg cagcgatgtg gagtttcact gcaaggtgta    840

cagtgatgcg cagccccaca tccagtggct caagcacgtg gaggtgaatg gcagcaaggt    900

gggccccgac ggcacaccct acgtcaccgt gctcaagtcc tggatcagtg agagtgtgga    960

ggccgacgtg cgcctccgcc tggccaatgt gtcggagcgg gacgggggcg agtacctctg   1020
```

```
tcgagccacc aatttcatag gcgtggccga gaaggccttt tggctgagcg ttcacaggcc   1080
ccgagcagct gaggaggagc tggtggaggc tgacgaggcg ggcagtgtgt acgcaggcat   1140
cctcagctac ggggtgggct tcttcctgtt catcctggtg gtggcggctg tgacgctctg   1200
ccgcctgcgc agcaccccca agaaaggcct gggctccccc accgtgcaca agatctcccg   1260
cttcccactc aagcgacagg tgtccctgga gtccaacgcg tccatgagct ccaacacacc   1320
gctggtgcgc atcgcaaggc tgtcctcagg ggagggtccc acgctggcca atgtctccga   1380
gcttgagctg cctgctgacc ccaaatggga gctgtctcgg gcccggctga ccctgggcaa   1440
gccccttggg gagggctgct tcggccaggt ggtcatggcg gaggctatcg gcattgacaa   1500
ggaccgggcc gccaagcctg tcaccgtagc cgtgaagatg ctgaaagatg atgccactga   1560
caaggacctg tcagacctgg tgtctgagat ggagatgatg aagatgattg ggaaacacaa   1620
gaacattatc aacctgctgg gcgcctgcac gcagggcggg cccctgtacg tgctggtgga   1680
gtacgcggcc aagggcaacc tgagggagtt tctgcgggcg cggcggcccc cgggcctgga   1740
ctactccttc gacacctgca agccgcctga ggagcaactc accttcaagg acctggtgtc   1800
ctgtgcctac caggtggccc gaggcatgga gtacctcgcc tcccagaagt gcatccacag   1860
ggacctggct gctcgaaatg tgctggtgac cgaggacaac gtgatgaaga tcgcagactt   1920
cgggctggcc cgcgacgtgc acaaccttga ctactacaag aagacaacca acggccggct   1980
gcccgtgaag tggatggcgc ctgaggccct gtttgaccga gtctacaccc accagagtga   2040
cgtctggtcc tttggggtcc tgctctggga gatcttcacg ctgggggggct ctccgtaccc   2100
cggcatccct gtggaggagc tcttcaagct gctgaaggag ggtcaccgga tggacaagcc   2160
ggccaactgc acacacgacc tgtacatgat catgcgggag tgctggcatg ctgcgccctc   2220
ccagaggccc accttcaagc agctggtgga ggacctggac cgtgtcctca ctgtgacgtc   2280
caccgacgag tacctggacc tgtcagcgcc cttcgagcag tactcccccg gcggccagga   2340
caccccgagc tccagctcct caggggatga ctccgtgttt gcccacgacc tgctgccccc   2400
ggccccaccc agcagtgggg gctcgcggac gtgaagggcc actggtcccc aacaatgtga   2460
gggggtccct agcagcctac cctgctgctg gtgcacagcc actccccggc atgagactca   2520
gtgcagatgg agagacagct acacaaagct tcagtctgtg tgcatccgtg tgtgtgtctg   2580
cgtgcgtgtg ca                                                       2592
```

<210> SEQ ID NO 38
<211> LENGTH: 802
<212> TYPE: PRT
<213> ORGANISM: Macaca mulatta

<400> SEQUENCE: 38

```
Met Arg Leu Leu Ser Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Met Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95
```

```
Gly Arg Tyr Leu Cys Leu Ala Arg Ala Ser Met Ile Val Leu Gln Asn
            100                 105                 110

Leu Thr Leu Thr Ile Asp Asp Ser Leu Thr Ser Ser Asn Asp Asp Glu
        115                 120                 125

Asp Pro Gln Ser His Arg Asp Ser Ser Asn Gly His Ile Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ile Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Leu Thr Trp Thr Ala Ala Thr Pro Glu Ala Arg Tyr Thr
        355                 360                 365

Asp Val Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
```

```
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Gln Ser Ser Glu Gly Pro Leu Ala Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Ile His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Val Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ala Gly
        755                 760                 765

Gly Asp Thr Ser Ser Thr Cys Ser Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr
```

<210> SEQ ID NO 39
<211> LENGTH: 2901
<212> TYPE: DNA
<213> ORGANISM: Macaca mulatta

<400> SEQUENCE: 39

```
agttggtggg aagtccagcc tgggcccctg agagctgcgg gaaggagatg cggctgctgt      60

cggccctctt gggggtcctg ctgagtgtgc ctgggcctcc agtcttgtcc ctggaggcct     120

cggaggaagt ggagctggag ccctgcctgg ctcccagcat ggagcagcaa gagcaggagc     180

tgacagtagc ccttgggcag cctgtgcggc tgtgctgtgg gcgggctgag cgtggtggcc     240

actggtacaa ggagggcagt cgcctggcac ctgctggccg tgtacggggc tggaggggcc     300

gcctagagat tgccagcttc ctacctgagg atgctggccg ctatctctgc ctggcccgag     360

cctccatgat cgtcctgcaa aatctcacct tgactataga tgactccttg acctccagca     420

acgatgatga ggacccccag tcccataggg actcctcgaa tgggcacatt tacccccagc     480

aagcacccta ctggacacac ccccagcgca tggagaagaa actgcatgca gtaccggctg     540
```

```
ggaacaccgt caagttccgc tgtccggctg caggcaaccc cacgcccacc atccgctggc    600
ttaaggatgg acaggccttt catggggaga accgcattgg aggcattcgg ctgcgccacc    660
agcactggag tctcgtgatg gagagcgtgg tgccctcgga ccgcggcaca tacacttgcc    720
tggtggagaa cgctgtgggc atcatccgct ataactacct gctggatgtg ctggagcggt    780
ccccgcaccg gcccatcctg caggctgggc tcccggccaa caccacagcc gtggtgggca    840
gtgacgtgga gctgctgtgc aaggtgtaca gcgatgccca gccccacatc cagtggctga    900
agcacatcgt catcaacggc agcagcttcg ggccgacggc cttcccctat gtgcaagtcc    960
tgaagactgc agacatcaat agctcagagg tggaggtcct gtacctgcgg aacgtgtcag   1020
ccgaggacgc aggcgagtac acctgccttg caggcaattc catcggcctc tcctaccagt   1080
ctgcctggct cacggtgctg ccagaggagg acctcacatg gaccgcagca acgcccgagg   1140
ccaggtatac ggacgtcatc ctgtacgcgt cgggctccct ggccttggct gtgctcctgc   1200
tgctggccgg gctgtatcga gggcaggcgc tccacggccg gcacccccgc ccacccgcca   1260
ccgtgcagaa gctctcccgc ttccctctgg cccgacagtt ctccctggag tcaggctctt   1320
ccagcaagtc aagctcatcc ctggtgcgag gcgtgcgtct ctcctccagc ggccccgcct   1380
tgctcgccgg cctcgtgagt ctagacctac ctctcgaccc actgtgggag ttcccccggg   1440
acaggctggt gcttgggaag cccctgggcg agggctgctt tggacaggta gtacgtgcag   1500
aggcctttgg catggaccct gcccggcctg accaagccag tactgtggct gtcaagatgc   1560
tcaaagacaa cgcctctgac aaggacctgg ctgacctggt ctcggagatg gaggtgatga   1620
agctgattgg ccgacacaag aacatcatca acctgctggg tgtctgcacc caggaagggc   1680
ccctgtatgt aatcgtggag tgcgctgcca agggaaacct tcgggagttc ctgcgggccc   1740
ggcgcccccc gggccctgac ctcagcccgg acggtcctca gagcagtgag ggggccactcg   1800
ccttcccagt cctggtctcc tgcgcctacc aggtggcccg aggcatgcag tatctggagt   1860
cccggaagtg tatccaccgg gacctggctg cccgcaatgt gctggtgacg gaggacaatg   1920
tgatgaagat agctgacttt gggctggccc gtggcatcca ccacattgac tactataaga   1980
aaaccagcaa cggccgcctg cctgtcaagt ggatggcgcc cgaggccttg tttgaccgag   2040
tgtacacaca ccagagtgac gtgtggtctt ttggggtcct gctgtgggag atcttcaccc   2100
tcgggggctc cccgtatcct ggcatcccgg tggaggagct gttctcactg ctgcgggagg   2160
gacatcggat ggaccgaccc ccacactgcc ccccagagct gtacgggctg atgcgtgagt   2220
gctggcatgc agcaccctcc cagaggccca ccttcaagca gctggtggag gcgctggaca   2280
aggtcttact ggccgtctct gaggagtacc tcgacctccg cctgaccttc ggaccctatt   2340
cccctgctgg tggggacacc agcagcacct gctcctccag tgactccgtc ttcagccacg   2400
acccccctgcc actgggatcc agctccttcc cctttgggtc tggggtgcag acatgagtaa   2460
ggctcaaggc tgtgcaggca cataaactag tggccttggg ccttggggct cagccacagc   2520
ctggcacagt gcttgacctt ggcagcacgg ggtccctggc ccagagtgct gtcccaggtc   2580
caaggccgtg cccttgccct tggcgctgca gtgcctgtgt cctgatgggc caaacgtcag   2640
ggttctgctc ggcccttgga ccttggcgct cagcccccac ctcaggtttg gctgagcctg   2700
gctggagagc tgctatgcta aatctcctgc ctcccaatac cagcaggggg ttcagggcct   2760
ctgaaccccc tttccccaca cctccccctg ctgcttgccc cagcgtcttg atgggagcgt   2820
cggcccctga gcccagagaa gctggaagcc cgccaaaaac aggagcaaat ggcgttctat   2880
aaattatttt tttgaaataa a                                             2901
```

<210> SEQ ID NO 40
<211> LENGTH: 154
<212> TYPE: PRT
<213> ORGANISM: Mus musculus

<400> SEQUENCE: 40

```
Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150
```

<210> SEQ ID NO 41
<211> LENGTH: 695
<212> TYPE: DNA
<213> ORGANISM: Mus musculus

<400> SEQUENCE: 41

```
ggccccgggc cgttgtacac tcaaggggct ctctcggctt caggaagagt ccggctgcac      60

tgggctggga gcccggcggg acacggactg ggaggctggc agcccgcggg cgagccgcgc     120

tggggggccg aggccggggt cggggccggg gagccccaag agctgccaca gcggggtccc     180

ggggccgcgg aagggccatg gctgccagcg gcatcacctc gcttcccgca ctgccggagg     240

acggcggcgc cgccttccca ccaggccact tcaaggaccc caagcggctc tactgcaaga     300

acggcggctt cttcctgcgc atccatcccg acggccgcgt ggatggcgtc cgcgagaaga     360

gcgacccaca cgtcaaacta caactccaag cagaagagag aggagttgtg tctatcaagg     420

gagtgtgtgc caaccggtac cttgctatga aggaagatgg acggctgctg gcttctaagt     480

gtgttacaga agagtgtttc ttctttgaac gactggaatc taataactac aatacttacc     540

ggtcacggaa atactccagt tggtatgtgg cactgaaacg aactgggcag tataaactcg     600

gatccaaaac gggacctgga cagaaggcca tactgtttct tccaatgtct gctaagagct     660

gactcacttt tgacactgtc actgagacac tgtca                                695
```

<210> SEQ ID NO 42
<211> LENGTH: 822
<212> TYPE: PRT
<213> ORGANISM: Mus musculus

<400> SEQUENCE: 42

```
Met Trp Gly Trp Lys Cys Leu Leu Phe Trp Ala Val Leu Val Thr Ala
```

```
1               5                   10                  15

Thr Leu Cys Thr Ala Arg Pro Ala Pro Thr Leu Pro Glu Gln Ala Gln
            20                  25                  30

Pro Trp Gly Val Pro Val Glu Val Glu Ser Leu Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Val Glu Ser Asn Arg Thr Arg
65                  70                  75                  80

Ile Thr Gly Glu Glu Val Glu Val Arg Asp Ser Ile Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Arg Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Leu Gly Ser Val Ile Ile Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430
```

```
Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Ile Pro Leu Asp Gln Tyr Ser Pro Ser Phe Pro Asp Thr Arg
    770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Thr Gln Leu Ala Asn
                805                 810                 815

Ser Gly Leu Lys Arg Arg
            820
```

<210> SEQ ID NO 43
<211> LENGTH: 5008
<212> TYPE: DNA
<213> ORGANISM: Mus musculus

<400> SEQUENCE: 43

```
agccctcgcg cctcgccggc gcacagcgct cggagcgctc ctgcgggtac tttggcgggg     60
ctctccgctg cgggcggcgc ggaacgggag ccggaaccct ggtgcagccg ctgcgtgcag    120
aggacccggg ctgcgcaggg aagcggggcc gagacgtccg gactggactg agactgtgct    180
tagcgcattg cggcgacctc gcctttcccg gccgcgagcg cgcgccgcag ctggaaaagc    240
agcggagacc gaggactttt ctcaggtccc aggggcgcac cacagccgtg ctgcagtcaa    300
tgcacgccgg agccccagga ggggtgatgg aactcgggct gccagaagcc tgagacgccg    360
ccaccgccgc cgctgcgtac tggagagcgg ggggcgcacg atctggggac cccgggcggc    420
ggacccgagc cctcccccc gccccgcctc cggggcacca gcttcggctc cattgttccc    480
gcccgggctg gaggcgcccg gctcggagtg ccgccgggag tcgtgcctcg gccgcggagc    540
cctcgagacc ccatcaggat ctgaacggag cccggagacg agcggcggga gcgcaagaca    600
cagacacccg ccgcgccacg gcgagctctc cagaggcggg accgcagcgc caagtgagag    660
tcagcttgcg aaggcagacc acgctcacgg tggaatatcc atggaggtac ggagccttgt    720
taccaacctc taaccgcaga actgggatgt ggggctggaa gtgcctcctc ttctgggctg    780
tgctggtcac agccactctc tgcactgcca ggccagcccc aaccttgcct gaacaagctc    840
agccctgggg agtccctgtg gaagtggagt ctctcctggt ccaccctggc gacctgctac    900
agcttcgctg tcggcttcgc gatgatgtgc agagcatcaa ctggctgcgg gatggggtgc    960
agctggtgga gagcaaccgt acccgcatca caggggagga ggtggaggtg cgggactcca   1020
tccccgctga ctctggcctc tacgcttgcg tgaccagcag cccctctggc agcgatacca   1080
cctacttctc cgtcaatgtc tcagatgcac tcccatcctc ggaagatgat gacgacgacg   1140
atgactcctc ctcggaggag aaagagacgg acaacaccaa accaaaccgt aggcctgtag   1200
ctccctactg gacatcccca gagaaaatgg agaagaaact gcatgcggtg cccgctgcca   1260
agacggtgaa gttcaagtgc ccgtcgagtg ggacacccaa ccccactctg cgctggttga   1320
aaaatggcaa agagtttaag cctgaccacc gaattggagg ctacaaggtt cgctatgcca   1380
cctggagcat cataatggat tctgtggtgc cttctgacaa gggcaactac acctgcatcg   1440
tggagaatga gtatgggagc atcaaccaca cctaccagct tgacgtcgtg gaacgatctc   1500
cgcaccgacc catccttcag gcagggctgc ctgccaacaa gacagtggcc ctgggcagca   1560
atgtggagtt catgtgtaag gtgtacagcg atccgcagcc tcacattcag tggctgaagc   1620
acatcgaggt gaacgggagt aagatcgggc cagacaactt gccgtatgtc cagatcctga   1680
agactgctgg agttaatacc accgacaagg aaatggaggt gcttcatcta cggaatgtct   1740
cctttgagga tgcgggggag tatacgtgct tggcgggtaa ctctatcgga ctctcccatc   1800
actctgcatg gttgaccgtt ctggaagccc tggaagagag accagctgtg atgacctcac   1860
cgctctacct ggagatcatt atctactgca ccggggcctt cctgatctcc tgcatgttgg   1920
gctctgtcat catctataag atgaagagcg gcaccaagaa gagcgacttc catagccaga   1980
tggctgtgca caagctggcc aagagcatcc ctctgcgcag acaggtaaca gtgtcagctg   2040
actccagtgc atccatgaac tctggggttc tcctggttcg gccctcacgg ctctcctcca   2100
gcgggacccc catgctggct ggagtctccg aatatgagct ccctgaggat ccccgctggg   2160
agctgccacg agacagactg gtcttaggca aaccacttgg cgagggctgc ttcgggcagg   2220
tggtgttggc tgaggccatc gggctggata aggacaaacc caaccgtgtg accaaagtgg   2280
ccgtgaagat gttgaagtcc gacgcaacgg agaaggacct gtcggatctg atctcggaga   2340
```

```
tggagatgat gaaaatgatt gggaagcaca agaatatcat caaccttctg ggagcgtgca   2400
cacaggatgg tcctctttat gtcattgtgg agtacgcctc caaaggcaat ctccgggagt   2460
atctacaggc ccggaggcct cctgggctgg agtactgcta taaccccagc cacaaccccg   2520
aggaacagct gtcttccaaa gatctggtat cctgtgccta tcaggtggct cggggcatgg   2580
agtatcttgc ctctaagaag tgtatacacc gagacctggc tgctaggaac gtcctggtga   2640
ccgaggataa cgtaatgaag atcgcagact ttggcttagc tcgagacatt catcatatcg   2700
actactacaa gaaaaccacc aacggccggc tgcctgtgaa gtggatggcc cctgaggcgt   2760
tgtttgaccg gatctacaca caccagagcg atgtgtggtc ttttggagtg ctcttgtggg   2820
agatcttcac tctgggtggc tccccatacc ccggtgtgcc tgtggaggaa cttttcaagc   2880
tgctgaagga gggtcatcga atggacaagc ccagtaactg taccaatgag ctgtacatga   2940
tgatgcggga ctgctggcat gcagtgccct ctcagagacc tacgttcaag cagttggtgg   3000
aagacctgga ccgcattgtg gccttgacct ccaaccagga gtatctggac ctgtccatac   3060
cgctggacca gtactcaccc agctttcccg acacacggag ctccacctgc tcctcagggg   3120
aggactctgt cttctctcat gagccgttac ctgaggagcc ctgtctgcct cgacacccca   3180
cccagcttgc caacagtgga ctcaaacggc gctgactacc aaccctgtcc ccagttttct   3240
cccattccgt cgtcacccgt gcccctcacc cacaatcccc ttgttggaca cactgccttt   3300
ctcctcctcc tttgccgctg gcaagagcca gtgcctgact gaggccttcc tgtgttgtgg   3360
ccttccccct ccatcacccc caagacccct cttctccctc ttcttagcct gctgtgtgag   3420
agaggagcca agaggcaggt gcttgccgac ggccgcatcc tccttcccag gtgttggacc   3480
aagacccgcc ccgctgcctg gcactgcttg gaggtgtgca gagcggaagc aagtggagca   3540
tccggggcat tcctgttgac ccatcagccc cttctgttct ggcggcaggg gccttggggc   3600
tcctggaagc cgtgaggttt ctgtttaggc cttaaccgaa ggcaacctct gctccagatg   3660
gatggtacca gtagcttctt aattccaata ctaatttgct ttgctgacca aatacctgcc   3720
tggtaccaga agacagggag gcagagactg ggagccgtga tgtgcccttg ggctgagccc   3780
tagacttggg gctctgtaca tagctatgaa gaaaaacaca aagtgtataa atcttgagta   3840
tatatttaca tgtcttttta aaaagggtcg ttactagaga tttacccatg gggagacgc   3900
ccagggtagc atccgttgct atatattaaa aacaaacgaa cagaaagaaa aaaaaaagga   3960
aaatgttttt taaaaggtca tatatttttt tgctactttt gctgttttat ttttttaaat   4020
tatgttttaa acctatttc agtttaggtt tccctcaata aaaaattgct gctgcttcat   4080
ttttatcctg ggcgtgtgaa aagagagcag gtgtccagcg cagaggaggg agacaggggg   4140
taaagggcca tgagctggtc ttccccctgc cccccatgac ctctgtctcc tggattgtgc   4200
cccagacctc ccagccaagc cttctatctc ccgatgcatt gggaacagca ggagaagact   4260
gaggtcctga gggcagagag ccaagctcgc acacttgatt gtttcctcgg aggagagagt   4320
gagaggatga ggttagccag agggtagaac tggacagaaa cccaaaccct agaccctgta   4380
cattcagatg tcttgtctat cttccccaac ctactcctca tattcctctc ctgtaaatat   4440
cctccccttc cctgttggtc tctgttaccc agttgggtct gtccctgagc ttggcttcct   4500
atagtttttc cttcacaaac tccacccatc cctcaggaaa cagaaaacga tctctttggt   4560
tggggtcaac ttggcaactc aattctgcca cctgctggtt gctttggtac cttggtctct   4620
tattcaaacc cacaccactc aagccttaga gggtttgttt ttgtttttg tttgtttgtt   4680
tggttggttg gttggtcttt tttttctggg tctgctgaat acaaacctgt tcagtatgat   4740
```

```
ttcatctgta ggggttaggg ctgcttcttt aaatgcagtt ttggcagctg tggtttgggt   4800

cattgtcata agagttctta tcgttgtttc tctctgtaca catgtaactg tcaaaatatt   4860

atgaatggtt tttatgctga aagaagacat catttggcaa agagggctag ggaatgaatt   4920

tagcacaaac tcattttctt ggagaccgtg tatcatagtg gttttttttt tttttctttc   4980

tcttgttaaa actgaacatt atttctgc                                      5008


<210> SEQ ID NO 44
<211> LENGTH: 840
<212> TYPE: PRT
<213> ORGANISM: Mus musculus

<400> SEQUENCE: 44

Met Gly Leu Pro Ser Thr Trp Arg Tyr Gly Arg Gly Pro Gly Ile Gly
1               5                   10                  15

Thr Val Thr Met Val Ser Trp Gly Arg Phe Ile Cys Leu Val Leu Val
            20                  25                  30

Thr Met Ala Thr Leu Ser Leu Ala Arg Pro Ser Phe Ser Leu Val Glu
        35                  40                  45

Asp Thr Thr Leu Glu Pro Glu Glu Pro Pro Thr Lys Tyr Gln Ile Ser
    50                  55                  60

Gln Pro Glu Ala Tyr Val Val Ala Pro Gly Glu Ser Leu Glu Leu Gln
65                  70                  75                  80

Cys Met Leu Lys Asp Ala Ala Val Ile Ser Trp Thr Lys Asp Gly Val
                85                  90                  95

His Leu Gly Pro Asn Asn Arg Thr Val Leu Ile Gly Glu Tyr Leu Gln
            100                 105                 110

Ile Lys Gly Ala Thr Pro Arg Asp Ser Gly Leu Tyr Ala Cys Thr Ala
        115                 120                 125

Ala Arg Thr Val Asp Ser Glu Thr Trp Tyr Phe Met Val Asn Val Thr
    130                 135                 140

Asp Ala Ile Ser Ser Gly Asp Asp Glu Asp Asp Thr Asp Ser Ser Glu
145                 150                 155                 160

Asp Val Val Ser Glu Asn Arg Ser Asn Gln Arg Ala Pro Tyr Trp Thr
                165                 170                 175

Asn Thr Glu Lys Met Glu Lys Arg Leu His Ala Val Pro Ala Ala Asn
            180                 185                 190

Thr Val Lys Phe Arg Cys Pro Ala Gly Gly Asn Pro Thr Pro Thr Met
        195                 200                 205

Arg Trp Leu Lys Asn Gly Lys Glu Phe Lys Gln Glu His Arg Ile Gly
    210                 215                 220

Gly Tyr Lys Val Arg Asn Gln His Trp Ser Leu Ile Met Glu Ser Val
225                 230                 235                 240

Val Pro Ser Asp Lys Gly Asn Tyr Thr Cys Leu Val Glu Asn Glu Tyr
                245                 250                 255

Gly Ser Ile Asn His Thr Tyr His Leu Asp Val Val Glu Arg Ser Pro
            260                 265                 270

His Arg Pro Ile Leu Gln Ala Gly Leu Pro Ala Asn Ala Ser Thr Val
        275                 280                 285

Val Gly Gly Asp Val Glu Phe Val Cys Lys Val Tyr Ser Asp Ala Gln
    290                 295                 300

Pro His Ile Gln Trp Ile Lys His Val Glu Lys Asn Gly Ser Lys Tyr
305                 310                 315                 320

Gly Pro Asp Gly Leu Pro Tyr Leu Lys Val Leu Lys Ala Ala Gly Val
```

```
                325                 330                 335

Asn Thr Thr Asp Lys Glu Ile Glu Val Leu Tyr Ile Arg Asn Val Thr
            340                 345                 350

Phe Glu Asp Ala Gly Glu Tyr Thr Cys Leu Ala Gly Asn Ser Ile Gly
        355                 360                 365

Ile Ser Phe His Ser Ala Trp Leu Thr Val Leu Pro Ala Pro Val Arg
    370                 375                 380

Glu Lys Glu Ile Thr Ala Ser Pro Asp Tyr Leu Glu Ile Ala Ile Tyr
385                 390                 395                 400

Cys Ile Gly Val Phe Leu Ile Ala Cys Met Val Val Thr Val Ile Phe
                405                 410                 415

Cys Arg Met Lys Thr Thr Thr Lys Lys Pro Asp Phe Ser Ser Gln Pro
            420                 425                 430

Ala Val His Lys Leu Thr Lys Arg Ile Pro Leu Arg Arg Gln Val Thr
        435                 440                 445

Val Ser Ala Glu Ser Ser Ser Ser Met Asn Ser Asn Thr Pro Leu Val
    450                 455                 460

Arg Ile Thr Thr Arg Leu Ser Ser Thr Ala Asp Thr Pro Met Leu Ala
465                 470                 475                 480

Gly Val Ser Glu Tyr Glu Leu Pro Glu Asp Pro Lys Trp Glu Phe Pro
                485                 490                 495

Arg Asp Lys Leu Thr Leu Gly Lys Pro Leu Gly Glu Gly Cys Phe Gly
            500                 505                 510

Gln Val Val Met Ala Glu Ala Val Gly Ile Asp Lys Asp Lys Pro Lys
        515                 520                 525

Glu Ala Val Thr Val Ala Val Lys Met Leu Lys Asp Asp Ala Thr Glu
    530                 535                 540

Lys Asp Leu Ser Asp Leu Val Ser Glu Met Glu Met Met Lys Met Ile
545                 550                 555                 560

Gly Lys His Lys Asn Ile Ile Asn Leu Leu Gly Ala Cys Thr Gln Asp
                565                 570                 575

Gly Pro Leu Tyr Val Ile Val Glu Tyr Ala Ser Lys Gly Asn Leu Arg
            580                 585                 590

Glu Tyr Leu Arg Ala Arg Arg Pro Pro Gly Met Glu Tyr Ser Tyr Asp
        595                 600                 605

Ile Asn Arg Val Pro Glu Glu Gln Met Thr Phe Lys Asp Leu Val Ser
    610                 615                 620

Cys Thr Tyr Gln Leu Ala Arg Gly Met Glu Tyr Leu Ala Ser Gln Lys
625                 630                 635                 640

Cys Ile His Arg Asp Leu Ala Ala Arg Asn Val Leu Val Thr Glu Asn
                645                 650                 655

Asn Val Met Lys Ile Ala Asp Phe Gly Leu Ala Arg Asp Ile Asn Asn
            660                 665                 670

Ile Asp Tyr Tyr Lys Lys Thr Thr Asn Gly Arg Leu Pro Val Lys Trp
        675                 680                 685

Met Ala Pro Glu Ala Leu Phe Asp Arg Val Tyr Thr His Gln Ser Asp
    690                 695                 700

Val Trp Ser Phe Gly Val Leu Met Trp Glu Ile Phe Thr Leu Gly Gly
705                 710                 715                 720

Ser Pro Tyr Pro Gly Ile Pro Val Glu Glu Leu Phe Lys Leu Leu Lys
                725                 730                 735

Glu Gly His Arg Met Asp Lys Pro Thr Asn Cys Thr Asn Glu Leu Tyr
            740                 745                 750
```

```
Met Met Met Arg Asp Cys Trp His Ala Val Pro Ser Gln Arg Pro Thr
        755                 760                 765

Phe Lys Gln Leu Val Glu Asp Leu Asp Arg Ile Leu Thr Leu Thr Thr
    770                 775                 780

Asn Glu Glu Tyr Leu Asp Leu Thr Gln Pro Leu Glu Gln Tyr Ser Pro
785                 790                 795                 800

Ser Tyr Pro Asp Thr Arg Ser Ser Cys Ser Ser Gly Asp Asp Ser Val
                805                 810                 815

Phe Ser Pro Asp Pro Met Pro Tyr Glu Pro Cys Leu Pro Gln Tyr Pro
            820                 825                 830

His Ile Asn Gly Ser Val Lys Thr
        835                 840


<210> SEQ ID NO 45
<211> LENGTH: 5223
<212> TYPE: DNA
<213> ORGANISM: Mus musculus

<400> SEQUENCE: 45

gatgtgcgga taagtacaat tacctattca cgtgttccct tcctaaagga gggtttccca      60

aacactcgtc ccctgtctat tgttcagagg aacaagacaa cgcaacatct cccacgaaca     120

tccgctgctt ccaccctcaa agcttcatga catgaaatgt ctggccccag tatgctgcag     180

acctattcta aggtgtctga agttgcacag cattctgtca tttgtttcct aacttgacat     240

aaaacaacgt aacgcatcca ctgtgcacca aagctggcta ggaactgggg cagtggcgta     300

cagaggccgt tcaccaacag ggttccgaga ggtcatctgt gcacccctgc gggcagcgcg     360

gcggggcccc tcgcctgcct ggcgggtgtc tctttgcggc tgctaggctt cgggggcagc     420

gcggggctcg ggactgcccc agcgcgaggc gctgattggc agagcgggcg ccgccgtcca     480

ggaaacggct cgggtttcag cggggggcgt gacccgcccg aggaggctgc ggcggcggcg     540

cgggcggcga ggggagagag ccgggagagg cgagcggcgg cggcggcagg cgcggaacgg     600

gcgcacggac gatcgaacgc gcggccgcca gagctccggc gcgggggctg cctgtgtgtt     660

cctggcccgg cgtggcgact gctctccggg ctggcggggg ccgggcgtga gcccccgggc     720

ctcagcgttc ctgagcgctg cgagtgttca ctactcgcca gcaaagtttg gagtaggcaa     780

cgccaagctc cagtcctttc ttctgctgct gcccagatcc gagagcagct ccggtgtcat     840

gtcctagctg ttctgcgatc ccggcgcgc gtgaagcctc ggaaccttgg cgccggctgc      900

tacccaagga atcgttctct ttttggagtt ttcctccgag atcatcgcct gctccatccc     960

gatccactct gggctccggc gcagcaccga gcgcagagga gcgctgccat tcaagtggca    1020

gccacagcag cagcagcagc agcagtggga gcaggaacag cagtaacaac agcaacagca    1080

gcacagccgc ctcagagctt tggctcctga gccccctgtg ggctgaaggc attgcaggta    1140

gcccatggtc tcagaagaag tgtgcagatg ggattaccgt ccacgtggag atatggaaga    1200

ggaccaggga ttggcactgt gaccatggtc agctgggggc gcttcatctg cctggtcttg    1260

gtcaccatgg caaccttgtc cctggcccgg ccctccttca gtttagttga ggataccact    1320

ttagaaccag aagagccacc aaccaaatac caaatctccc aaccagaagc gtacgtggtt    1380

gcccccgggg aatcgctaga gttgcagtgc atgttgaaag atgccgccgt gatcagttgg    1440

actaaggatg gggtgcactt ggggcccaac aataggacag tgcttattgg ggagtatctc    1500

cagataaaag gtgccacacc tagagactcc ggcctctatg cttgtactgc agctaggacg    1560

gtagacagtg aaacttggta cttcatggtg aatgtcacag atgccatctc atctggagat    1620
```

-continued

```
gatgaggacg acacagatag ctccgaagac gttgtcagtg agaacaggag caaccagaga   1680
gcaccgtact ggaccaacac cgagaagatg gagaagcggc tccacgctgt ccctgccgcc   1740
aacactgtga agttccgctg tccggctggg gggaatccaa cgcccacaat gaggtggtta   1800
aaaaacggga aggagtttaa gcaggagcat cgcattggag gctataaggt acgaaaccag   1860
cactggagcc ttattatgga aagtgtggtc ccgtcagaca aaggcaacta cacctgcctg   1920
gtggagaatg aatacgggtc catcaaccac acctaccacc tcgatgtcgt tgaacggtca   1980
ccacaccggc ccatcctcca agctggactg cctgcaaatg cctccacggt ggtcggaggg   2040
gatgtggagt ttgtctgcaa ggtttacagc gatgcccagc cccacatcca gtggatcaag   2100
cacgtggaaa agaacggcag taaatacggg cctgatgggc tgccctacct caaggtcctg   2160
aaggccgccg gtgttaacac cacggacaaa gagattgagg ttctctatat tcggaatgta   2220
acttttgagg atgctgggga atatacgtgc ttggcgggta attctatcgg gatatccttt   2280
cactctgcat ggttgacagt tctgccagcg cctgtgagag agaaggagat cacggcttcc   2340
ccagattatc tggagatagc tatttactgc ataggggtct tcttaatcgc ctgcatggtg   2400
gtgacagtca tcttttgccg aatgaagacc acgaccaaga agccagactt cagcagccag   2460
ccagctgtgc acaagctgac caagcgcatc cccctgcgga gacaggtaac agtttcggcc   2520
gagtccagct cctccatgaa ctccaacacc ccgctggtga ggataacaac gcgtctgtcc   2580
tcaacagcgg acaccccgat gctagcaggg gtctccgagt atgagttgcc agaggatcca   2640
aagtgggaat tccccagaga taagctgacg ctgggcaaac ccctggggga aggttgcttc   2700
gggcaagtag tcatggctga agcagtggga atcgataaag acaaacccaa ggaggcggtc   2760
accgtggcag tgaagatgtt gaaagatgat gccacagaga aggacctgtc tgatctggta   2820
tcagagatgg agatgatgaa gatgattggg aaacataaga acattatcaa cctcctgggg   2880
gcctgcacgc aggatggacc tctctacgtc atagttgaat atgcatcgaa aggcaacctc   2940
cgggaatacc tccgagcccg gaggccacct ggcatggagt actcctatga cattaaccgt   3000
gtccccgagg agcagatgac cttcaaggac ttggtgtcct gcacctacca gctggctaga   3060
ggcatggagt acttggcttc ccaaaaatgt atccatcgag atttggctgc cagaaacgtg   3120
ttggtaacag aaaacaatgt gatgaagata gcagactttg gcctggccag ggatatcaac   3180
aacatagact actataaaaa gaccacaaat gggcgacttc cagtcaagtg gatggctcct   3240
gaagcccttt ttgatagagt ttacactcat cagagcgatg tctggtcctt cggggtgtta   3300
atgtgggaga tctttacttt agggggctca ccctacccag ggattcccgt ggaggaactt   3360
tttaagctgc tcaaagaggg acacaggatg gacaagccca ccaactgcac caatgaactg   3420
tacatgatga tgagggattg ctggcatgct gtaccctcac agagacccac attcaagcag   3480
ttggtcgaag acttggatcg aattctgact ctcacaacca atgaggaata cttggatctc   3540
acccagcctc tcgaacagta ttctcctagt taccccgaca caaggagctc ttgttcttca   3600
ggggacgatt ctgtgttttc tccagacccc atgccttatg aaccctgtct gcctcagtat   3660
ccacacataa acggcagtgt taaaacatga gtgaatgtgt cttcctgtcc ccaaacagga   3720
cagcaccagg aacctactta cactgagcag agaggctgtg cctccagagc ctgtgacacg   3780
cctccacttg tatatatgga tcagaggagt aaatagtggg aagcatattt gtcacgtgtg   3840
taaagattta tacagttgga aacatgttac ctaaccagga aaggaagact gtttcctgat   3900
aagtggacag ccgcaagcca ccatgccacc ctctctgacc caccatgtat gctggctgtg   3960
ccccagttgg actcaaggca gacaggtgtt ctgccttcct tgttaatttt gtaataattg   4020
```

```
gagaagatat atgtcagcac acacttacag agcacaaacg cagtatatag gtgctggatg   4080

tatgtaaata tattcaaatt atgtataaat atatattata tatttacaag gaattatttt   4140

ttgtattgat tttaaatgga tgtcctgatg cacctagaaa attggtctct cttttttta   4200

aatagatatt tgctaaatgc tgttcttaga gtttcttaat tttcaccgag cagaggtggg   4260

aaaatacttt tgctttcagg gaaaatggtg tcacattaat ttattaacga attggtaata   4320

tacgaaacga ttaatcatct atagtttttt tttttttgta atttaagtgg catttctatg   4380

caggcagcac ggaggactag ttaatctatt gcttggactt aactggttat tggatccttt   4440

gagaagagaa atatttacga tatatgacta atttgggggg aaatggtgtt ttgatttatt   4500

tgtgtttcaa ctctgctgtc cgatgagcat gtctagacac cctaatgccc atgtttcaag   4560

aaacctgtta aactctgtca ccccaggta acaattaacc agacttccca agacaaatgg   4620

taccagcatc ctcatcccaa gatgccttaa tccacttctc tggagaacag acttccatgg   4680

gaatgatagc agggtcctct cgtccggcag ctggccttct gcccgggtta cacattcatc   4740

acgtttgcct tgcttctcag tgagttttaa taacagcttc agattcttca gcaccaagag   4800

ccctttgggg aatctccatc ctctcgaagg atggcaaaag cccagcatca ttcggttgag   4860

agtctgggac ctccttccat cttcttaagg gtttgcttct ggcttctacc cacttctgac   4920

aagacctcac ctcacaaaaa gatctggcct aatagctaca tccgacaaga taacgcttat   4980

tgttgatttc cgtattcaag tattgttttg ctttggatac gcccactcac tttgctacag   5040

tcatgcgaca tgtatgcaga ttacactgat tttatgtgtt ttggaattgg agaaagtatt   5100

taataaaacc tgttaatttt tatactgaca ataaaaatgt ttctacagat attaatgtta   5160

acaagacaaa ataaatgtca cgcagcttat ttttttaaaa aaaaaaaaaa aaaaaaaaaa   5220

aaa                                                                 5223
```

```
<210> SEQ ID NO 46
<211> LENGTH: 800
<212> TYPE: PRT
<213> ORGANISM: Mus musculus

<400> SEQUENCE: 46

Met Val Val Pro Ala Cys Val Leu Val Phe Cys Val Ala Val Val Ala
1               5                   10                  15

Gly Ala Thr Ser Glu Pro Pro Gly Pro Glu Gln Arg Val Val Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160
```

```
Pro Ala Ala Asn Thr Val Arg Phe Arg Cys Pro Ala Ala Gly Asn Pro
                165                 170                 175

Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Val Gly Pro Asp Gly Thr Pro Tyr Val Thr Val Leu Lys
    290                 295                 300

Thr Ala Gly Ala Asn Thr Thr Asp Lys Glu Leu Glu Val Leu Ser Leu
305                 310                 315                 320

His Asn Val Thr Phe Glu Asp Ala Gly Glu Tyr Thr Cys Leu Ala Gly
                325                 330                 335

Asn Ser Ile Gly Phe Ser His His Ser Ala Trp Leu Val Val Leu Pro
            340                 345                 350

Ala Glu Glu Glu Leu Met Glu Thr Asp Glu Ala Gly Ser Val Tyr Ala
        355                 360                 365

Gly Val Leu Ser Tyr Gly Val Val Phe Phe Leu Phe Ile Leu Val Val
    370                 375                 380

Ala Ala Val Ile Leu Cys Arg Leu Arg Ser Pro Pro Lys Lys Gly Leu
385                 390                 395                 400

Gly Ser Pro Thr Val His Lys Val Ser Arg Phe Pro Leu Lys Arg Gln
                405                 410                 415

Val Ser Leu Glu Ser Asn Ser Ser Met Asn Ser Asn Thr Pro Leu Val
            420                 425                 430

Arg Ile Ala Arg Leu Ser Ser Gly Glu Gly Pro Val Leu Ala Asn Val
        435                 440                 445

Ser Glu Leu Glu Leu Pro Ala Asp Pro Lys Trp Glu Leu Ser Arg Thr
    450                 455                 460

Arg Leu Thr Leu Gly Lys Pro Leu Gly Glu Gly Cys Phe Gly Gln Val
465                 470                 475                 480

Val Met Ala Glu Ala Ile Gly Ile Asp Lys Asp Arg Thr Ala Lys Pro
                485                 490                 495

Val Thr Val Ala Val Lys Met Leu Lys Asp Asp Ala Thr Asp Lys Asp
            500                 505                 510

Leu Ser Asp Leu Val Ser Glu Met Glu Met Met Lys Met Ile Gly Lys
        515                 520                 525

His Lys Asn Ile Ile Asn Leu Leu Gly Ala Cys Thr Gln Gly Gly Pro
    530                 535                 540

Leu Tyr Val Leu Val Glu Tyr Ala Ala Lys Gly Asn Leu Arg Glu Phe
545                 550                 555                 560

Leu Arg Ala Arg Arg Pro Pro Gly Met Asp Tyr Ser Phe Asp Ala Cys
                565                 570                 575

Arg Leu Pro Glu Glu Gln Leu Thr Cys Lys Asp Leu Val Ser Cys Ala
            580                 585                 590
```

```
Tyr Gln Val Ala Arg Gly Met Glu Tyr Leu Ala Ser Gln Lys Cys Ile
        595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Val Leu Leu Trp Glu Ile Phe Thr Leu Gly Gly Ser Pro
        675                 680                 685

Tyr Pro Gly Ile Pro Val Glu Glu Leu Phe Lys Leu Leu Lys Glu Gly
    690                 695                 700

His Arg Met Asp Lys Pro Ala Ser Cys Thr His Asp Leu Tyr Met Ile
705                 710                 715                 720

Met Arg Glu Cys Trp His Ala Val Pro Ser Gln Arg Pro Thr Phe Lys
                725                 730                 735

Gln Leu Val Glu Asp Leu Asp Arg Ile Leu Thr Val Thr Ser Thr Asp
            740                 745                 750

Glu Tyr Leu Asp Leu Ser Val Pro Phe Glu Gln Tyr Ser Pro Gly Gly
        755                 760                 765

Gln Asp Thr Pro Ser Ser Ser Ser Ser Gly Asp Asp Ser Val Phe Thr
    770                 775                 780

His Asp Leu Leu Pro Pro Gly Pro Pro Ser Asn Gly Gly Pro Arg Thr
785                 790                 795                 800
```

```
<210> SEQ ID NO 47
<211> LENGTH: 4232
<212> TYPE: DNA
<213> ORGANISM: Mus musculus

<400> SEQUENCE: 47

tcggggcgtg gcgggagcac cccccaaccc ccgcccgggc tgctgcgcgc cgggcagccc      60

cagttcagtg cactgtggca gcgggggtgg cgggagcagc tggcgccgtg cgatccactc     120

cggcgggggg actcagtggt gggcggccgg ccactgggac agaggagacc ctggaaaagc     180

gggccgagag acggagccgc gcgtgtctcc acagaggcgt tctcccaccg gcgccggagc     240

cgggcgtggg gggttgcagc atgcccgcgc gcgctgcttg aggacgccgc ggcccccgct     300

ctggagccat ggtagtcccg gcctgcgtgc tagtgttctg cgtggcggtc gtggctggag     360

ctacttccga gcctcctggt ccagagcagc gagttgtgcg gagagcggca gaggttccag     420

ggcctgaacc tagccagcag gagcaggtgg ccttcggcag tggggacacc gtggagctga     480

gctgccatcc tcctggaggt gccccccacag ggcccacggt ctgggctaag gatggtacag     540

gtctggtggc ctcccaccgc atcctggtgg ggcctcagag gctgcaagtg ctaaatgcct     600

cccacgaaga tgcaggggtc tacagctgcc agcaccggct cactcggcgt gtgctgtgcc     660

acttcagtgt gcgtgtaaca gatgctccat cctcaggaga tgacgaagat ggggaggacg     720

tggctgaaga cacaggggct ccttattgga ctcgcccgga gcgaatggat aagaaactgc     780

tggctgtgcc agccgcaaac actgtccgct tccgctgccc agctgctggc aaccctaccc     840

cctccatctc ctggctgaag aatggcaaag aattccgagg ggagcatcgc attgggggca     900

tcaagctccg gcaccagcag tggagcttgg tcatggaaag tgtggtaccc tccgatcgtg     960
```

```
gcaactatac ctgtgtagtt gagaacaagt ttggcagcat ccggcagaca tacacactgg   1020

atgtgctgga gcgctcccca caccggccca tcctgcaggc tgggctgccg gccaaccaga   1080

cagccattct aggcagtgac gtggagttcc actgcaaggt gtacagcgat gcacagccac   1140

acatccagtg gctgaagcac gtggaagtga acggcagcaa ggtgggccct gacggcacgc   1200

cctacgtcac tgtactcaag actgcaggcg ctaacaccac cgacaaggag ctagaggttc   1260

tgtccttgca caatgtcacc tttgaggacg cgggggagta cacctgcctg gcgggcaatt   1320

ctattgggtt ttcccatcac tctgcgtggc tggtggtgct gccagctgag gaggagctga   1380

tggaaactga tgaggctggc agcgtgtacg caggcgtcct cagctacggg gtggtcttct   1440

tcctcttcat cctggtggtg gcagctgtga tactctgccg cctgcgcagt cccccaaaga   1500

agggcttggg ctcgcccacc gtgcacaagg tctctcgctt cccgcttaag cgacaggtgt   1560

ccttggaatc taactcctct atgaactcca acacacccct tgtccggatt gcccggctgt   1620

cctcaggaga aggtcctgtt ctggccaatg tttctgaact tgagctgcct gctgacccca   1680

agtgggagct atccaggacc cggctgacac ttggtaagcc tcttggagaa ggctgctttg   1740

gacaggtggt catggcagaa gctattggca tcgacaagga ccgtactgcc aagcctgtca   1800

ccgtggccgt gaagatgctg aaagatgatg cgactgacaa ggacctgtcg gacctggtat   1860

ctgagatgga gatgatgaaa atgattggca agcacaagaa catcattaac ctgctggggg   1920

cgtgcacaca gggtgggccc ctgtatgtgc tggtggagta cgcagccaag ggcaatctcc   1980

gggagttcct tcgggcgcgg cggcctccag gcatggacta ctcctttgat gcctgcaggc   2040

tgccagagga acagctcacc tgcaaggatc tagtgtcctg tgcctaccag gtggcacggg   2100

gcatggaata cttggcttct cagaagtgta ttcacagaga cttggctgcc agaaacgtcc   2160

tggtgaccga ggacaatgtg atgaagattg cggactttgg cctggctcga gatgtgcaca   2220

acctggacta ctacaagaag accacaaatg gccggctacc tgtgaagtgg atggcaccag   2280

aggccctttt tgaccgagtc tacacccacc agagtgatgt ttggtctttt ggtgtcctcc   2340

tctgggagat ctttacgctg gggggctcac cgtatcctgg catcccagtg gaagagcttt   2400

tcaagctgtt gaaagagggc caccgcatgg acaagccagc cagctgcaca catgacctgt   2460

acatgatcat gcgggaatgt tggcatgcgg tgccttcaca gaggcccacc ttcaagcagt   2520

tggtagagga tttagaccgc atcctcactg tgacatcaac cgacgagtac ttggacctct   2580

ccgtgccgtt tgagcagtac tcgccaggtg gccaggacac gcctagctcc agctcgtccg   2640

gagatgactc ggtgttcacc catgacctgc taccccaggt ccacccagt aacgggggac    2700

ctcggacgtg aagggccaac agtcccacag accaagcccc aggcaatgtt tacgcggacc   2760

ctagcccgcc ctgctactgc tggtgtgcag tggaccctag ccagcccagt gcaatgggcc   2820

aacagtagac aagacttcct gcgtgtttat ccttggctcc tgggtgcaga ggccccttgg   2880

gaacatgcac tgctgtagag taatctcctg actggccagg gccaggagca ccaaacaaga   2940

atgtaagagg cccaccctgt gcaaccctgg ggttctggcc ctctcatttc ccactgctac   3000

cttccaggga ccattgtgga gagggctaga ctccatgtcc agagtgggcc ttggccttct   3060

tggtgcccca agctgagcct acagggaggc tctgctctgt gtggcaaacc tctctcctac   3120

atggcacctt gtgcctgggg gtgtcatagc tcgacatctc caggctgcct gctttccacc   3180

ctgcccctca gagacaaatt acgggtacct gaaggggggg cataatgtct atcagaaagg   3240

tttattccag aggaaaatgt acatttatat aaatagatgt tgtgtatgat ataaatatat   3300

acatacatat atataagaat atctatatgg aaaaaggcaa agttgaggcc caagggagca   3360
```

```
agatactcca tgggtctcac taggaaactg gcaagagcag gctgagaagc aaggggcttt   3420

tctggcacgg cagttttgtt tgtactggac ctgtatattt gtaaagctat ttatcaaccc   3480

ccagagcgcc agtccccgac cccaggttca tagcgtttag tcccagggta ttgcagccat   3540

cttaagttgt aacttattaa cagcggaaga ggttcatgct ggatttaggg aattgctgag   3600

aacgtgcgtc tggcctccac caggctggcc gtggcccctt ggcgcttgaa tggctctcct   3660

agtcagagct ggctccaggg agcattttct gttgcctttg gccctctttt gtgggggatt   3720

agatttatat aggaactttc tttaggagat gtttaaaaat tttaaggtga actggtattt   3780

ttcatacaga ttattctaat tgctatgtat tccaggcagg agcctgtgcc cagggaaggg   3840

ctggccctgc aagaaggttc agatgttaat agttatctgt tacaagttta tctatctata   3900

atttattgag tttttacaag ttgttttgct gtaggcttaa cacttcctat gcagtgcttc   3960

tagactttta tagcctagac tgctaccttt caaagcttgg gagacagtgg tgaatgcaat   4020

tttgttactt ttgtactgtc actgggccct aggcttgggt ggctgtccct tgcctgtcaa   4080

ccagcagggt caggacagtg gctcagggtg actttcttgg ggcctagcac atggtttgtc   4140

agcccacact ggcagatgtg gttttgttaa cacaaccaac ttactttcca aaaaataaag   4200

agataactgg ttccaaaaaa aaaaaaaaaa aa                                 4232
```

<210> SEQ ID NO 48
<211> LENGTH: 799
<212> TYPE: PRT
<213> ORGANISM: Mus musculus

<400> SEQUENCE: 48

```
Met Trp Leu Leu Leu Ala Leu Leu Ser Ile Phe Gln Gly Thr Pro Ala
1               5                   10                  15

Leu Ser Leu Glu Ala Ser Glu Glu Met Glu Gln Glu Pro Cys Leu Ala
            20                  25                  30

Pro Ile Leu Glu Gln Gln Glu Gln Val Leu Thr Val Ala Leu Gly Gln
        35                  40                  45

Pro Val Arg Leu Cys Cys Gly Arg Thr Glu Arg Gly Arg His Trp Tyr
    50                  55                  60

Lys Glu Gly Ser Arg Leu Ala Ser Ala Gly Arg Val Arg Gly Trp Arg
65                  70                  75                  80

Gly Arg Leu Glu Ile Ala Ser Phe Leu Pro Glu Asp Ala Gly Arg Tyr
                85                  90                  95

Leu Cys Leu Ala Arg Gly Ser Met Thr Val Val His Asn Leu Thr Leu
            100                 105                 110

Leu Met Asp Asp Ser Leu Thr Ser Ile Ser Asn Asp Glu Asp Pro Lys
        115                 120                 125

Thr Leu Ser Ser Ser Ser Ser Gly His Val Tyr Pro Gln Gln Ala Pro
    130                 135                 140

Tyr Trp Thr His Pro Gln Arg Met Glu Lys Lys Leu His Ala Val Pro
145                 150                 155                 160

Ala Gly Asn Thr Val Lys Phe Arg Cys Pro Ala Ala Gly Asn Pro Met
                165                 170                 175

Pro Thr Ile His Trp Leu Lys Asp Gly Gln Ala Phe His Gly Glu Asn
            180                 185                 190

Arg Ile Gly Gly Ile Arg Leu Arg His Gln His Trp Ser Leu Val Met
        195                 200                 205

Glu Ser Val Val Pro Ser Asp Arg Gly Thr Tyr Thr Cys Leu Val Glu
    210                 215                 220
```

```
Asn Ser Leu Gly Ser Ile Arg Tyr Ser Tyr Leu Leu Asp Val Leu Glu
225                 230                 235                 240

Arg Ser Pro His Arg Pro Ile Leu Gln Ala Gly Leu Pro Ala Asn Thr
                245                 250                 255

Thr Ala Val Val Gly Ser Asp Val Glu Leu Leu Cys Lys Val Tyr Ser
            260                 265                 270

Asp Ala Gln Pro His Ile Gln Trp Leu Lys His Val Val Ile Asn Gly
        275                 280                 285

Ser Ser Phe Gly Ala Asp Gly Phe Pro Tyr Val Gln Val Leu Lys Thr
    290                 295                 300

Thr Asp Ile Asn Ser Ser Glu Val Glu Val Leu Tyr Leu Arg Asn Val
305                 310                 315                 320

Ser Ala Glu Asp Ala Gly Glu Tyr Thr Cys Leu Ala Gly Asn Ser Ile
                325                 330                 335

Gly Leu Ser Tyr Gln Ser Ala Trp Leu Thr Val Leu Pro Glu Glu Asp
            340                 345                 350

Leu Thr Trp Thr Thr Ala Thr Pro Glu Ala Arg Tyr Thr Asp Ile Ile
        355                 360                 365

Leu Tyr Val Ser Gly Ser Leu Val Leu Leu Val Leu Leu Leu Leu Ala
    370                 375                 380

Gly Val Tyr His Arg Gln Val Ile Arg Gly His Tyr Ser Arg Gln Pro
385                 390                 395                 400

Val Thr Ile Gln Lys Leu Ser Arg Phe Pro Leu Ala Arg Gln Phe Ser
                405                 410                 415

Leu Glu Ser Arg Ser Ser Gly Lys Ser Ser Leu Ser Leu Val Arg Gly
            420                 425                 430

Val Arg Leu Ser Ser Ser Gly Pro Pro Leu Leu Thr Gly Leu Val Asn
        435                 440                 445

Leu Asp Leu Pro Leu Asp Pro Leu Trp Glu Phe Pro Arg Asp Arg Leu
    450                 455                 460

Val Leu Gly Lys Pro Leu Gly Glu Gly Cys Phe Gly Gln Val Val Arg
465                 470                 475                 480

Ala Glu Ala Phe Gly Met Asp Pro Ser Arg Pro Asp Gln Thr Ser Thr
                485                 490                 495

Val Ala Val Lys Met Leu Lys Asp Asn Ala Ser Asp Lys Asp Leu Ala
            500                 505                 510

Asp Leu Val Ser Glu Met Glu Val Met Lys Leu Ile Gly Arg His Lys
        515                 520                 525

Asn Ile Ile Asn Leu Leu Gly Val Cys Thr Gln Glu Gly Pro Leu Tyr
    530                 535                 540

Val Ile Val Glu Cys Ala Ala Lys Gly Asn Leu Arg Glu Phe Leu Arg
545                 550                 555                 560

Ala Arg Arg Pro Pro Gly Pro Asp Leu Ser Pro Asp Gly Pro Arg Ser
                565                 570                 575

Ser Glu Gly Pro Leu Ser Phe Pro Ala Leu Val Ser Cys Ala Tyr Gln
            580                 585                 590

Val Ala Arg Gly Met Gln Tyr Leu Glu Ser Arg Lys Cys Ile His Arg
        595                 600                 605

Asp Leu Ala Ala Arg Asn Val Leu Val Thr Glu Asp Asp Val Met Lys
    610                 615                 620

Ile Ala Asp Phe Gly Leu Ala Arg Gly Val His His Ile Asp Tyr Tyr
625                 630                 635                 640

Lys Lys Thr Ser Asn Gly Arg Leu Pro Val Lys Trp Met Ala Pro Glu
                645                 650                 655
```

```
Ala Leu Phe Asp Arg Val Tyr Thr His Gln Ser Asp Val Trp Ser Phe
            660                 665                 670

Gly Ile Leu Leu Trp Glu Ile Phe Thr Leu Gly Gly Ser Pro Tyr Pro
        675                 680                 685

Gly Ile Pro Val Glu Glu Leu Phe Ser Leu Leu Arg Glu Gly His Arg
    690                 695                 700

Met Glu Arg Pro Pro Asn Cys Pro Ser Glu Leu Tyr Gly Leu Met Arg
705                 710                 715                 720

Glu Cys Trp His Ala Ala Pro Ser Gln Arg Pro Thr Phe Lys Gln Leu
                725                 730                 735

Val Glu Ala Leu Asp Lys Val Leu Leu Ala Val Ser Glu Glu Tyr Leu
            740                 745                 750

Asp Leu Arg Leu Thr Phe Gly Pro Phe Ser Pro Ser Asn Gly Asp Ala
        755                 760                 765

Ser Ser Thr Cys Ser Ser Ser Asp Ser Val Phe Ser His Asp Pro Leu
    770                 775                 780

Pro Leu Glu Pro Ser Pro Phe Pro Phe Ser Asp Ser Gln Thr Thr
785                 790                 795


<210> SEQ ID NO 49
<211> LENGTH: 3146
<212> TYPE: DNA
<213> ORGANISM: Mus musculus

<400> SEQUENCE: 49

gacattcctg gctcttcggc ccggggcgga ggagctccgg gcgggtgagt gtgccagccc     60

tgccgggatc gtgacccgcg cgcgcgggag ccgggcggcg gaggagccag gaaggtggtc    120

agtgggaagt ctggccctga tcctgagatc agctggaagg aaatgtggct gctcttggcc    180

ctgttgagca tctttcaggg gacaccagct ttgtcccttg aggcctctga ggaaatggag    240

caggagccct gcctagcccc aatcctggag cagcaagagc aggtgttgac ggtggccctg    300

gggcagcctg tgaggctgtg ctgtgggcgc accgagcgtg gtcgtcactg gtacaaagag    360

ggcagccgcc tagcatctgc tgggcgagta cggggttgga gaggccgcct ggagatcgcc    420

agcttccttc ctgaggatgc tggccgatac ctctgcctgg cccgtggctc catgaccgtc    480

gtacacaatc ttacgttgct tatggatgac tccttaacct ccatcagtaa tgatgaagac    540

cccaagacac tcagcagctc ctcgagtggt catgtctacc cacagcaagc accctactgg    600

acacaccccc aacgcatgga gaagaaactg catgcagtgc ctgccgggaa tactgtcaaa    660

ttccgctgtc cagctgcagg gaaccccatg cctaccatcc actggctcaa ggatggacag    720

gccttccacg gggagaatcg tattggaggc attcggctgc gccaccaaca ctggagcctg    780

gtgatggaaa gtgtggtacc ctcggaccgt ggcacataca catgccttgt ggagaactct    840

ctgggtagca ttcgctacag ctatctcctg gatgtgctgg agcggtcccc gcaccggccc    900

atcctgcagg cggggctccc agccaacacc acagctgtgg ttggcagcga tgtggagcta    960

ctctgcaagg tgtacagcga cgcccagccc cacatacagt ggctgaaaca cgtcgtcatc   1020

aacggcagca gcttcggcgc cgacggtttc ccctacgtac aagtcctgaa gacaacagac   1080

atcaatagct cggaggtaga ggtcttgtat ctgaggaacg tgtccgctga ggatgcagga   1140

gagtatacct gtctggcggg caactccatc ggcctttcct accagtcagc gtggctcacg   1200

gtgctgccag aggaagacct cacgtggaca acagcaaccc ctgaggccag atacacagat   1260

atcatcctgt atgtatcagg ctcactggtt ctgcttgtgc tcctgctgct ggccggggtg   1320
```

```
tatcatcggc aagtcatccg tggccactac tctcgccagc ctgtcactat acaaaagctg   1380
tcccgtttcc ctttggcccg acagttctct ttggagtcga ggtcctctgg caagtcaagt   1440
ttgtccctgg tgcgaggtgt ccgtctctcc tccagcggcc cgcccttgct cacgggcctt   1500
gtgaatctag acctgcctct cgatccgctt tgggaattcc cccgggacag gttggtgctc   1560
ggaaagcccc tgggtgaggg ctgctttggg caagtggttc gtgcagaggc ctttggtatg   1620
gatccctccc ggcccgacca aaccagcacc gtggctgtga agatgctgaa agacaatgcc   1680
tccgacaagg atttggcaga cctggtctcc gagatggagg tgatgaagct aatcggaaga   1740
cacaagaaca tcatcaacct gctgggtgtc tgcactcagg aagggcccct gtacgtgatt   1800
gtggaatgtg ccgccaaggg aaaccttcgg gaattcctcc gtgcccggcg ccccccaggc   1860
cctgatctca gccctgatgg acctcggagc agcgaaggac cactctcctt cccggcccta   1920
gtctcctgtg cctaccaggt ggcccgaggc atgcagtatc tggagtctcg gaagtgcatc   1980
caccgggacc tggctgcccg aaatgtgctg gtgaccgagg atgatgtgat gaagatcgct   2040
gactttgggc tggcacgtgg tgtccaccac attgactact ataagaaaac cagcaacggc   2100
cgcctgccag tcaaatggat ggctccagag gcattgttcg accgcgtgta cacacaccag   2160
agtgacgtgt ggtctttcgg gatcctgctg tgggaaatct tcaccctcgg gggctcccca   2220
taccctggca ttccggtgga ggagctcttc tcactgctgc gagaggggca caggatggag   2280
cggcccccaa actgcccctc agagctgtat gggctaatga gggagtgctg gcacgcagcc   2340
ccatctcaga ggcctacttt taagcagctg gtggaagctc tggacaaggt cctgctggct   2400
gtctctgaag agtaccttga cctccgcctg acctttggac ccttttctcc ctccaatggg   2460
gatgccagca gcacctgctc ctccagtgac tcggttttca gccacgaccc tttgcccctc   2520
gagccaagcc ccttcccttt ctctgactcg cagacgacat gagccgggga gcagcaatgt   2580
tgtatgggct acgcggccca tggccgtggg tctcctcgct gagctgcaac ctgatgcatc   2640
gacatttaat gttggcagtg tcaggcctct gacttgagac tactgctgtc gcagatcctc   2700
tctctggccc tgttttgggg agggccattc ttggtcctaa ggttcatagt tgaggccttc   2760
tgttccagcc ttatgctccc atctcagagt tcaactctca tctcaagatc atggccttgc   2820
ccttggactc atcctcagag aagttaagca ttaaggcctt ggcacgcagc ctccgtctcc   2880
ggggctctcc gggactagct gcaaaactta tgctctaaac atttctagtt cccccaaaca   2940
acctagaggc cttgggactt cacatccccc agcacacaag cctcaccacc ccctgccatc   3000
ccccctccat tgcttgttcc agcatcttgg tgaaaggggc atcagctctg gtgtccctga   3060
gagacgagaa gcctgtggga acgacagaag aacatggcat ttttataaat tatttttttg   3120
aaataaatct ctgtgtgcct ggtggc                                        3146
```

<210> SEQ ID NO 50
<211> LENGTH: 158
<212> TYPE: PRT
<213> ORGANISM: Gallus gallus

<400> SEQUENCE: 50

```
Met Ala Ala Gly Ala Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
```

```
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140

Gly Gln Lys Ala Ile Leu Phe Leu Pro Met Ser Ala Lys Ser
145                 150                 155


<210> SEQ ID NO 51
<211> LENGTH: 574
<212> TYPE: DNA
<213> ORGANISM: Gallus gallus

<400> SEQUENCE: 51

gaggctggac ggccgcggca gggggcgagc ccgcccggcg ctggcggcgg cggccggcgg     60

gggcccgggg cggcggggag ccgccggggc ccggcgcatg gcggcggggg cggcggggag    120

catcaccacg ctgccggcgc tgcccgacga cgggggcggc ggcgcttttc cccccgggca    180

cttcaaggac cccaagcggc tctactgcaa gaacggcggc ttcttcctgc gcatcaaccc    240

cgacggcagg gtggacggcg tccgcgagaa gagcgatccg cacatcaaac tgcagcttca    300

agcagaagaa agaggagtag tatcaatcaa aggcgtaagt gcaaaccgct ttctggctat    360

gaaggaggat ggcagattgc tggcactgaa atgtgcaaca gaggaatgtt tctttttcga    420

gcgcttggaa tctaataact ataacactta ccggtcacgg aagtactctg attggtatgt    480

ggcactgaaa aggactggac agtacaagcc cggaccaaaa actggacctg gacagaaagc    540

tatccttttt cttccaatgt ctgctaaaag ctga                                574


<210> SEQ ID NO 52
<211> LENGTH: 819
<212> TYPE: PRT
<213> ORGANISM: Gallus gallus

<400> SEQUENCE: 52

Met Phe Thr Trp Arg Cys Leu Ile Leu Trp Ala Val Leu Val Thr Ala
1               5                   10                  15

Thr Leu Ser Ala Ala Arg Pro Ala Pro Thr Leu Pro Asp Gln Ala Leu
            20                  25                  30

Pro Lys Ala Asn Ile Glu Val Glu Ser His Ser Ala His Pro Gly Asp
        35                  40                  45

Leu Leu Gln Leu Arg Cys Arg Leu Arg Asp Asp Val Gln Ser Ile Asn
    50                  55                  60

Trp Val Arg Asp Gly Val Gln Leu Pro Glu Asn Asn Arg Thr Arg Ile
65                  70                  75                  80

Thr Gly Glu Glu Val Glu Val Arg Asp Ala Val Pro Glu Asp Ser Gly
                85                  90                  95

Leu Tyr Ala Cys Met Thr Asn Ser Pro Ser Gly Ser Glu Thr Thr Tyr
            100                 105                 110

Phe Ser Val Asn Val Ser Asp Ala Leu Pro Ser Ala Glu Asp Asp Asp
        115                 120                 125
```

```
Asp Glu Asp Asp Ser Ser Ser Glu Glu Lys Glu Ala Asp Asn Thr Lys
    130                 135                 140

Pro Asn Gln Ala Val Ala Pro Tyr Trp Thr Tyr Pro Glu Lys Met Glu
145                 150                 155                 160

Lys Lys Leu His Ala Val Pro Ala Ala Lys Thr Val Lys Phe Lys Cys
                165                 170                 175

Pro Ser Gly Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Lys Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Val Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Ile Ser His His Ser Ala
            340                 345                 350

Trp Leu Thr Val Leu Glu Ala Thr Glu Gln Ser Pro Ala Met Met Thr
        355                 360                 365

Ser Pro Leu Tyr Leu Glu Ile Ile Ile Tyr Cys Thr Gly Ala Phe Leu
    370                 375                 380

Ile Ser Cys Met Val Val Thr Val Ile Ile Tyr Lys Met Lys Ser Thr
385                 390                 395                 400

Thr Lys Lys Thr Asp Phe Asn Ser Gln Leu Ala Val His Lys Leu Ala
                405                 410                 415

Lys Ser Ile Pro Leu Arg Arg Gln Val Thr Val Ser Ala Asp Ser Ser
            420                 425                 430

Ser Ser Met Asn Ser Gly Val Met Leu Val Arg Pro Ser Arg Leu Ser
        435                 440                 445

Ser Ser Gly Thr Pro Met Leu Ala Gly Val Ser Glu Tyr Glu Leu Pro
    450                 455                 460

Glu Asp Pro Arg Trp Glu Leu Pro Arg Asp Arg Leu Ile Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560
```

```
Tyr Ala Ser Lys Gly Asn Leu Arg Glu Tyr Leu Gln Ala Arg Arg Pro
                565                 570                 575

Pro Gly Met Glu Tyr Cys Tyr Asn Pro Thr Arg Ile Pro Glu Glu Gln
            580                 585                 590

Leu Ser Phe Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Met Thr Ser Asn Gln Glu Tyr Leu Asp Leu Ser
        755                 760                 765

Val Pro Leu Asp Gln Tyr Ser Pro Gly Phe Pro Ala Thr Arg Ser Ser
    770                 775                 780

Thr Cys Ser Ser Gly Glu Asp Ser Val Phe Ser His Asp Pro Leu Pro
785                 790                 795                 800

Asp Glu Pro Cys Leu Pro Arg Cys Pro Pro His Ser His Gly Ala Leu
                805                 810                 815

Lys Arg His


<210> SEQ ID NO 53
<211> LENGTH: 2925
<212> TYPE: DNA
<213> ORGANISM: Gallus gallus

<400> SEQUENCE: 53

cgccccatgg aggggcggtt gagcgcagtc gctgagcagt agccgcagca gtgggatgtt      60

tacctggagg tgcctcatcc tttgggctgt gctggtcaca gccacgctgt ctgctgccag     120

accggccccc acgctgcccg accaagctct gcccaaagcg aacatcgagg tggagtccca     180

ctcggcgcac cccggcgatc tcctccagct gcgctgccgg ctgcgcgatg acgtgcagag     240

catcaactgg gtgcgtgatg gagtgcagct gcccgagaac aaccgcacgc gcatcaccgg     300

cgaggaggta gaggtgcggg acgcggtgcc cgaggactcg gggctctatg cctgcatgac     360

caacagcccc tcggggagcg agaccaccta cttctccgtc aacgtctcag acgcactccc     420

ttctgcagag gatgatgatg atgaagatga ttcctcctcg gaggagaagg aggcggataa     480

caccaagccg aaccaggctg tagctcctta ctggacctat cccgagaaga tggagaagaa     540

gctgcatgcc gtccccgctg ccaaaacagt gaaattcaag tgcccctcag gtgggacgcc     600

caaccccacg ctgcgctggc tgaagaacgg caaggagttc aagcctgacc accgcatcgg     660
```

```
gggggtacaag gtccgctatg ccacctggag catcatcatg gactcggtgg tgccatcaga    720
taagggcaac tacacgtgca tcgtggagaa caaatacggg agcatcaacc acacctacca    780
gctggatgtc gtggagcgct ccccgcatcg gcccatcctg caggcagggc tccccgccaa    840
caaaacggtg gccctgggca gcaacgtgga gtttgtctgc aaggtctaca gcgacccgca    900
gccccacatc cagtggctga aacacatcga ggtgaacggc agcaagatcg gccccgacaa    960
cttgccctac gtgcagatcc tgaagacggc tggcgttaac acgacagaca aagagatgga   1020
agtccttcac ttaaggaatg tctcatttga ggatgctggg gagtatacat gtttggcggg   1080
taattctatt gggatctccc atcactctgc atggttgaca gttctcgaag ctactgagca   1140
gtcaccagcc atgatgacgt ccccctcta cctggagatc atcatttact gcaccggcgc   1200
cttcctcatc tcctgcatgg tggtgacagt catcatctac aagatgaaga gcaccaccaa   1260
gaagacagac ttcaacagcc agctggccgt gcacaagctg gccaagagca tcccactgcg   1320
cagacaggta acagtgtcag cagattccag ctcctccatg aactcgggtg tgatgttggt   1380
gcggccctca cggctctcct ccagcggaac cccatgctg gccggcgtct ccgagtatga   1440
gctgcccgag gacccgcgct gggagctgcc acgggacagg ctgatcctgg gcaagccgct   1500
gggagaaggc tgctttgggc aggtggtgct ggcggaggcc atcggcctgg acaaggacaa   1560
gccaaaccgc gtcaccaaag tggctgtaaa gatgctcaag tccgatgcca cagagaagga   1620
cctgtccgac ctcatctccg agatggagat gatgaagatg atcggcaagc acaagaacat   1680
catcaacctg ctgggtgcct gcacgcagga cgggcccctc tatgtcatcg tggagtacgc   1740
cagcaaaggc aacctgcgtg agtacctgca ggcacgccgc ccaccgggca tggagtactg   1800
ctacaacccc acacgcatcc ccgaggagca gctctccttc aaggacctgg tgtcctgtgc   1860
gtaccaggtg gcgcgcggca tggagtacct ggcctccaaa aagtgcatcc acagggacct   1920
ggcggccagg aacgtgctgg tgaccgagga caacgtgatg aagatcgctg acttcgggct   1980
ggcccgcgac atccaccaca tcgattacta caagaagacg acaaacggcc gcttgccggt   2040
gaagtggatg gccccggagg ctctgttcga ccgaatatac acccatcaga gtgatgtttg   2100
gtcgttcggt gtgctgctgt gggagatctt cacgttgggt ggttcgccct accccggcgt   2160
gcccgtggag gagctcttca agctgctgaa ggaaggccac aggatggaca agcccagcaa   2220
ctgcaccaac gagctgtaca tgatgatgcg cgactgctgg cacgccgtgc cctcccagcg   2280
ccccaccttc aagcagctgg tggaggacct ggacaggatc gtggccatga cctccaatca   2340
ggagtacctg gacctgtcgg tgccgttgga tcagtactcg cccggcttcc cggccacgcg   2400
cagctccacc tgctcctcgg gggaggactc ggtgttctcc cacgacccgc tgcccgacga   2460
gccctgcctg ccgcgctgcc ccccgcacag ccacggagcg ctgaagcggc actgaggctc   2520
cgcacgcagc tgtgcccccc cgggcaccac caccgcaggg aactgcccaa agctttcggc   2580
tgctgttggg ctgttggtcg gctctttttt tttatcaccc atttaaaccc ttcccacgag   2640
gtctgtgctt ggacatcccc acgtggcggt gccgccgtgt ccctatgggg ccgatgcgcg   2700
ctgtgagcat cgcatcccag cgctgcccca acccacacgt gtggggtgtg cagcacacgg   2760
ggccgccccg gggatcagcg ctaggacaga agtcccgtgt acatagctaa aatatgtata   2820
aatatgaata tatatttaca tgtcttttta aaagggtggt taccagagct gtgccaggct   2880
gggtagggag gtgctggtgg ctggtagata tcagttgcta tatat                   2925
```

<210> SEQ ID NO 54
<211> LENGTH: 823

```
<212> TYPE: PRT
<213> ORGANISM: Gallus gallus

<400> SEQUENCE: 54

Met Val Ser Trp Asp Ser Gly Cys Leu Ile Cys Leu Val Val Val Thr
1               5                   10                  15

Met Ala Gly Leu Ser Leu Ala Arg Pro Ser Phe Asn Leu Val Val Glu
            20                  25                  30

Asp Ala Thr Leu Glu Pro Glu Glu Pro Pro Thr Lys Tyr Gln Ile Ser
        35                  40                  45

Gln Pro Asp Val His Ser Ala Leu Pro Gly Glu Pro Leu Glu Leu Arg
    50                  55                  60

Cys Gln Leu Lys Asp Ala Val Met Ile Ser Trp Thr Lys Asp Gly Val
65                  70                  75                  80

Pro Leu Gly Pro Asp Asn Arg Thr Val Ile Ile Gly Glu Tyr Leu Gln
                85                  90                  95

Ile Lys Asp Ala Ser Pro Arg Asp Ser Gly Leu Tyr Ala Cys Thr Ala
            100                 105                 110

Ile Arg Thr Leu Asp Ser Asp Thr Leu Tyr Phe Ile Val Asn Val Thr
        115                 120                 125

Asp Ala Leu Ser Ser Gly Asp Asp Glu Asp Asp Asn Asp Gly Ser Glu
    130                 135                 140

Asp Phe Val Asn Asp Ser Asn Gln Met Arg Ala Pro Tyr Trp Thr His
145                 150                 155                 160

Thr Asp Lys Met Glu Lys Arg Leu His Ala Val Pro Ala Ala Asn Thr
                165                 170                 175

Val Lys Phe Arg Cys Pro Ala Met Gly Asn Pro Thr Pro Thr Met Arg
            180                 185                 190

Trp Leu Lys Asn Gly Lys Glu Phe Lys Gln Glu His Arg Ile Gly Gly
        195                 200                 205

Tyr Lys Val Arg Asn Gln His Trp Ser Leu Ile Met Glu Ser Val Val
    210                 215                 220

Pro Ser Asp Lys Gly Asn Tyr Thr Cys Ile Val Glu Asn Gln Tyr Gly
225                 230                 235                 240

Ser Ile Asn His Thr Tyr His Leu Asp Val Val Glu Arg Ser Pro His
                245                 250                 255

Arg Pro Ile Leu Gln Ala Gly Leu Pro Ala Asn Ala Ser Ala Val Val
            260                 265                 270

Gly Gly Asp Val Glu Phe Val Cys Lys Val Tyr Ser Asp Ala Gln Pro
        275                 280                 285

His Ile Gln Trp Ile Lys His Val Glu Arg Asn Gly Ser Lys Tyr Gly
    290                 295                 300

Pro Asp Gly Leu Pro Tyr Leu Gln Val Leu Lys Ala Ala Gly Val Asn
305                 310                 315                 320

Thr Thr Asp Lys Glu Ile Glu Val Leu Tyr Ile Arg Asn Val Thr Phe
                325                 330                 335

Glu Asp Ala Gly Glu Tyr Thr Cys Leu Ala Gly Asn Ser Ile Gly Ile
            340                 345                 350

Ser Phe His Thr Ala Trp Leu Thr Val Leu Pro Ala Pro Glu Lys Glu
        355                 360                 365

Lys Glu Phe Pro Thr Ser Pro Asp Tyr Leu Glu Ile Ala Ile Tyr Cys
    370                 375                 380

Ile Gly Val Phe Leu Ile Ala Cys Met Val Leu Thr Val Ile Leu Cys
385                 390                 395                 400
```

```
Arg Met Lys Asn Thr Thr Lys Lys Pro Asp Phe Ser Ser Gln Pro Ala
                405                 410                 415

Val His Lys Leu Thr Lys Arg Ile Pro Leu Arg Arg Gln Val Thr Val
            420                 425                 430

Ser Ala Asp Ser Ser Ser Ser Met Asn Ser Asn Thr Pro Leu Val Arg
        435                 440                 445

Ile Thr Thr Arg Leu Ser Ser Thr Ala Asp Ala Pro Met Leu Ala Gly
    450                 455                 460

Val Ser Glu Tyr Glu Leu Pro Glu Asp Pro Lys Trp Glu Phe Pro Arg
465                 470                 475                 480

Asp Lys Leu Thr Leu Gly Lys Pro Leu Gly Glu Gly Cys Phe Gly Gln
                485                 490                 495

Val Val Met Ala Glu Ala Val Gly Ile Asp Lys Asp Arg Pro Lys Glu
            500                 505                 510

Ala Val Thr Val Ala Val Lys Met Leu Lys Asp Asp Ala Thr Glu Lys
        515                 520                 525

Asp Leu Ser Asp Leu Val Ser Glu Met Glu Met Met Lys Met Ile Gly
    530                 535                 540

Lys His Lys Asn Ile Ile Asn Leu Leu Gly Ala Cys Thr Gln Asp Gly
545                 550                 555                 560

Pro Leu Tyr Val Ile Val Glu Tyr Ala Ser Lys Gly Asn Leu Arg Glu
                565                 570                 575

Tyr Leu Arg Ala Arg Arg Pro Pro Gly Met Glu Tyr Ser Phe Asp Ile
            580                 585                 590

Asn Arg Val Pro Glu Glu Gln Met Thr Phe Lys Asp Leu Val Ser Cys
        595                 600                 605

Thr Tyr Gln Leu Ala Arg Gly Met Glu Tyr Leu Ala Ser Gln Lys Cys
    610                 615                 620

Ile His Arg Asp Leu Ala Ala Arg Asn Val Leu Val Thr Glu Asn Asn
625                 630                 635                 640

Val Met Lys Ile Ala Asp Phe Gly Leu Ala Arg Asp Ile Asn Asn Ile
                645                 650                 655

Asp Tyr Tyr Lys Lys Thr Thr Asn Gly Arg Leu Pro Val Lys Trp Met
            660                 665                 670

Ala Pro Glu Ala Leu Phe Asp Arg Val Tyr Thr His Gln Ser Asp Val
        675                 680                 685

Trp Ser Phe Gly Val Leu Met Trp Glu Ile Phe Thr Leu Gly Gly Ser
    690                 695                 700

Pro Tyr Pro Gly Ile Pro Val Glu Glu Leu Phe Lys Leu Leu Lys Glu
705                 710                 715                 720

Gly His Arg Met Asp Lys Pro Ala Asn Cys Thr Asn Glu Leu Tyr Met
                725                 730                 735

Met Met Arg Asp Cys Trp Gln Ala Val Pro Ser Gln Arg Pro Thr Phe
            740                 745                 750

Lys Gln Leu Val Glu Asp Leu Asp Arg Ile Leu Thr Leu Thr Thr Asn
        755                 760                 765

Glu Glu Tyr Leu Asp Leu Ser Gly Pro Leu Glu Gln Tyr Ser Pro Ser
    770                 775                 780

Tyr Pro Asp Thr Arg Ser Ser Cys Ser Ser Gly Asp Asp Ser Val Phe
785                 790                 795                 800

Ser Pro Asp Pro Met Pro Tyr Glu Pro Cys Leu Pro Lys Tyr Gln His
                805                 810                 815

Met Asn Gly Ser Val Lys Thr
            820
```

<210> SEQ ID NO 55
<211> LENGTH: 2716
<212> TYPE: DNA
<213> ORGANISM: Gallus gallus

<400> SEQUENCE: 55

```
cgcgcggaac cctccggctg cagccgctgc cgttcccggt gaggagggat tgccctggcc     60
gaaggcactg cgttctgtcc atgctcctgt agaggtgctc agatgggatt aaagtccaca    120
tggagatatg gaaatggacc aggaacttac tctaaaaaga tggtcagctg ggattcgggt    180
tgccttatct gcctggtggt ggtcaccatg gctggacttt ccctggctcg accgtcattt    240
aacttagttg ttgaagatgc cactttggaa cccgaagagc cgccaaccaa ataccaaatc    300
tctcagccag atgtacactc tgcacttcca ggagaaccac ttgagttgcg ctgtcaattg    360
aaagacgccg tcatgatcag ttggactaag gatggggtcc ccttggggcc cgacaatagg    420
acagtgatta ttggggagta cttacaaatt aaagatgctt cacccagaga ttcgggcctc    480
tatgcttgca ctgctattag gaccctagac agtgatactc tgtacttcat tgtaaatgtt    540
acagatgctc tttcttctgg ggatgatgaa gatgacaatg atgggtctga ggactttgtg    600
aatgacagca accagatgag ggcgccctat tggacacaca cagacaaaat ggagaaaagg    660
ttacacgcag tgccagcagc aaacactgtc aagtttcgtt gcccagccat gggaaaccca    720
acaccaacca tgagatggct gaaaaatggg aaagagttta aacaagaaca tcgtattggc    780
ggctataagg tccgcaacca gcactggagt ctcatcatgg agagcgtagt cccatccgac    840
aaaggaaatt acacgtgcat cgtggaaaac cagtatggct ccatcaacca cacttaccat    900
ctcgatgttg tcgagcgatc accgcacagg cccatcctcc aggctggcct tccagcaaac    960
gcctcggctg tagtcggagg tgatgtcgag tttgtctgca aagtctacag tgatgctcaa   1020
ccccacattc agtggataaa acacgtagag aggaatggca gtaaatacgg accagatgga   1080
ctgccttacc ttcaggtttt aaaggctgcc ggtgttaaca ctacggacaa agaaattgag   1140
gttctctata tacggaatgt aacttttgag gatgctgggg agtatacatg cttggcgggt   1200
aattctattg ggatatcctt tcacactgca tggttgacag ttctgccagc tcctgaaaag   1260
gaaaaggaat ttcccacatc tccagactac ctggaaatag caatttactg catagggggtc  1320
ttcctgatcg cctgcatggt gctgacagtc atcctgtgcc gcatgaagaa caccaccaag   1380
aagcctgact tcagcagcca gcccgctgtc cacaagctga caaagcgaat ccctctgcgc   1440
agacaggtaa cagtgtcagc tgactcaagc tcctccatga actccaacac gcctctggtg   1500
aggataacta cacgcctctc ctccactgct gatgccccaa tgctggcagg ggtctcggaa   1560
tatgaactgc cagaggatcc aaaatgggag tttccaaggg ataagctgac gctgggtaaa   1620
cccctggggg aaggctgctt tgggcaagtg gtgatggctg aagcggtggg gattgacaaa   1680
gaccggccca aagaagcagt gactgtggca gtgaagatgc tgaaagatga tgctacggaa   1740
aaggatctat ccgacctggt gtcagagatg gagatgatga agatgattgg gaaacataaa   1800
aatatcatca atcttcttgg agcctgtacc caggatggtc cgctgtatgt gattgtagaa   1860
tatgcttcca aaggaaacct gcgtgagtac ctgcgagcac gccgccctcc tgggatggaa   1920
tactcctttg atattaacag ggtcccagag gagcagatga cattcaagga cttggtatcc   1980
tgcacgtacc agttggcaag aggcatggag tacttggctt cacaaaaatg tatccaccga   2040
gacctagctg caagaaatgt tttggtaact gaaaataacg tcatgaaaat agcagacttc   2100
ggtttagcca gagacatcaa caatatagat tattataaaa agactactaa tggacggctt   2160
```

```
ccagtaaagt ggatggctcc agaagctctg tttgacagag tttacacaca ccaaagcgac   2220

gtatggtcat ttggtgtgct aatgtgggag atcttcacct taggaggatc gccctaccca   2280

ggaatcccag tggaggaact ttttaagctg cttaaagaag ggcaccgaat ggataaacct   2340

gccaactgca ccaatgaact ctacatgatg atgagagatt gctggcaggc tgtgccttca   2400

caaagaccaa cttttaaaca gttggtagaa gacttggatc ggatccttac tctcacaact   2460

aacgaggagt atctggacct cagcggacct ctggagcagt attcacctag ctaccctgac   2520

accaggagtt cgtgttcttc aggtgatgac tctgtttttt ctcctgatcc aatgccttat   2580

gaaccctgtc ttcccaagta ccaacacatg aatgggagcg ttaaaacatg aaaagaagca   2640

agaacatcaa gctacctacc acatacagaa catcttttct ccgggaccct aaagattctg   2700

cttgtacata tgaaat                                                    2716
```

<210> SEQ ID NO 56
<211> LENGTH: 827
<212> TYPE: PRT
<213> ORGANISM: Gallus gallus

<400> SEQUENCE: 56

```
Met Ser Glu Ala Gly Gly Gly Ala Ala Ala Ala Ala Ser Leu Pro Arg
1               5                   10                  15

Ser Arg Ala Gly Gly Met Arg Ala Ala Trp Gly Ser Val Trp Cys Leu
            20                  25                  30

Cys Leu Ala Ala Ala Val Gly Ala Leu Pro Ala Ala Arg Arg Arg Gly
        35                  40                  45

Ala Glu Arg Ser Gly Gly Gln Ala Ala Glu Tyr Leu Arg Ser Glu Thr
    50                  55                  60

Ala Phe Leu Glu Glu Leu Val Phe Gly Ser Gly Asp Thr Ile Glu Leu
65                  70                  75                  80

Ser Cys Asn Thr Gln Ser Ser Ser Val Ser Val Phe Trp Phe Lys Asp
                85                  90                  95

Gly Ile Gly Ile Ala Pro Ser Asn Arg Thr His Ile Gly Gln Lys Leu
            100                 105                 110

Leu Lys Ile Ile Asn Val Ser Tyr Asp Asp Ser Gly Leu Tyr Ser Cys
        115                 120                 125

Lys Pro Arg His Ser Asn Glu Val Leu Gly Asn Phe Thr Val Arg Val
    130                 135                 140

Thr Asp Ser Pro Ser Ser Gly Asp Asp Glu Asp Asp Asp Asp Glu Ser
145                 150                 155                 160

Glu Asp Thr Gly Val Pro Phe Trp Thr Arg Pro Asp Lys Met Glu Lys
                165                 170                 175

Lys Leu Leu Ala Val Pro Ala Ala Asn Thr Val Arg Phe Arg Cys Pro
            180                 185                 190

Ala Gly Gly Asn Pro Thr Pro Thr Ile Tyr Trp Leu Lys Asn Gly Lys
        195                 200                 205

Glu Phe Lys Gly Glu His Arg Ile Gly Gly Ile Lys Leu Arg His Gln
    210                 215                 220

Gln Trp Ser Leu Val Met Glu Ser Val Val Pro Ser Asp Arg Gly Asn
225                 230                 235                 240

Tyr Thr Cys Val Val Glu Asn Lys Tyr Gly Asn Ile Arg His Thr Tyr
                245                 250                 255

Gln Leu Asp Val Leu Glu Arg Ser Pro His Arg Pro Ile Leu Gln Ala
            260                 265                 270
```

```
Gly Leu Pro Ala Asn Gln Thr Val Val Val Gly Ser Asn Val Glu Phe
        275                 280                 285

His Cys Lys Val Tyr Ser Asp Ala Gln Pro His Ile Gln Trp Leu Lys
    290                 295                 300

His Val Glu Val Asn Gly Ser Lys Tyr Gly Pro Asp Gly Thr Pro Tyr
305                 310                 315                 320

Val Thr Val Leu Lys Thr Ala Gly Val Asn Thr Thr Asp Lys Glu Leu
                325                 330                 335

Glu Ile Leu Tyr Leu Arg Asn Val Thr Phe Glu Asp Ala Gly Glu Tyr
            340                 345                 350

Thr Cys Leu Ala Gly Asn Ser Ile Gly Phe Ser His His Ser Ala Trp
        355                 360                 365

Leu Thr Val Leu Pro Ala Glu Glu Leu Met Glu Met Asp Asp Ser Gly
    370                 375                 380

Ser Val Tyr Ala Gly Ile Leu Ser Tyr Gly Thr Gly Leu Val Leu Phe
385                 390                 395                 400

Ile Leu Val Leu Val Ile Val Ile Ile Cys Arg Met Lys Met Pro Asn
                405                 410                 415

Lys Lys Ala Met Asn Thr Thr Thr Val Gln Lys Val Ser Lys Phe Pro
            420                 425                 430

Leu Lys Arg Gln Gln Val Ser Leu Glu Ser Asn Ser Ser Met Asn Ser
        435                 440                 445

Asn Thr Pro Leu Val Arg Ile Thr Arg Leu Ser Ser Ser Asp Gly Pro
    450                 455                 460

Met Leu Ala Asn Val Ser Glu Leu Glu Leu Pro Pro Asp Pro Lys Trp
465                 470                 475                 480

Glu Leu Ala Arg Ser Arg Leu Thr Leu Gly Lys Pro Leu Gly Glu Gly
                485                 490                 495

Cys Phe Gly Gln Val Val Met Ala Glu Ala Ile Gly Ile Asp Lys Asp
            500                 505                 510

Lys Pro Asn Lys Ala Ile Thr Val Ala Val Lys Met Leu Lys Asp Asp
        515                 520                 525

Ala Thr Asp Lys Asp Leu Ser Asp Leu Val Ser Glu Met Glu Met Met
    530                 535                 540

Lys Met Ile Gly Lys His Lys Asn Ile Ile Asn Leu Leu Gly Ala Cys
545                 550                 555                 560

Thr Gln Asp Gly Pro Leu Tyr Val Leu Val Glu Tyr Ala Ser Lys Gly
                565                 570                 575

Asn Leu Arg Glu Tyr Leu Arg Ala Arg Arg Pro Pro Gly Met Asp Tyr
            580                 585                 590

Ser Phe Asp Thr Cys Lys Leu Pro Glu Glu Gln Leu Thr Phe Lys Asp
        595                 600                 605

Leu Val Ser Cys Ala Tyr Gln Val Ala Arg Gly Met Glu Tyr Leu Ala
    610                 615                 620

Ser Gln Lys Cys Ile His Arg Asp Leu Ala Ala Arg Asn Val Leu Val
625                 630                 635                 640

Thr Glu Asp Asn Val Met Lys Ile Ala Asp Phe Gly Leu Ala Arg Asp
                645                 650                 655

Val His Asn Ile Asp Tyr Tyr Lys Lys Thr Thr Asn Gly Arg Leu Pro
            660                 665                 670

Val Lys Trp Met Ala Pro Glu Ala Leu Phe Asp Arg Val Tyr Thr His
        675                 680                 685

Gln Ser Asp Val Trp Ser Phe Gly Val Leu Leu Trp Glu Ile Phe Thr
    690                 695                 700
```

```
Leu Gly Gly Ser Pro Tyr Pro Gly Ile Pro Val Glu Glu Leu Phe Lys
705                 710                 715                 720

Leu Leu Lys Glu Gly His Arg Met Asp Lys Pro Ala Asn Cys Thr His
                725                 730                 735

Asp Leu Tyr Met Ile Met Arg Glu Cys Trp His Ala Val Pro Ser Gln
            740                 745                 750

Arg Pro Thr Phe Lys Gln Leu Val Glu Asp Leu Asp Arg Val Leu Thr
        755                 760                 765

Met Thr Ser Thr Asp Glu Tyr Leu Asp Leu Ser Val Pro Phe Glu Gln
    770                 775                 780

Tyr Ser Pro Ala Gly Gln Asp Thr His Ser Thr Cys Ser Ser Gly Asp
785                 790                 795                 800

Asp Ser Val Phe Ala His Asp Leu Leu Pro Asp Glu Pro Cys Leu Pro
                805                 810                 815

Lys His Val Pro Cys Asn Gly Val Ile Arg Thr
            820                 825
```

<210> SEQ ID NO 57
<211> LENGTH: 5395
<212> TYPE: DNA
<213> ORGANISM: Gallus gallus

<400> SEQUENCE: 57

```
cgcagcagcg gagcggagcg ctgagcggcg gcagcatgcg gccgggggat gtctgaggcg     60

ggcggcggtg cggcggcggc ggcctcgctg ccccggagcc gcgccggagg gatgcgggcg    120

gcctggggct ccgtctggtg cctgtgcctg gcggcggccg tcggagcgct gccggcggcg    180

cgccggcgcg gagcggagcg gagcggcggg caggcggcag aatacttgag gagcgagacc    240

gcctttctgg aagagttggt gtttggaagt ggagatacca ttgaactttc ctgtaacacc    300

cagagctctt ctgtgtcagt tttctggttt aaagatggta ttgggattgc accttccaac    360

agaactcata ttggacaaaa actgttgaag ataatcaatg tgtcatatga cgattcgggg    420

ctgtacagtt gcaagccaag gcattccaac gaggtcctgg gaaactttac agtcagagtg    480

acagattccc cttcgtcagg tgatgatgaa gatgatgacg atgagtcaga ggatacaggt    540

gtccccttct ggacccggcc agataagatg gagaagaagc tgctggcagt tcctgccgcc    600

aacaccgttc gcttccgatg tccagcaggt ggaaacccaa ctcccaccat ttactggctg    660

aagaatggca aagaattcaa gggagagcac aggatcgggg gcatcaagtt gcgacaccag    720

cagtggagct tggtgatgga gagcgttgtg ccgtcagatc gaggaaacta cacctgtgtt    780

gtggagaaca aatatggcaa tattaggcac acataccagc ttgatgtttt agaacggtca    840

ccccaccgac caatcctgca agcaggactc cctgccaatc agactgtggt ggtcgggagc    900

aatgtggaat ttcactgcaa ggtctacagc gatgcccagc ctcatatcca gtggctgaaa    960

cacgtagaag tcaacggcag caagtatgga cctgatggga caccctatgt cacagtgctg   1020

aagacggcag gtgttaacac aacggataag gagctagaga ttctgtactt gcgaaatgtt   1080

acttttgagg atgctgggga atatacttgt ctcgcaggga attctattgg gttctcacat   1140

cactctgctt ggctgacggt gctaccagca gaggagctga tggaaatgga tgattcgggc   1200

tcagtgtacg ctggcattct cagctatggc actggcttag tcctcttcat cctggtgctg   1260

gtcattgtga ttatctgcag gatgaaaatg ccaaacaaaa aggccatgaa caccaccact   1320

gtacagaaag tctccaaatt tccactcaag agacagcagg tgtcgttgga gtccaactct   1380

tccatgaatt ccaacacacc cctggtccgg atcactcgtc tctcctccag cgatggcccg   1440
```

```
atgctggcca acgtctctga gctggaactt cctccagatc ccaagtggga attggcacgt   1500
tctcgcctga ccctggggaa gccgcttggt gagggctgtt ttggccaagt ggtgatggcg   1560
gaagcaattg ggattgataa agacaagcca aacaaggcca tcaccgtggc tgtcaagatg   1620
ttaaaagatg atgccacaga caaggacctt tcagacctgg tctctgagat ggaaatgatg   1680
aaaatgattg ggaagcacaa aaacatcatt aacctgctcg gtgcttgcac gcaggacgga   1740
ccgctctacg tgttggttga atatgcatcg aaggggaact tgcgggaata cctcagggca   1800
cgtcgcccac ctggcatgga ctattccttc gacacctgca agctgcccga ggagcagttg   1860
acatttaaag acctggtttc ctgcgcctac caggtggccc ggggcatgga gtacttggcg   1920
tcacagaaat gcattcatcg tgacttggca gccaggaatg tgttagtcac tgaggacaat   1980
gtgatgaaaa tagctgattt tggccttgct agagacgttc acaacatcga ctattacaag   2040
aaaaccacca atggtcggct gcctgtgaaa tggatggctc cagaagcatt gtttgaccgg   2100
gtctatactc accagagcga tgtctggtct tttggagtgc tactatggga gatcttcact   2160
ttgggagggt ctccgtaccc gggaattcct gttgaagaac tcttcaaact cttgaaagaa   2220
ggccatcgga tggataaacc cgccaactgt acccacgacc tgtacatgat catgcgggag   2280
tgctggcacg ctgtcccctc gcagcgaccc acattcaagc agctggtgga agacctggac   2340
agagtcctca ccatgacatc cactgatgag tacctggacc tctcggtgcc ctttgagcaa   2400
tactcacccg ctggccagga cacccacagc acctgctcct caggggacga ctcggttttt   2460
gcacatgacc tgctgcctga tgagccctgc ctgcccaagc acgtgccctg taatggcgtc   2520
atccgcacgt gacggccccc caggacagac ggatggacag acaggcagtg ttcccaccct   2580
ggcgcaagcg cagagcgccg aagacaaacc catagtgaag gatgtttcca tgaaactgct   2640
cggtgatgcc ggaggatttt tgttgtcaag tttttttttg ttttgtttgg ttggtttttt   2700
tcccatttgc tgtataaaaa gtcaagaagc actgtttggc ctgaaggaac tcatctcttg   2760
ccaagatgat ctatcgtgta tgattttttt tattattatt attattatta tttttctttt   2820
ttcctaagca gaatgttaaa cctgagggta ctgccctccc gcctgcgctt gccgagcgcc   2880
tgagtagcca atctgtgcct actatatgaa aaagaggaaa aaaatcttcc tagaagaaga   2940
aaagctaatg aaaaaaaaaa tgtaaagaat gtagaaattc tttgcttatg caatctgtac   3000
atgaaccttt ttggtggagc tgaaaagcca cgttgcctgc agggattcat atatttatag   3060
aaatatctat atttttgttg tcgtcgtttt tatagcttcg tgaccttatt tcccagctac   3120
atagaaggaa tcttgtccag aagaagaaga aaaataaata aatgatacgc aaatcaacat   3180
ggaggaagaa ttaaaaataa ttaaaataaa aaaaaaagac agtcaagtca tcctatagga   3240
ggagagcacc gcctggccgc tggccatgtc ctgtagggat tgcacaccca tgtggcatct   3300
tgagctgtgt cccagcctgc aggaagagcc aatgtgggga aaatcttgct ttttggagac   3360
gggggtttgc atacttttgc ttacaaaggg caagttgtag ggagaagct cctccagccc   3420
ttggcaccag cggtttggct ccatctacat gcagtgactt ggagaaagaa gttacgggta   3480
cctgtaggca agagccttta acttatatca aaaaggttta ttccagagaa tctgtgtata   3540
tatctataaa tatatcctgt atatatataa ataaatatat ggggaaaaaa aaaaagaatg   3600
tataatacta attcaacgta aagcagtact gagagagagt ctcaaaatac gagcattgca   3660
atctaggata tactgatctg gatgaaagag aagagttgtg tttgttttat atcttcacag   3720
ttttgtttta aaaattgtac gttaacatgt atatttgtaa agttatttat agacattaac   3780
agatctgttc ttcggtttaa atagcgtagc gttactgtaa actttaaatt tcaccgagtt   3840
```

```
taagggtggt ttttttttta acttattaaa aatggagaaa aagtatatta atcaagtttt   3900
tcttttgtgt ttatgggaaa tattgaaaga atgtatagat gtacagtcct ttaacaaatt   3960
acatttaatg ttttatatat atatatatat atatatgtat tcgttaaaaa aaatattagt   4020
ttatcctgga ttgcagtgag caaaggtaag tttatttttc aatacatcac cagtggttaa   4080
aaccaaacca atagcagaga gatggttttt acgtatttca gaaaaaaaga gggccaagat   4140
ttcttccatc actttaacca ctgtgcatta cgggggcgtg ggtgtttatt tttctatttt   4200
ggaatgaagg tattctttgt ggtcgagtca ataagaagca cgcagcaaag caacgtgttg   4260
actttggatg acgcgcatta atttttttttc cccctgtgcc agtaatgttg tattttgggt   4320
ttaagaaata ccatacgggc aaaatagaga gaggagcgac attgtttgca ggggagatgc   4380
aacgactgca tatttctttt gcatttaaca cattgaaaaa tgccagtgat gcctagtttt   4440
ctgtgttcga aatgctgtgc ttttttttgtt cctgaatgtc agacagcaca tgagtgaaaa   4500
aagaaccttc acgtggctca ggctgacgag gggggggagg tttggggtgg gcttttttttg   4560
ttgttgtttg ttcctttttt tttccttttt tttttttttt tttttttttg tccagaagac   4620
tgtatctact accacaaaga ggcaaggaga attgcatcct gaattcctcc tttatgtttt   4680
gctctggtgc atattacata tcaaggtttc agaatagcag gatggcagca tctcattttt   4740
aaggtggttt gttgtttttt ttttggtttt tttttttcct tcttagagcc acaaaatcct   4800
taccctaaaa taaataattt atagtttgag gttatttcaa tggaagtttg agaaggtaga   4860
tttctataga attttgtttt gttgggatta aaaaaaaaag aaaaaaaaga atttttttggt   4920
attttcttac aaatgtctgc taattgtgta cattccaagt actcgaagcg ttgcgtttcg   4980
tgtactgaaa aaagaaaatg tacaaaactg tgcatgattt caaatgttac tagatattat   5040
aaatatatat ataatttatt gagtttttac aagatgtatc tgttgtagac ttgttgactt   5100
aacatttctt attcaatgct tatatagttt tatagcctgg actgttatct ttaagagctt   5160
aaaaaaatta aaattccaat tttgttacat tttatactgt tgatgttaca atccacaggt   5220
ttgcgtagcg tgatttttca acgagcaact ctgttcagtt tattttaata atgtacttct   5280
gtgcctgaca gctgcagctg tccaaggtgt gagacaaaca ctaaataaaa ctattctgct   5340
tttgttaaaa aaaaaaaaaa aaaaaaaaaa aaaaaaaaaa aaaaaaaaaa aaaaa        5395
```

FGF MODULATION OF IN VIVO ANTIBODY PRODUCTION AND HUMORAL IMMUNITY

CROSS-REFERENCE TO RELATED APPLICATIONS

This application claims the benefit of U.S. provisional patent application Ser. No. 61/324,947 filed Apr. 16, 2010, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Feb. 10, 2011, is named AB001000.txt and is 275,385 bytes in size.

FIELD OF THE INVENTION

The invention relates to the field of humoral immunity.

BACKGROUND OF INVENTION

Organisms control antibody production at multiple steps during an immune response and this response must be carefully adjusted to the invading pathogen. If the response is excessive, autoimmune defects can damage host tissues, whereas if it is inadequate, the pathogen may persist and threaten survival. Soluble factors have been identified that stimulate the humoral immune response, but our knowledge of negative regulators of this process has been quite limited (Ravetch et al., 2000, Science 290:84). Indeed, few soluble cytokines have been identified whose loss of function leads to enhanced antibody production.

During the humoral immune response, a complex set of signaling events orchestrate antibody production. The process begins with antigen presentation to mature peripheral B cells, which proliferate and migrate to germinal centers. Cells possessing B cell receptors with the highest affinity for antigen are favored to survive while their low-affinity counterparts more readily undergo apoptosis. The activated B cells which survive this selection differentiate into memory B cells or antibody-secreting plasma cells. Many B cells also secrete antibody outside of the germinal center selection process in the extrafollicular response (MacLennan et al., 2003, Immunol Rev 194:8). Extrafollicular responses are thought to be important following exposure to T-independent antigens (Fagarasan et al., 2000, Science 290:89; Martin et al., 2001. Immunity 14:617). Once the antigen has been removed, B cells return to a resting state. Turning off B cell activation is necessary both for homeostatic resetting of antibody secretion and also for preventing pathologic autoimmune conditions. Little is known about the soluble factors which control the deactivation process.

The fibroblast growth factor (FGF) family of extracellular regulators has been shown to control the physiology and development of virtually all higher vertebrate tissues. Twenty-three FGF ligands have been identified in mammals, and these ligands interact with cell surface receptors encoded by five different genes (Wiedemann et al., 2000, Genomics 69:275; Ornitz et al., 2001, Genome Biol 2). Alternative splicing in the ligand-binding domain generates variable forms of the FGF receptors, thereby increasing diversity.

FGF2, or basic FGF, was the first identified FGF family member (Abraham et al., 1986, Embo J 5:2523) and is one of the most extensively studied. Expressed in most embryonic and adult tissues, it exists in high and low molecular weight isoforms due to initiation of translation at alternative start sites. It binds to all five receptors with preference for the "c" alternate splice form of receptors 1-3 (Ornitz et al, 1996, J Biol Chem 271:15292). FGF2 has been shown to stimulate widely varying effects, including proliferation, differentiation, apoptosis, and migration. Consequently, the FGF2 signal is interpreted differently depending on cellular context.

U.S. Pat. No. 4,994,559 discloses human basic fibroblast growth factor.

U.S. Pat. No. 5,229,501 discloses expression and use of human fibroblast growth factor receptor.

U.S. Pat. No. 5,288,855 discloses an extracellular form of human fibroblast growth factor receptor.

U.S. Pat. No. 5,707,632 discloses receptors for fibroblast growth factors.

U.S. Pat. No. 5,891,655 discloses methods for identifying molecules that regulate FGF activity and oligosacharide modulators of FGF receptor activation.

U.S. Pat. No. 6,071,885 discloses treatment of FGF-mediated conditions by administration of cardiac glycoside and aglycone derivatives thereof.

U.S. Pat. No. 6,350,593 discloses receptors for fibroblast growth factors and methods for evaluating compositions for antagonism to fibroblast growth factors and fibroblast growth factors receptors.

U.S. Pat. No. 6,255,454 discloses expression and use of a human fibroblast growth receptor and a soluble version of the receptor.

U.S. Pat. No. 6,900,053 discloses antisense modulation of fibroblast growth factor receptor 2 expression.

Multiple human therapeutics are designed to enhance the immune response, but their use in humans are complicated by severe side effects. For example, exogenous IL-2 is administered to patients with advanced melanoma in order to stimulate the anti-tumor immune response. But this biologic, acting as a systemic cytokine which directly activates T cells, is beset by harsh side effects, such as dangerous hypotension. What is needed are new methods for enhancing immune function and, in particular, humoral immunity.

SUMMARY OF INVENTION

A new role for fibroblast growth factor (FGF) signaling in the negative regulation of the humoral immune response has been discovered by the present inventor. It has been found that antibody production to a Type I Independent antigen is enhanced in the absence of FGF2 and conversely, is suppressed when FGF2 is over-expressed. Therefore, FGF2 is an inhibitor of the humoral immune response. In addition, it has been discovered that splenic germinal centers require FGF2 for efficient formation.

One embodiment of the invention provides a method for increasing humoral immune response to vaccination with an immunogen, for example, an antigen or a live or killed vaccine, in a mammal or other higher vertebrate, that includes: in conjunction with the vaccination of a mammal to the immunogen other than FGF2, inhibiting the activity of a fibroblast growth factor, such as FGF2, in the mammal, thereby increasing the humoral immune response to the antigen. In one variation, the immunogen is other than a fibroblast growth factor and other than a fibroblast growth factor receptor.

Another embodiment of the invention provides a method for treating an immune deficiency in a mammal, such as a human, that includes: increasing the production of endogenous antibodies in the mammal by inhibiting the activity of a fibroblast growth factor, such as FGF2, in the mammal.

A further embodiment of the invention provides a method for treating a microbial infection in a mammal, such as a human, that includes inhibiting the activity of a fibroblast growth factor, such as FGF2 in a mammal in need of treatment for a microbial infection, to an extent effective to increase antibody production in the mammal. The inhibiting step may include or consist of administering a fibroblast growth factor antagonist, such as a FGF2 antagonist, to the mammal in an amount effective to increase antibody production in the mammal. The method may further include the step of administering an antibiotic or anti-viral agent to the mammal which is active against the microbial infection.

Another embodiment of the invention provides a method for increasing in vivo antibody production in a mammal, such as a human, that does not have a cancer that includes the step of by inhibiting the activity of a fibroblast growth factor, such as FGF2, in the mammal. In one variation, the mammal is a geriatric human.

A still further embodiment of the invention provides a method for decreasing antibody production, such as pathological antibody production, in a mammal such as a human, in need of such reduction, by administering to the mammal, in an amount effective to decrease antibody production in the mammal, a fibroblast growth factor or agonist thereof, such as FGF2 or an FGF2 agonist, or an agonist of a receptor that binds a fibroblast growth factor such as FGF2, for example FGFR1, FGFR2 and FGFR3.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention.

DETAILED DESCRIPTION

It is now shown that the humoral immune response is altered in FGF2 mutant mice. FGF2 deficient mice produce more antibody to a Type I independent antigen while FGF2 over-expressing mice show suppressed antibody production to the same pathogenic stimulus. In addition, germinal center formation is compromised in the absence of FGF2. Surprisingly, changes in both antibody production and germinal center formation are observed in mice lacking a single copy of FGF2, demonstrating that lymphocytes are particularly sensitive to FGF2 gene dosage. These studies provide the first evidence that FGF signaling is a crucial regulator of the humoral immune response and mature B cell function.

Materials and Methods

Mice.

Figure 3:
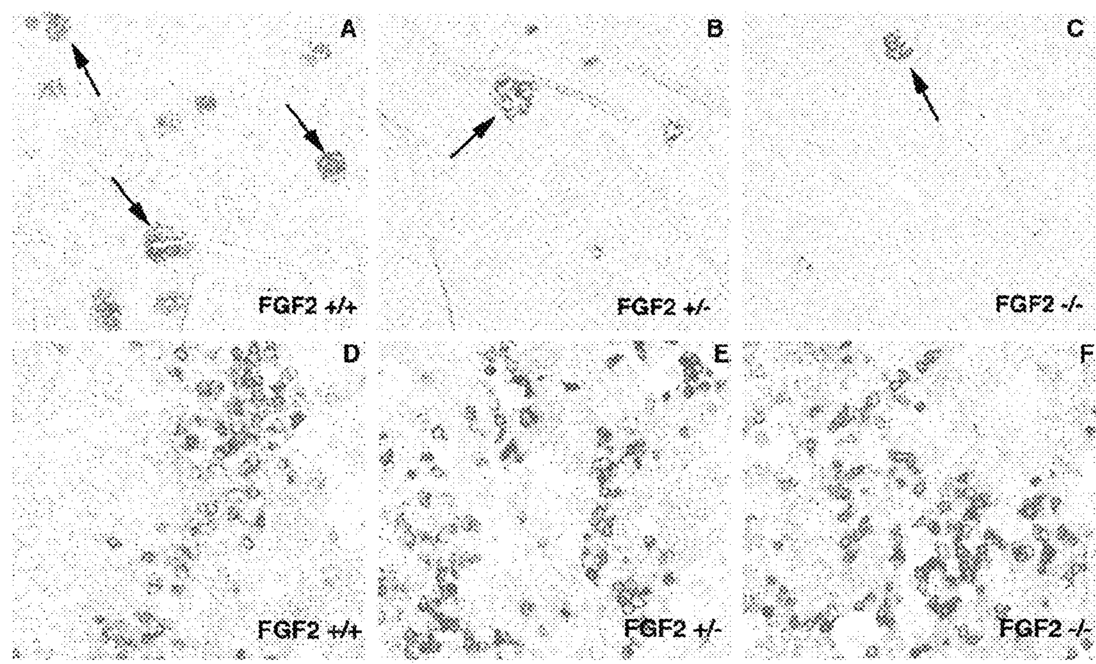
FIG. 3, panels A-F, show that FGF2 deficiency affects germinal centers but not syndecan expression.

FGF2−/− (homozygous gene knockout) mice were obtained from two academic sources. These mice display relatively benign defects in wound healing, blood pressure regulation and cortical neurogenesis and do not express detectable levels of FGF2 protein (Ortega et al., 1998. Proc Natl Acad Sci USA 95:5672; Zhou et al., 1998, Nature Medicine 4:20). Both sets of knockouts showed increases in antibody production and data in FIGS. 1 and 3 are for animals obtained from the University of Cincinnati. Heterozygous animals (mixture of 129SvEv:Black Swiss) were mated and heterozygous and null animals were compared to littermate controls. Adult mice of both sexes were used. FGF2 transgenic animals exhibit bone dysplasia and disruption of endothelial homeostasis (Fulgham et al., 1999, Endothelium 6:185; Coffin et al., 1995, Mol Biol Cell 6:1861). Animals (FVBN) heterozygous for the transgene were mated to wild type and adult animals of both sexes were compared to littermate controls. Animals were maintained in a pathogen-free facility, following institutional standards. Protocols adhered to IACUC guidelines.

Humoral Immune Response.

Mice were immunized intraperitoneally with 50 ug TNP-LPS (tri-nitrophenol lipopolysaccharide) emulsified with complete Freund's adjuvant in PBS (200 ul final volume). Serum was harvested from retro-orbital eye bleeds. After coagulation, bleeds were centrifuged and sodium azide (0.01%) was added. ELISAs for TNP specific antisera were performed on plates coated with TNP-BSA (Biosearch) and primary antisera were bound overnite at 4° C. Goat anti-mouse IgG (all Ig isotypes) coupled to Alkaline Phosphatase was used as secondary antisera (Jackson). The genotype of the serum was unknown to the experimenter. Absorbance (405 nM) was measured in triplicate on a Molecular Devices spectrophotometer. Values were averaged and measurements were taken from absorbance in the middle of the dynamic range. For quantification of difference in antibody titer, serial dilutions were performed and the average value from the serum of all animals (minimum n=5, +/−s.e.m.) was plotted. Omission of either primary or secondary anitsera reduced signal to background levels.

Immunohistochemistry

Histochemistry was performed on 5 micrometer histologic sections made from formalin fixed, paraffin-embedded spleens. Sections were blocked in PBST (PBS with 0.1% Tween-20) containing 10% normal rabbit serum, stained with the lectin peanut agglutinin, then biotinylated anti-peanut agglutinin (Vector Laboratories, Burlingame, Calif.), or rat anti-CD138 (syndecan-1) (Becton Dickinson) followed by biotinylated goat anti-rat IgG secondary antibody (Jackson Immunoresearch). Primary antibody was incubated either overnight at 4° C. or for one hour at room temperature. Removal of either primary or secondary antiserum abolished specific signal.

Germinal center number was scored by experimenters blind to the source of the sections. At least three serial sections were scored for each spleen. Results are based on three independent experiments from two or more animals per genotype. Data are presented from the final experiment which used the largest number of animals.

Proliferation of B Cells In Vitro.

Adult wild type mice (C57B16) were sacrificed and spleens were rapidly removed. After dissociation into single cell suspension and red blood cell lysis with NH4Cl, splenocytes were isolated by centrifugation over a Ficoll gradient. Subsequently, B lymphocytes were purified by one of two methods, complement mediated lysis or CD43 negative selection. For complement lysis, cells were incubated with anti-Thy 1 antibody (J1J), anti-L3T4 (GK 1.5), anti-Ly2 (TIB105, ATCC) and rabbit complement (Sigma) for two hours at 37°. CD43 negative selection was carried out using anti-CD43 (Serotec) and Miltenyi microbeads according to the manufacturer's instructions. Cells were cultured in RPMI 1640, 10% fetal calf serum for three days in the presence of anti-CD40 (mAb 1C10, generous gift of Hsiou-Chi Liou, Weill Medical College of Cornell University) and anti-IgM Fab'2 fragments (Jackson Immunoresearch). FGF1 (100 ng/ml) and Heparin (10 ug/ml) were added, and the number of cells was determined in triplicate compared to Heparin alone using a Coulter Counter (Coulter) or trypan blue exclusion with the same results.

Results

FGF2 Regulates the Humoral Immune Response

In the course of studies to evaluate the role of FGF signaling in multiple myeloma, we decided to investigate whether B cell function might be altered in FGF mutant mice. If FGF signaling affects mature B cell activity, one would predict that the humoral immune response would be affected by loss of function mutations in one of the FGF family members. To address this issue, we examined the humoral immune response in FGF2 deficient mice, one of the most widely expressed FGFs.

Figure 1A:
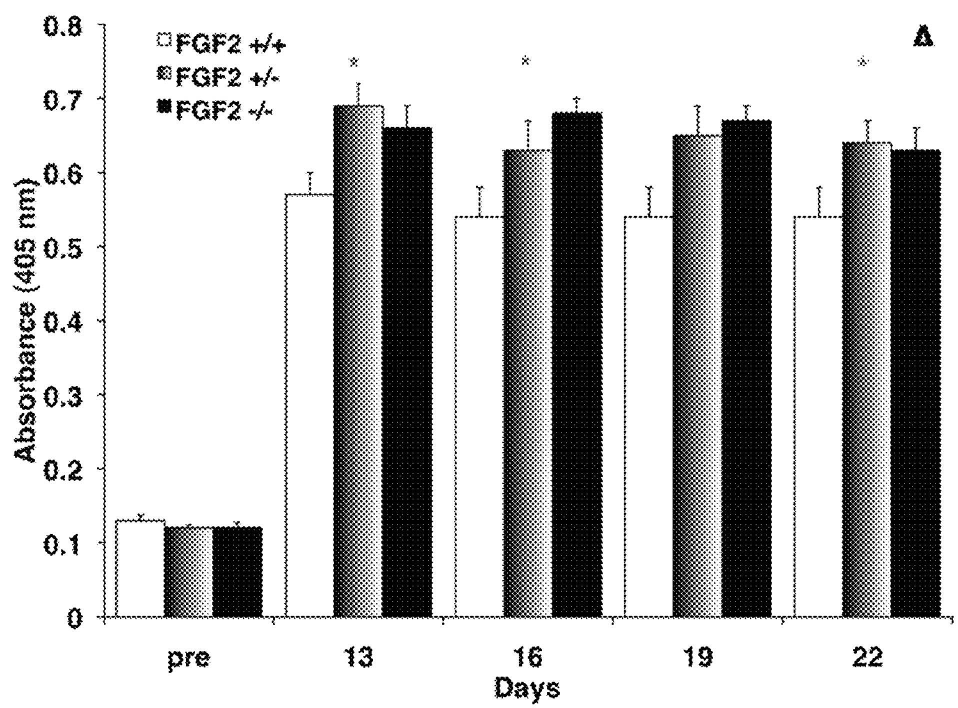
FIG. 1A shows that FGF2 deficient mice respond more strongly to a Type I Thymus Independent Antigen.
Figure 1B:
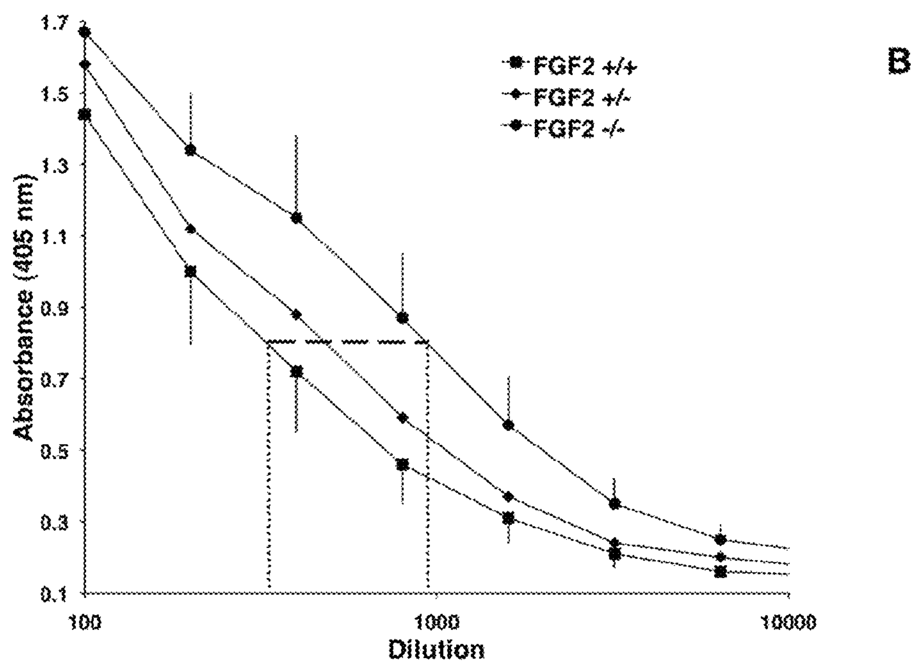
FIG. 1B shows the difference in antibody titer of FGF2 deficient animals compared to littermate controls following immunization.

Immunization with a type I independent antigen, TNP-LPS, typically stimulates polyclonal B cell activation and proliferation. This antigen can elicit antibody production in T cell depleted animals, suggesting that the response can be largely independent of T cell help. The humoral response to TNP-LPS was enhanced in the absence of FGF2 (FIG. 1A). The magnitude of the peak response and the decay to baseline are potentiated by FGF2 deficiency. Three weeks after immunization, anti-TNP antibody titers are approximately three-fold higher than littermate controls (FIG. 1B). The size of this potentiation is greater than that seen with the inhibitory FC receptor, FCγRIIB, a gene intrinsic to B cells (Takai et al., 1996, Nature 379:346). Surprisingly, mice lacking a single copy of FGF2 produce more anti-TNP antibody (FIG. 1A, day 13 and day 22 time point). These results demonstrate that FGF2 negatively regulates the primary humoral immune response and is required for the normal inactivation of antibody secretion.

FIG. 1. FGF2 deficient mice respond more strongly to a Type I Thymus Independent Antigen. Mice were immunized with 50 ug TNP-LPS and anti-TNP specific antibodies were measured by ELISA. In FIG. 1A, data points represent average absorbance from the serum of at least five animals. Asterisks indicate statistical differences at $p<0.05$ (student's t test). FIG. 1B shows the quantification of the difference in antibody titer of FGF2 deficient animals compared to littermate controls at day nineteen after immunization. Data points represent the mean absorbance+/−s.e.m. at the indicated dilutions for each genotype. Broken line between curves with corresponding vertical line delineates difference in antibody titer at the same absorbance.

To determine whether FGF2 is sufficient to regulate antibody production, we examined the humoral immune response in FGF2 transgenic mice. These animals express a human FGF2 gene driven by the ubiquitously active promoter, phosphoglycerate kinase (Coffin et al., 1995, Mol Biol Cell 6:1861). Different forms of FGF2 protein are produced from the FGF2 gene, including several high and low molecular weight isoforms. In FGF2 transgenic animals, there is a marked increase in the expression of the 18-Kd form of FGF2 in selected tissues, including spleen (Coffin et al., 1995, Mol Biol Cell 6:1861).

Figure 2A:
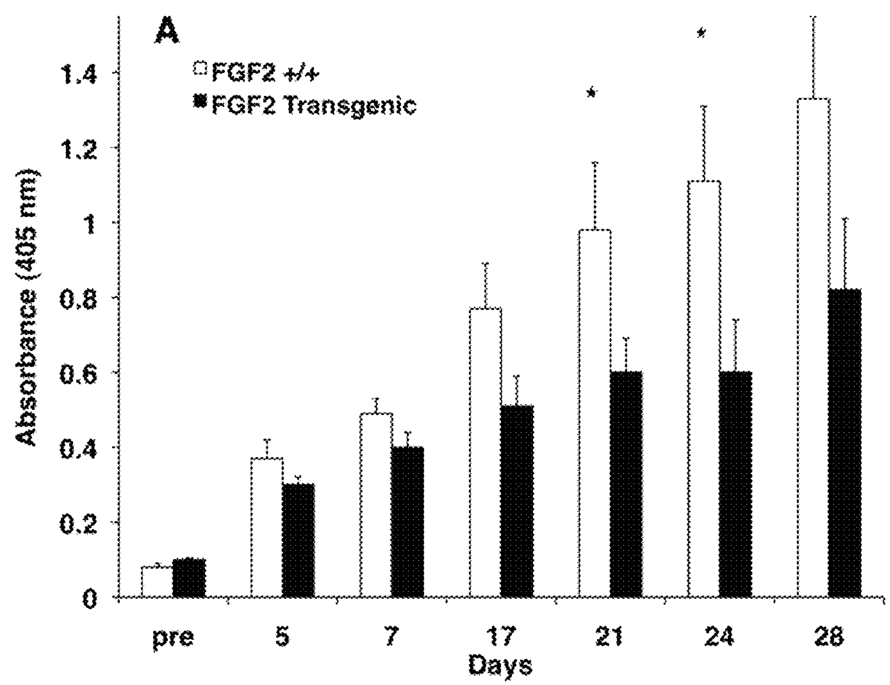
FIG. 2A shows FGF2 transgenic mice respond more weakly to a Type I Thymus Independent Antigen.
Figure 2B:
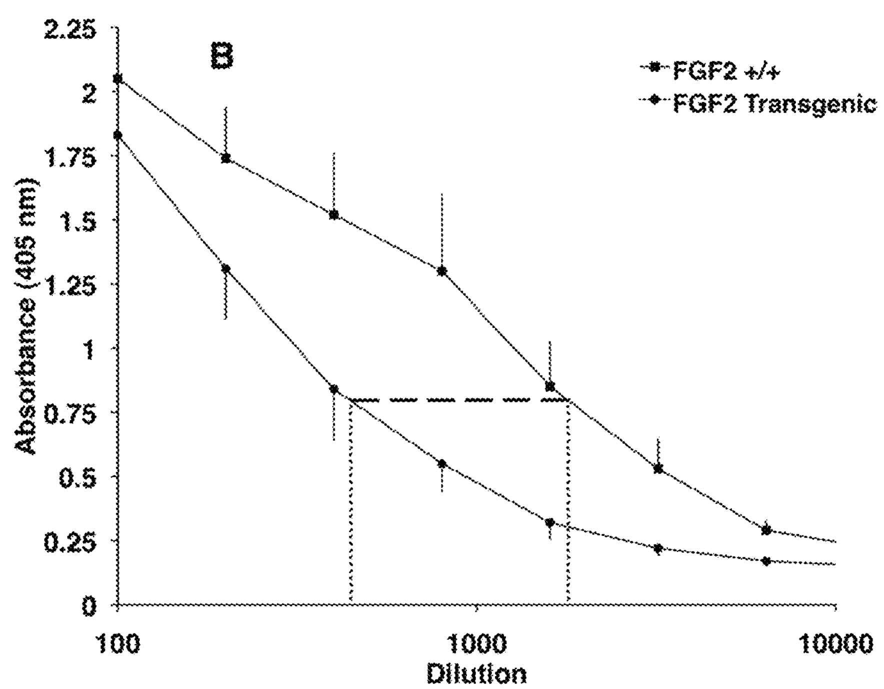
FIG. 2B shows the quantification of antibody titer of FGF2 transgenic animals compared to littermate controls following immunization.

FIG. 2. FGF2 transgenic mice respond more weakly to a Type I Thymus Independent Antigen. Mice were immunized with 50 ug TNP-LPS and anti-TNP specific antibodies were measured by ELISA using TNP-BSA coated plates. Asterisks indicate statistical differences at $p<0.05$ (student's t test). FIG. 2B shows the quantification of antibody titer of FGF2 transgenic animals compared to littermate controls at day twenty one after immunization. Data points represent the mean absorbance+/−s.e.m. at the indicated dilutions. Broken line between curves with corresponding vertical line delineates difference in antibody titer at the same absorbance.

It was found that antibody production in response to TNP-LPS is significantly diminished in FGF2 transgenic animals, as shown in FIG. 2A. Suppression of antibody production begins relatively late during the primary response, with statistically significant differences not observable until twenty one days after administration of immunogen. The reduction in antibody titers is slightly larger than the enhancement seen in the absence of FGF2 (four-fold). Therefore, FGF2 is both necessary and sufficient to control the humoral immune response. Taken together, these observations identify FGF2 as a soluble regulator of antibody production.

Once activated by antigen, B cells migrate to germinal centers, where high affinity, somatically mutated antibodies are generated. To determine whether germinal centers are affected by FGF2, we examined the number of splenic germinal centers formed in the FGF2 null mice. Lectin staining reveals that the number of germinal centers is substantially reduced approximately two weeks after immunization with TNP-LPS, with six-fold fewer germinal centers formed in null animals (FIG. 3, panels a-c; Table 2). Fewer germinal centers are also observed two days after immunization (Table 1). Unexpectedly, germinal centers are also reduced in heterozygous animals.

TABLE 1

| Mouse | +/+ | +/− | −/− |
|---|---|---|---|
| 1 | 4 | 2 | 1 |
| 2 | 3 | 0 | 0 |
| 3 | 0 | 0 | 0 |
| 4 | 8 | 0 | 0 |
| 5 | 3 | 2 | — |
| 6 | 1 | 2 | — |
| 7 | 0 | 1 | — |
| 8 | 0 | 4 | — |
| 9 | 1 | 0 | — |
| 10 | 4 | 0 | — |
| 11 | 4 | 3 | — |
| 12 | 3 | 3 | — |
| 13 | — | 4 | — |
| Mean | 2.6 | 1.6 | 0.25 |
| s.e.m. | 0.7 | 0.4 | 0.25 |
| N | 12 | 13 | 4 |

TABLE 2

| Mouse | +/+ | +/− | −/− |
|---|---|---|---|
| 1 | 5 | 3 | 11 |
| 2 | 13 | 0 | 3 |

TABLE 2-continued

| Mouse | +/+ | +/− | −/− |
|---|---|---|---|
| 3 | 11 | 0 | 3 |
| 4 | 9 | 0 | 0 |
| 5 | 14 | 0 | 0 |
| 6 | 8 | 0.5 | 0 |
| 7 | — | — | 4 |
| Mean | 10 | 0.6 | 1.7 |
| s.e.m. | 1.4 | 0.5 | 0.76 |
| N | 6 | 6 | 7 |

Tables 1 and 2. Germinal center formation is dependent on FGF2 gene dosage. FGF2+/+, +/−, −/− mice were immunized i.p. with 50 ug TNP-LPS. Spleens were stained for expression of germinal centers with peanut agglutinin two days (Table 1) and approximately two weeks (Table 2) after immunization. Significantly fewer germinal centers were formed in FGF2 heterozygous ($p<0.01$) and null mice ($p<0.01$) sixteen days after immunization (Student's t test). Significantly fewer germinal centers were formed in FGF2 null mice ($p<0.05$) two days after immunization.

Gross morphologic features of the spleen are similar in the three genotypes. To determine whether plasma cell development is affected in FGF2 deficient animals, we examined the expression of syndecan-1, a cell surface heparin sulfate proteoglycan which is expressed on plasma cells. The number of syndecan positive plasma cells is not noticeably different, suggesting that FGF2 does not influence the adoption of the plasma cell fate in the spleen (FIG. 3, panels d-f). These results demonstrate that splenic germinal center formation is dependent on FGF2 gene dosage.

FIG. 3. FGF2 deficiency affects germinal centers but not syndecan expression. FGF2+/+, +/−, −/− mice were immunized i.p. with 50 ug TNP-LPS. A-C) Spleens were stained for expression of germinal centers with peanut agglutinin two weeks after immunization. D-F) Expression of syndecan-1 was determined by monoclonal antibody anti-CD138 (BD).

TABLE 3

| Mouse | Transgenic | Wild-type |
|---|---|---|
| 1 | 3.5 | 6 |
| 2 | 2 | 6 |
| 3 | 0 | 2 |
| 4 | 0.5 | 0 |
| 5 | 2 | 2 |
| 6 | 3 | 4 |
| 7 | 0 | 1 |
| 8 | 2 | 2 |
| 9 | 4 | 8.5 |
| 10 | 2 | — |
| Mean | 1.9 | 3.5 |
| s.e.m | 0.4 | 0.9 |
| n | 10 | 9 |

Table 3. Germinal center formation is not affected by ectopic expression of FGF2. FGF2 transgenic mice and littermate controls were immunized i.p. with 50 ug TNP-LPS. Spleens were stained for expression of germinal centers with peanut agglutinin fourteen days after immunization.

To determine whether germinal centers were affected by over-expression of FGF2, we performed the same experiment in FGF2 transgenic animals. We find that although there is a trend towards fewer germinal centers when FGF2 is over-expressed, the difference is not statistically significant (Table 3). These data show that over-expression of FGF2 is not sufficient to regulate germinal center formation two weeks after immunization with a Type 1 independent antigen.

Figure 4:
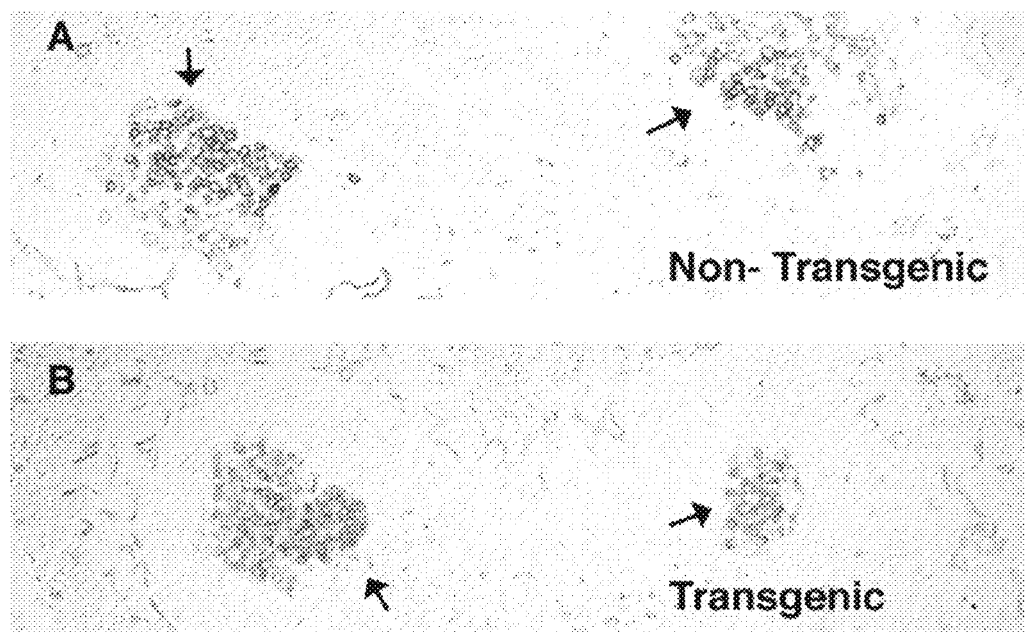
FIG. 4, panels A and B, show that ectopic expression of FGF2 does not suppress germinal center formation.

FIG. 4. Ectopic expression of FGF2 does not suppress germinal center formation. FGF2 transgenic and littermate controls were immunized i.p. with 50 ug TNP-LPS. A,B) Spleens were stained for expression of germinal centers with peanut agglutinin two weeks after immunization.

FGF2 is one of the more widely expressed members of the FGF family of ligands, with strong expression in multiple tissues. To determine whether FGF2 is expressed in the spleen we evaluated FGF2 levels by ELISA (R and D Systems). We find that FGF2 is found at 302+/−17 pg/ml (mean+/−s.d. n=4), demonstrating levels that are comparable to those found in other FGF2 responsive tissues. In addition, functional studies have demonstrated that both FGF-1 and FGF2 are present in the spleen in forms which can stimulate liver cell proliferation (Suzuki et al., 1992, Biochem Biophys Res Commun 186:1192).

To determine whether FGF can directly control B cell activation, we explored whether addition of exogenous FGF would affect B cell proliferation in vitro. B cells were purified from spleen and CD40 and BCR signaling were simultaneously activated using stimulating antibodies. Inducing these systems transmits powerful growth and survival signals, leading to rapid proliferation. To investigate whether FGF signaling might affect this response, we incubated the cells in the presence of FGF-1. We used FGF-1 instead of FGF2 because it stimulates the widest range of FGF receptors (8). Under these conditions, B cell number is inhibited by FGF stimulation (Table 3), suggesting that it can directly inhibit antigen stimulated B cells.

TABLE 4

| Experiment | % Decrease |
|---|---|
| 1 | 27 |
| 2 | 25 |
| 3 | 10 |
| 4 | 15 |
| 5 | 16 |
| 6 | 25 |
| X | 19.7 +/− 2.8 |

Table 4. FGF signaling inhibits splenic B cell proliferation. Spleens from adult wild-type mice were dissected and highly enriched populations of B cells were purified. Cells were cultured in serum-containing medium for 3 days in the presence of a CD40 activating monoclonal antibody (1C10) and anti-mouse IgM Fab'2 fragments (Jackson). The values represent the percent decrease in total cell number observed with addition of 100 ng/ml FGF1 (determined in triplicate) as compared to heparin (10 ug/ml) alone. x=mean+/−s.e.m. One sample t test, $p<0.01$.

Discussion

Using gain and loss-of-function mouse models, it was shown that FGF2 controls the humoral immune response. These observations constitute the first indication that any member of this large family of pleiotropic signaling factors affects the humoral immune response.

Based on its widespread expression and its robust effects on a diverse array of cell types, FGF2 is postulated to control multiple biological processes. However, studies with mice lacking this gene have challenged this belief, implicating other FGF family members or suggesting that FGF signaling is not essential (Ortega et al., 1998. Proc Natl Acad Sci USA 95:5672; Zhou et al., 1998, Nature Medicine 4:201; Dono et al., 1998, Embo J 17:4213). In light of these limited phenotypes, it was not expected that mice lacking a single copy of FGF2 would show abnormalities in immune function. Thus, in contrast to other systems, lymphoid tissue appears to be especially sensitive to FGF2 gene dosage. Since FGF family members are widely expressed, these results raise the possibility that further investigation will uncover additional evidence for FGF-dependent effects on lymphocyte function.

Given the ability of FGF ligands to bind more than one receptor family member, it is surprising that compensation for FGF2 deficiency by one of the twenty-two other FGFs was not observed. In this regard, FGF-1 constitutes a plausible candidate because it structurally resembles FGF2 and also is expressed in the spleen (Suzuki et al., 1992, Biochem Biophys Res Commun 186:1192). On the other hand, studies with FGF-1/2 double knock out mice suggest that the mild wound healing and neural phenotypes in FGF2 null mice are not a result of FGF-1 substituting for FGF2 (Miller et al., 2000, Mol Cell Biol 20:2260). The type I independent antigen lipopolysaccharide is a key pathogenic substance in the cell wall of gram negative bacteria. The repeating epitope in this molecule leads to massive engagement of receptors on the surface of B cells, including the BCR, TLR2 and TLR4 (Yang et al., 1998, Nature 395:284; Takeuchi et al., 1999, Immunity 11:443). B cell evolution has developed rapid and vigorous pre-existing defenses against such frequent threats and consequently, antibody secretion in response to this stimulus is robust. The greater response in the absence of FGF2 demonstrates that FGF2 negatively regulates the primary humoral immune response. The magnitude of the enhanced response is greater than the enhancement seen with FC receptor, FC□RIIB, whose deletion shows no effect on the response to LPS at three weeks post immunization (Takai et al., 1996, Nature 379:346). It is believed that this represents the first example of enhanced antibody production in response to LPS due to genetic deficiency.

Animals over-expressing FGF2 have a suppressed humoral immune response to LPS, demonstrating that the gain of function phenotype is the opposite of the loss of function phenotype. It is concluded that FGF2 is both necessary and sufficient to regulate antibody production.

While not being limited by theory, it is not presently clear which step in the humoral immune response is inhibited by FGF2 signaling. Although the possibility that differences in plasma cell generation take place in other lymphoid tissues cannot be excluded, inhibition occurs without a substantial difference in the number of syndecan positive cells in the spleen (FIG. 3, panels D-F). Hence, FGF2 may regulate a step subsequent to the expression of syndecan-1, such as plasmablast migration, full terminal differentiation, or metabolic function of antibody secreting cells in the bone marrow. Consistent with this latter idea, FGF2 is strongly expressed by multiple cell types in the bone marrow (Brunner et al., 1993, Blood 81:631; Chou et al., 2003, Leuk Res 27:499.).

FGF2 may control antibody production either by directly signaling to B cells or indirectly by affecting cells which regulate plasma cell activity. The direct model is consistent with our data showing decreased proliferation in response to FGF signaling of primary mature B lymphocytes (Table 3). While the reduction in cell number is modest, it should be borne in mind that few substances can overcome the strong growth and survival signals turned on by simultaneous CD40 and BCR engagement. In agreement with a direct mode of action, a previous study reported that FGF receptors exist on normal human peripheral blood B cells (Genot, et al., 1989, Cell Immunol 122:424). However, the possibility that other cell types could mediate the observed effects cannot presently be excluded.

A negative correlation between antibody production and germinal center number was found. At first glance, this observation appears contradictory since one might expect that a reduction in germinal centers would decrease antibody production. However, numerous examples have demonstrated that germinal center number can be uncoupled from the humoral response. TNF receptor null animals lack germinal centers but produce substantial antibody titers in response to vesicular stomatitis virus (Karrer et al., 2000, J Immunol 164:768). Similarly, TNF-α null animals display dramatic alterations in splenic morphology but their antibody production to LPS is unaffected (Pasparakis et al., 1996, J Exp Med 184:1397).

Thus, the work described herein demonstrates that FGF2 plays two distinct and complementary roles in the humoral immune response. FGF2 facilitates germinal center formation, thereby contributing to the generation of activated B cells which defend against pathogenic stimuli. On the other hand, FGF2 reduces plasma cell activity and in so doing provides a limit on antibody production. Since FGF2 exerts opposing forces at different times during the B cell response, its activities in the immune system are certainly complex. Such complexity is consistent with observations in other tissues, where FGF signaling can stimulate radically different effects depending on its temporal and spatial locus of action.

Embodiments Relating to Inhibition of FGF2 Activity in a Mammal

In multiple disease states, vaccination provides inadequate protection and low percentages of seroconversion are observed (Cohen D et al., Diagnosis and management of the antiphospholipid syndrome. BMJ. 2010 May 14; 340:c2541). Non-limiting examples of vaccines for which the invention may be employed to increase humoral immune response include, Malaria vaccine (M. Esen et al. Vaccine. 2009 Nov. 16; 27(49):6862-8. Safety and immunogenicity of GMZ2-a MSP3-GLURP fusion protein malaria vaccine candidate); HIV vaccine (Hoxie J A. Annu Rev Med. 2010; 61:135-52. Toward an antibody-based HIV-1 vaccine.); Influenza vaccine (Nguyen M L et al Infect Immun. 2009 November; 77(11):4714-23. The major neutralizing antibody responses to recombinant anthrax lethal and edema factors are directed to non-cross-reactive epitopes); Influenza Vaccine in geriatric patients (Frasca D, Diaz, A, Romero, M et al. Vaccine. 2010 October 22. Intrinsic defects in B cell response to seasonal influenza vaccination in elderly humans.); and Anthrax vaccine (Nguyen M L et al Infect Immun. 2009 November; 77(11):4714-23. The major neutralizing antibody responses to recombinant anthrax lethal and edema factors are directed to non-cross-reactive epitopes.).

The invention may, for example, be used to increase antibody production and/or humoral immunity in patients, such as human patients, suffering from immunodeficiencies including but not limited to: Common variable immunodeficiency (Rezaei N et al Clin Vaccine Immunol. 2008 April; 15(4):607-11 Serum bactericidal antibody responses to meningococcal polysaccharide vaccination as a basis for clinical classification of common variable immunodeficiency.); primary immunodeficiency disorder (PIDD), Ig deficiency, IgG deficiency; and HIV disease.

One embodiment of the invention provides a method for increasing the humoral immune response to vaccination with an immunogen, for example, an antigen or a live vaccine, in a mammal, that includes: in conjunction with the vaccination of a mammal to the immunogen other than FGF2, inhibiting the activity of FGF2 in the mammal, thereby increasing the humoral immune response to the antigen. In one variation the immunogen is other than a fibroblast growth factor and other than a fibroblast growth factor receptor. The mammal may be a human, such as a geriatric human. The mammal, which may be human, may have an immune deficiency, such as but not limited to Common variable immunodeficiency; primary immunodeficiency disorder (PIDD), an immunoglobulin deficiency such as IgG deficiency, and HIV disease.

Another embodiment of the invention provides a method for treating an immune deficiency in a mammal, such as a human, that includes: increasing the production of endogenous antibodies in the mammal by inhibiting the activity of FGF2 in the mammal. In one variation, the mammal does not have cancer. The immune deficiency may be, for example, but is not limited to: Common variable immunodeficiency; primary immunodeficiency disorder (PIDD), an immunoglobulin deficiency such as IgG deficiency, and HIV disease. Non-human mammals also suffer from immunodeficiencies and may be treated according to the invention. For example, the method may be used to treat immunodeficiency associated with feline immunodeficiency virus (FIV) in a cat, such as a domesticated cat.

A further embodiment of the invention provides a method for treating a microbial infection in a mammal, such as a human, that includes: administering an FGF2 antagonist to a mammal in need of treatment for a microbial infection, wherein the FGF2 antagonist is administered in an amount effective to increase antibody production in the mammal. The method may further include the step of: administering an antibiotic or anti-viral agent to the mammal which is active against the microbial infection. The antibiotic or anti-viral agent is administered such that the effect of the antibiotic or anti-viral agent and that of the FGF2 antagonist are temporally overlapping in the mammal. The microbial infection may, for example, be a bacterial infection, a viral infection or a eukaryotic parasite infection. The method may further include the step of determining that the mammal has a microbial infection prior to administering the FGF2 antagonist.

Another embodiment of the invention provides a method for increasing in vivo antibody production in a mammal, such as a human, that does not have a cancer, which includes the step of inhibiting the activity of FGF2 in the mammal. In one variation, the mammal is a geriatric human or non-human mammal, such as a geriatric domesticated dog or cat.

A related embodiment provides a method for enhancing the production of antisera or polyclonal antibodies generally against a desired immunogen in a non-human mammal that includes the steps of: inhibiting FGF2 activity in the non-human mammal according to any of methods and ways described herein and immunizing the non-human mammal with an immunogen that is not a fibroblast growth factor or a fibroblast growth factor receptor, whereby the production of antibodies against the immunogen in the mammal is enhanced, increased and/or accelerated versus a comparable immunization without the inhibition of FGF2 activity. The method may further include the step of retrieving the polyclonal sera from the non-human mammal and optionally the step of isolating. The immunizing step may, for example, include more than one temporally separated immunization with the immunogen and may, for example, be aided by inclusion of an immunization adjuvant. The methods for production of antisera and polyclonal antibodies are well known and long-established in the art. See, for example, U.S. Pat. No. 5,440,021.

The increase in antibody production in response to inhibition of FGF2 activity in a mammal is a general characteristic of the invention which is not limited to the type of FGF2 inhibitor that is administered to the mammal to inhibit the activity of FGF2. Preferred types of inhibitors of FGF2 activity include antibodies and binding fragments thereof, both monoclonal and polyclonal, which bind to FGF2 and block its interaction with FGF binding receptors and antibodies, both monoclonal and polyclonal, which bind to an FGF receptor such as FGFR1, FGFR2 and FGFR3 and block binding of the ligand (FGF2) to the receptor. For example, a single chain, monoclonal scFv antibody that neutralizes FGF2 may be used such as that described in Tao et al, Selection and characterization of a human neutralizing antibody to human fibroblast growth factor-2, Biochem Biophys Res Commun. 2010 Apr. 9; 394(3):767-73. Epub 2010 Mar. 17 or one obtained by the method described therein. Antibodies blocking FGFR1 such as those those described in Sun et al., Am J Physiol Endocrinol Metab 292:964-976, 2007, or obtained according to the method of this article may be used. Gorbenk et al, Hybridoma, Volume 28, Number 4, 2009 also describes the production of anti-FGFR1 antibodies and their production. Monoclonal antibodies against FGFR3 and their production are described in Qing et al., J. Clin. Invest. 119:1216-1229 (2009) and in Gorbenko et al, Hybridoma, Volume 28, Number 4, 2009, 295-300.

Antibodies contain one or more antigen binding sites that specifically binds with an antigen. Antibodies include, but are not limited to polyclonal, monoclonal, chimeric, and humanized antibodies. Immunologically active portions include monovalent and divalent fragments such as Fv, single chain Fv (scFv), single variable domain (sVD), Fab, Fab' and F(ab')2 fragments. Immunologically active portions can be incorporated into multivalent from such as diabodies, triabodies, and the like. Antibodies further include antigen binding fragments displayed on phage, and antibody conjugates.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Isolated antibodies may, for example, be used as inhibitors of FGF2 activity according to the invention. Examples of isolated antibodies include an anti-FGF2 antibody that has been affinity purified using FGF2, an anti-FGF2 antibody that has been made by a hybridoma or other cell line in vitro, a human anti-FGF2 antibody isolated from a library such as a phage library, and a human anti-FGF2 antibody derived from a transgenic mouse.

In general, naturally occurring antibody molecules are composed of two identical heavy chains and two light chains. Each light chain is usually covalently linked to a heavy chain by an interchain disulfide bond, and the two heavy chains are further linked to one another by multiple disulfide bonds at the hinge region. The individual chains fold into domains having similar sizes (about 110-125 amino acids) and structures, but different functions. The light chain comprises one variable domain ($V_L$) and one constant domain ($C_L$). The heavy chain comprises one variable domain ($V_H$) and, depending on the class or isotype of antibody, three or four constant domains ($C_H1$, $C_H2$, $C_H3$ and $C_H4$). In mice and humans, the isotypes are IgA, IgD, IgE, IgG, and IgM, with IgA and IgG further subdivided into subclasses or subtypes. The portion of an antibody consisting of $V_L$ and $V_H$ domains is designated "Fv" and constitutes the antigen-binding site. A single chain Fv (scFv) is an engineered protein containing a $V_L$ domain and a $V_H$ domain on one polypeptide chain, wherein the N terminus of one domain and the C terminus of the other domain are joined by a flexible linker. "Fab" refers to the portion of the antibody consisting of $V_L$-$C_L$ (i.e., a light chain) and $V_H$-$C_H1$ (also designated "Fd").

Antibodies include without limitation single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

The antibody variable domains show considerable amino acid sequence variablity from one antibody to the next, particularly at the location of the antigen binding site. Three regions, called "complementarity-determining regions" (CDRs) are found in each of $V_L$ and $V_H$. The CDRs of an antibody are often referred to as "hypervariable regions."

"Fc" is the designation for the portion of an antibody which comprises paired heavy chain constant domains. In an $IgG_1$ antibody, for example, the Fc comprises $C_H2$ and $C_H3$ domains. The Fc of an IgA or an IgM antibody further comprises a $C_H4$ domain. The Fc is associated with Fc receptor binding, activation of complement-mediated cytotoxicity and antibody-dependent cellular-cytotoxicity. For natural antibodies such as IgA and IgM, which are complexes of multiple IgG like proteins, complex formation requires Fc constant domains.

Finally, the "hinge" region separates the Fab and Fc portions of the antibody, providing for mobility of Fabs relative to each other and relative to Fc, as well as including multiple disulfide bonds for covalent linkage of the two heavy chains. Thus, antibodies of the invention include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind specifically with antigens.

Antibody fragments also include polypeptides with amino acid sequences substantially similar to the amino acid sequence of the variable or hypervariable regions of the antibodies of the invention. Substantially the same amino acid sequence is defined herein as a sequence with at least 70%, at least about 80%, at least about 90%, at least about 95% or at least about 99% homology or identity to a compared amino acid sequence, as determined by the FASTA search method in accordance with Pearson and Lipman, Proc. Natl. Acad. Sci. USA 85:2444-2448 (1988).

Antibodies that may be employed as inhibitors according to the invention also include "chimeric" antibodies and binding fragments thereof. Such antibodies generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

Antibodies that may be employed as inhibitors according to the invention also include "humanized" antibodies. Humanized variable domains are constructed in which amino acid sequences which comprise one or more complementarity determining regions (CDRs) of non-human origin are grafted to human framework regions (FRs). For examples, see: Jones, P. T. et al., 1996, Nature 321, 522-25; Riechman, L. et al., 1988, Nature 332, 323-27; and U.S. Pat. No. 5,530,101 to Queen et al. A humanized construct is particularly valuable for elimination of adverse immunogenic characteristics, for example, where an antigen binding domain from a non-human source is desired to be used for treatment in a human. Variable domains have a high degree of structural homology, allowing easy identification of amino acid residues within variable domains which corresponding to CDRs and FRs. See, e.g., Kabat, E. A., et al., 1991, Sequences of Proteins of Immunological Interest. 5th ed. National Center for Biotechnology Information, National Institutes of Health, Bethesda, Md. Thus, amino acids which are likely to participate directly in antigen binding are easily identified. In addition, methods have been developed to preserve or to enhance affinity for antigen of humanized binding domains comprising grafted CDRs. One way is to include in the recipient variable domain the foreign framework residues which influence the conformation of the CDR regions. A second way is to graft the foreign CDRs onto human variable domains with the closest homology to the foreign variable region. Queen, C. et al., 1989, Proc. Natl. Acad. Sci. USA 86, 10029-33. CDRs are most easily grafted onto different FRs by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

Antibodies with variable domains that have been made less immunogenic by replacing surface-exposed residues so as to make the antibody appear as self to the immune system may also be employed as inhibitors (Padlan, E. A., 1991, Mol. Immunol. 28, 489-98). Antibodies have been modified by this process with no loss of affinity (Roguska et al., 1994, Proc. Natl. Acad. Sci. USA 91, 969-973). Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

It is often preferable to employ variable domains that are essentially human as when the recipient of the antibody is human. Human antibodies comprise human $V_H$ and $V_L$ framework regions (FWs) as well as human complementary determining regions (CDRs). Preferably, the entire $V_H$ and $V_L$ variable domains are human or derived from human sequences. The antibodies can be obtained directly from human cells, for example by creating human hybridomas.

Alternatively, human antibodies can be obtained from transgenic animals into which unrearranged human Ig gene segments have been introduced and in which the endogenous mouse Ig genes have been inactivated (reviewed in Brüggemann and Taussig, 1997, Curr. Opin. Biotechnol. 8, 455-58). Preferred transgenic animals contain very large contiguous Ig gene fragments that are over 1 Mb in size (Mendez et al., 1997, Nature Genet. 15, 146-56) but human Mabs of moderate affinity can be raised from transgenic animals containing smaller gene loci (See, e.g., Wagner et al., 1994, Eur. J. Immunol. 42, 2672-81; Green et al., 1994, Nature Genet. 7, 13-21).

Human antibodies can also be obtained from libraries of antibody $V_H$ and/or $V_L$ domains. For example, a variable domain library can be obtained from human genomic sequences, or from peripheral blood lymphocyte expressing productively rearranged variable region genes. Furthermore, the human gene library can be synthetic. In one embodiment, variable domain libraries can be created which comprise human framework regions with one or more CDRs that are synthesized to include random or partial random sequences. For example, a human $V_H$ variable domain library can be created in which members are encoded by a human $V_H$ gene segment and a synthetic sequence for the CDR3H region (i.e., a synthetic $D_H$-$J_H$ gene segment). Likewise, a human $V_L$ variable domain may be encoded by a human $V_L$ gene segment and a synthetic sequence for the CDR3L region (i.e., a synthetic $J_L$ gene segment). In another embodiment, the human frameworks may be synthetic in that they have a consensus sequence derived from known human antibody sequences or subgroups of human sequences. In another alternative, one or more CDRs is obtained by amplification from human lymphocytes expressing rearranged variable domains and then recombined into a particular human framework.

In order to screen libraries of variable domains, it is common to employ phage display libraries wherein combinations of human heavy and light chain variable domains are displayed on the surface of filamentous phage (see, e.g., McCafferty et al., 1990, Nature 348, 552-54; Aujame et al., 1997, Human Antibodies 8, 155-68). Combinations of variable domains are typically displayed on filamentous phage in the form of Fabs or scFvs. The library is screened for phage bearing combinations of variable domains having desired antigen binding characteristics. Preferred single domain and variable domain combinations display high affinity for a selected antigen and little cross-reactivity to other related antigens. By screening very large repertoires of antibody fragments, (see e.g., Griffiths et al., 1994, EMBO J. 13, 3245-60) a good diversity of high affinity binding domains are isolated, with many expected to have sub-nanomolar affinities for the desired antigen.

In a physiological immune response, mutation and selection of expressed antibody genes leads to the production of antibodies having high affinity for their target antigen. The $V_H$ and $V_L$ domains incorporated into antibodies of the invention can similarly be subject to in vitro or in vivo mutation and screening procedures in order to modify affinity and/or specificity. Thus, binding domains of the invention include those for which binding characteristics have been improved by mutating CDRs and/or FW regions by direct mutation, methods of affinity maturation, or chain shuffling. It is understood that amino acid residues that are primary determinants of binding of single domain antibodies can be within Kabat defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of *E. coli* (see, e.g., Low et al., J. Mol. Biol., 250: 359-368 (1996)). These methods of mutagenesis are illustrative of the many methods known to one of skill in the art.

Inhibitors that may be used according to the invention also include antigen binding proteins engineered from non-immunoglobulin scaffolds. For example, affibodies, which are derived from an immunoglobulin-binding domain of *S. aureus* protein A, possess no disulfide bonds and display reversible folding. Another example is fibronectin, which has an antibody-like structure and displays CDR-like loops. In contrast to antibodies, the fibronectin domain structure does not rely on disulfide bonds, yet displays high thermodynamic stability. Binding sites can be engineered into such scaffolds by, for example, diversifying codons at specified positions and screening for binding to a desired antigen. Codons can be randomized in loops, flat surfaces, cavities, or combinations of such locations. Further, peptide sequences can be inserted, usually in loops. Target-binding variants of resulting libraries can be isolated using selection of screening techniques that are well known in the art, not limited to phage display, ribosome display, bacteria or yeast surface display, and the like. For antigen-binding proteins intended for therapy, various strategies are available for minimizing potential immunogenicity. Human scaffolds can be employed, and immunogenicity can be minimized, for example, by PEGylation or T-cell epitope engineering (i.e., minimizing T-cell reactive sequences).

Antigen-binding proteins from non-immunoglobulin scaffolds often can be produced more economically than immunoglobulin-type proteins. For example, the absence of disulfide bonds or free cysteines allows for expression of functional molecules in the reducing environment of the bacterial cytoplasm, which usually gives higher yields than periplasmic expression, and is more convenient than refolding in vitro. Binz, H. K. et al. (Nat. Biotech. 23:1257-68, 2005) discloses a variety of such antigen-specific binding proteins and techniques for their development.

The identification or selection of antibodies or other molecules that inhibit binding of FGF2 or other FGFs to their receptors may be performed according to routine ligand-receptor binding assays, comparing binding in presence and absence of test agent, since the full sequences of FGF2 and its receptors are known in various mammals such as human. See, for example, U.S. Pat. No. 5,440,021 for ligand-receptor binding assays.

Another preferred type of inhibitor of FGF2 activity is a soluble FGF2-binding receptor or soluble portion of an FGF-binding receptor, such as a soluble form of FGFR1, FGFR2 and FGFR3. The soluble receptor sequence may, for example match the species in which it will be administered, i.e., a human receptor sequence may be used for a human recipient and so on. For example, FP-1039 is a soluble fusion protein consisting of the extracellular domains of human FGFR1 linked to the Fc region of human Immunoglobulin G1 (IgG1), which may be used as an FGF2 inhibitor/antagonist according to the invention (Five Prime Therapeutics, Inc., San Francisco, Calif.; Keer et al, ASCO 2010, Abstract no. TPS260).

FGF2 activity may also be inhibited according to the invention by vaccinating the subject mammal against FGF2 itself or against FGFR1, FGFR2 and/or FGFR3. For example, a peptide vaccine targeting the heparin-binding portion of FGF2 can be used to generate a specific anti-FGF2 antibody response in a mammal according the method of Plum et. al., Generation of a specific immunological response to FGF2 does not affect wound healing or reproduction, Immunopharmacol Immunotoxicol. 2004 February; 26(1):29-41.

For embodiments in which a soluble polypeptide, such as an antibody or soluble receptor, is used to inhibit FGF2 activity, a composition for intravenous administration, for example, to a human, may include 0.1 to 20 mg, such as 0.1 to 10 mg, of the polypeptide, and this may be a daily dose. More generally, dosages from 0.1 mg to about 100 mg per subject per day for one or more days may be used. Methods for preparing administrable compositions are well known to those skilled in the art and are described in more detail in such publications as Remington's Pharmaceutical Science, 19th ed., Mack Publishing Company, Easton, Pa. (1995). Polypeptides for administration to a subject may, for example, be provided in lyophilized form and rehydrated with sterile water before administration. The solution of polypeptide may then be added to an infusion bag containing 0.9% sodium chloride, USP, and, for example administered at a dosage of from 0.5 to 15 mg/kg body weight. Alternatively, for example, the polypeptide can be administered as a bolus injection, for example, at a dosage of 0.5 to 30 mg/kg body weight.

Still other suitable types of FGF2 activity inhibitors include, for example, antisense oligonucleotides targeting FGF2 or one or more of FGFR1, FGFR2 and FGFR3. Still further suitable inhibitors are small molecule inhibitors, for example cardiac glycosides or aglycone derivatives as described in U.S. Pat. No. 6,071,885 and FGF activity modulating oligosaccharides as described in U.S. Pat. No. 5,891,655. TKI258 (also known as CHIR-258) described in Sarker et al., Clin Cancer Res, 2008; 14(7) 2075-81, is another suitable small molecule FGF receptor inhibitor. Brivanib, a FGFR1Kinase inhibitor described in Bhide et al, Mol Cancer Ther; 9(2) February 2010, 369-78, is still another suitable small molecule inhibitor.

Embodiments Relating to Increasing FGF2 Activity in a Mammal

The invention also provides embodiments in which antibody production in vivo is purposefully reduced in a mammal, such as a human, by increasing FGF2 activity in the mammal, for example, by administration of FGF2 to the mammal or administration of an agonist of FGF2 or an agonist of an FGF2 receptor, such as FGFR1, FGFR2 or FGFR3 to the mammal, in an amount effective to decrease antibody production in the mammal. Where FGF2 is administered to a mammal recipient, the peptide sequence may, for example at least substantially or identically match the species in which it will be administered, i.e., a human receptor sequence may be used for a human recipient and so on.

This aspect of the invention finds practical application is the suppression of antibody production in acutely toxic states. In many cases, response to invading pathogens can lead to pathological autoimmune effects, with lymphocyte activity spiraling out of control. In situations like this, administration of FGF2 attenuates the uncontrolled secretion of antibody.

Similarly, multiple human pathologies result from secretion of autoimmune antibodies. Administration of FGF2 and FGF ligands will serve to attenuate the production of these antibodies and thus ameliorate the autoimmune disease. For example, autoimmune antibodies are observed in both systemic lupus erythematosus (Cohen D et al., Diagnosis and management of the antiphospholipid syndrome. BMJ. 2010 May 14; 340:c2541) and diverse arthritic disease (Calero I, et al., B cell therapies for rheumatoid arthritis: beyond B cell depletion. Rheum Dis Clin North Am 2010 May; 36(2):325-43), including rheumatoid arthritis, psoriatic arthritis, ankylosing spondylitis and juvenile idiopathic arthritis. In addition, increasing FGF2 activity in a mammal may be used to decrease or maintain a decreased level of antibody production in organ transplant patients, such as human organ transplant patients in order to decrease negative immune responses to and increase tolerance to the transplanted organ in the patient.

Accordingly, one embodiment of the invention provides a method for decreasing antibody production, such as pathological antibody production, in a mammal such as a human in need thereof by administering to the mammal FGF2 or an FGF2 agonist or an agonist of a receptor that binds FGF2 such as FGFR1, FGFR2 and FGFR3 in an amount effect to decrease antibody production in the mammal. In one variation, the mammal may have and be in need of treatment for systemic lupus erythematosus and diverse arthritic disease, including rheumatoid arthritis, psoriatic arthritis, ankylosing spondylitis and juvenile idiopathic arthritis and the method decreases the production of autoimmune antibodies in these mammals thereby treating the condition. In another variation, the mammal is an organ transplant patient such as a human organ transplant patient and the method reduces antibody response against the transplanted organ.

The sequences of fibroblast growth factors and their receptors are well characterized in humans and non-human mammals. For example, the following sequences are known and form part of this disclosure: Human FGF2 (NCBI Reference Sequence NM_002006.4; SEQ ID NO:1 peptide, SEQ ID NO:2 nucleotide), Human FGFR1 (GenBank Accession No. M34185.1; SEQ ID NO:3 peptide, SEQ ID NO:4 nucleotide), Human FGFR2 (NCBI Reference Sequence NM_000141.4; SEQ ID NO:5 peptide, SEQ ID NO:6 nucleotide), Human FGFR3 (NCBI Reference Sequence NM_000142.4; SEQ ID NO:7 peptide, SEQ ID NO:8 nucleotide), Human FGFR4 (GenBank Accession No. AF202063.1; SEQ ID NO:9 peptide, SEQ ID NO:10 nucleotide), *Bos taurus* FGF2 (NCBI Reference Sequence NM_174056.3; SEQ ID NO:11 peptide, SEQ ID NO:12 nucleotide), *Bos taurus* FGFR1 (Genbank Accession No. NM_001110207.1; SEQ ID NO:13 peptide, SEQ ID NO:14 nucleotide), *Bos taurus* FGFR2 (NCBI Reference Sequence XM_002698546.1; SEQ ID NO:15 peptide, SEQ ID NO:16 nucleotide); *Bos taurus* FGFR3 (NCBI Reference Sequence NM_174318.3; SEQ ID NO:17 peptide, SEQ ID NO:18 nucleotide), *Bos taurus* FGFR4 (NCBI Reference Sequence XM_002689008.1; SEQ ID NO:19 peptide, SEQ ID NO:20 nucleotide), *Sus scrofa* FGF2 (NCBI Reference Sequence XM_003129213.1; SEQ ID NO:21 peptide, SEQ ID NO:22 nucleotide), *Sus scrofa* FGFR1 (NCBI Reference Sequence: XM_001928678.2; SEQ ID NO:23 peptide, SEQ ID NO:24 nucleotide), *Sus scrofa* FGFR2 (NCBI Reference Sequence NM_001099924.1; SEQ ID NO:25 peptide, SEQ ID NO:26 nucleotide), *Sus scrofa* FGFR3 (GenBank Accession No. BV726808.1; SEQ ID NO:27 cds nucleotide), *Sus scrofa* FGFR4 (NCBI Reference Sequence XM_003123682.1; SEQ ID NO:28 peptide, SEQ ID NO:29 nucleotide), *Macaca mulatta* FGF2 (NCBI Reference Sequence XM_001099284.2; SEQ ID NO:30 peptide, SEQ ID NO:31 nucleotide), *Macaca fascicularis* FGFR1 (GenBank Accession No. AB220417.1; SEQ ID NO:32 peptide, SEQ ID NO:33 nucleotide), *Macaca mulatta* FGFR2 partial (GenBank Accession No. AY083548.1; SEQ ID NO:34 peptide, SEQ ID NO:35 nucleotide), *Macaca mulatta* FGFR3 (NCBI Reference Sequence XM_002802167.1; SEQ ID NO:36 peptide, SEQ ID NO:37 nucleotide), *Macata mulatta* FGFR4 (NCBI Reference Sequence XM_001087243.2; SEQ ID NO:38 peptide, SEQ ID NO:39 nucleotide), *Mus musculus* FGF2 (NCBI Reference Sequence NM_008006.2; SEQ ID NO:40 peptide, SEQ ID NO:41 nucleotide), *Mus musculus* FGFR1 (NCBI Reference Sequence NM_010206.2; SEQ ID NO:42 peptide, SEQ ID NO:43 nucleotide), *Mus musculus* FGFR2 (NCBI Reference Sequence NM_010207.2; SEQ ID NO:44 peptide, SEQ ID NO:45 nucleotide), *Mus musculus* FGFR3 (NCBI Reference Sequence NM_008010.4; SEQ ID NO:46 peptide, SEQ ID NO:47 nucleotide), and *Mus musculus* FGFR4 (NCBI Reference Sequence NM_008011.2; SEQ ID NO:48 peptide, SEQ ID NO:49 nucleotide).

Non-human mammals with which the invention may be used include, for example, livestock animals, such as Bovidae, for example cows and sheep, and swine, also Equidae such as horses, canines such as companion domesticated dogs and felines such as companion domesticated cats, primates, Lagomorphs such as rabbits and Rodentia such as rats and mice. The invention is also applicable in birds such as foul, for example, chickens, turkeys and quail, ducks and geese. Accordingly, the invention provides corresponding embodiments and variations as described herein for mammals but applied to avians, such as the aforementioned avians. The sequences of *Gallus gallus* FGF2 (NCBI Reference Sequence: NM 205433.1; SEQ ID NO:50 peptide, SEQ ID NO:51 nucleotide), *Gallus gallus* FGFR1 (NCBI Reference Sequence: NM_205510.1; SEQ ID NO:52 peptide, SEQ ID NO:53 nucleotide), *Gallus gallus* FGFR2 (NCBI Reference Sequence: NM_205319.1; SEQ ID NO:54 peptide, SEQ ID NO:55 nucleotide), and *Gallus gallus* FGFR3 (NCBI Reference Sequence: NM 205509.2; SEQ ID NO:56 peptide, SEQ ID NO:57 nucleotide) also form part of this disclosure.

While the above examples relate to FGF2 and its receptors, the invention also provides corresponding embodiments for each embodiment and variation described herein for a fibroblast growth factor and/or FGF receptor generally, and for other specific fibroblast growth factors such as, but not limited to, FGF1 and FGF3.

Each of the patents and other publications cited in this disclosure is incorporated by reference in its entirety.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method for increasing humoral immune response to vaccination with an immunogen in a mammal, comprising:

in conjunction with the vaccination of a mammal to an immunogen other than FGF2, inhibiting the activity of FGF2 in the mammal by administering an antibody or fragment thereof that binds FGF2 to the mammal, thereby increasing the humoral immune response to the immunogen.

2. The method of claim 1, wherein the mammal is a human.

3. The method of claim 2, wherein the mammal is a geriatric human.

4. The method of claim 2, wherein the human has HIV disease.

* * * * *